United States Patent
Nti-Gyabaah et al.

(10) Patent No.: US 9,556,258 B2
(45) Date of Patent: Jan. 31, 2017

(54) PURIFICATION OF FUSION PROTEINS

(75) Inventors: Joseph Nti-Gyabaah, West Greenwich, RI (US); Ijeoma Ikechukwu, Carteret, NJ (US); Matthew Pettroff, Secaucus, NJ (US); Christine Cho Lee, Cohoes, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 82 days.

(21) Appl. No.: 14/131,280

(22) PCT Filed: Jul. 3, 2012

(86) PCT No.: PCT/US2012/045339
§ 371 (c)(1),
(2), (4) Date: Mar. 17, 2014

(87) PCT Pub. No.: WO2013/009526
PCT Pub. Date: Jan. 17, 2013

(65) Prior Publication Data
US 2014/0187751 A1 Jul. 3, 2014

Related U.S. Application Data

(60) Provisional application No. 61/505,710, filed on Jul. 8, 2011.

(51) Int. Cl.
| | | |
|---|---|---|
| C07K 1/14 | (2006.01) | |
| C07K 1/18 | (2006.01) | |
| C07K 1/22 | (2006.01) | |
| C07K 16/18 | (2006.01) | |
| C07K 1/36 | (2006.01) | |
| C07K 16/06 | (2006.01) | |
| C07K 14/705 | (2006.01) | |

(52) U.S. Cl.
CPC .............. *C07K 16/18* (2013.01); *C07K 1/36* (2013.01); *C07K 14/70578* (2013.01); *C07K 16/065* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| 7,427,659 B2 | 9/2008 | Shukla et al. |
| 2004/0147733 A1 | 7/2004 | Olsen et al. |
| 2006/0194953 A1 | 8/2006 | Bonnerjea et al. |
| 2008/0167450 A1 | 7/2008 | Pan |
| 2009/0292113 A1 | 11/2009 | Sondermann et al. |
| 2010/0112597 A1 | 5/2010 | Bian |
| 2010/0267932 A1 | 10/2010 | Eon-Duval et al. |
| 2011/0081679 A1 | 4/2011 | Jing et al. |

FOREIGN PATENT DOCUMENTS

| WO | 03059935 A2 | 7/2003 |
| WO | 2004008100 A2 | 1/2004 |
| WO | 2008025747 A1 | 3/2008 |
| WO | 2010127069 A1 | 11/2010 |
| WO | 2011017514 | 2/2011 |

OTHER PUBLICATIONS

Banta, Practical use of QbD: Defining the design space of an anion exchange chromatography unity operation by multi-variant experimentation, Abstracts of Papers, 241 st ACS National Meeting & Exposition, Anaheim, CA, United States, Mar. 27-31, 2011, Mar. 2011, abstract.

Fahrner et al., Industrial Purification of Pharmaceutical Antibodies: Development, Operation, and Validation of Chromatography Processes, Biotechnology and Genetic Engineering Reviews, vol. 18, (Jul. 2001), pp. 301-327.

Fisher et al., The high throughput purification of Fc-fusion proteins, Process Biochemistry 41 (2006) 2473-2476.

Kim et al., Construction and Purification of the Murine p75-murine IgG1 Fusion Protein, Journal of Investigative Dermatology Symposium Proceedings (2007) 12, 48-49.

*Primary Examiner* — Michael Pak

(57) ABSTRACT

The invention relates generally to methods for purifying a Fc-fusion protein produced in a eukaryotic expression system. More specifically, the invention provides a robust and scalable downstream purification process suitable for use in manufacturing TNFR:Fc for human administration which comprises an optimized Protein A affinity chromatography step and two ion exchange chromatography steps both of which are operated in the bind-and-elute mode.

16 Claims, 24 Drawing Sheets

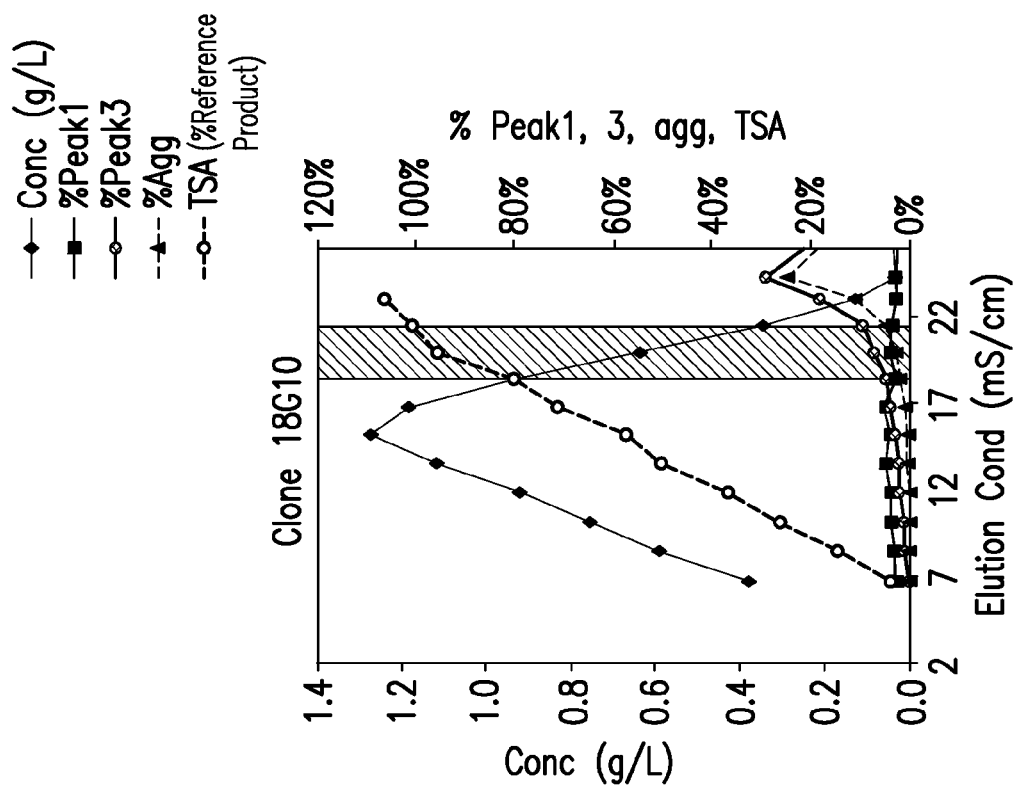
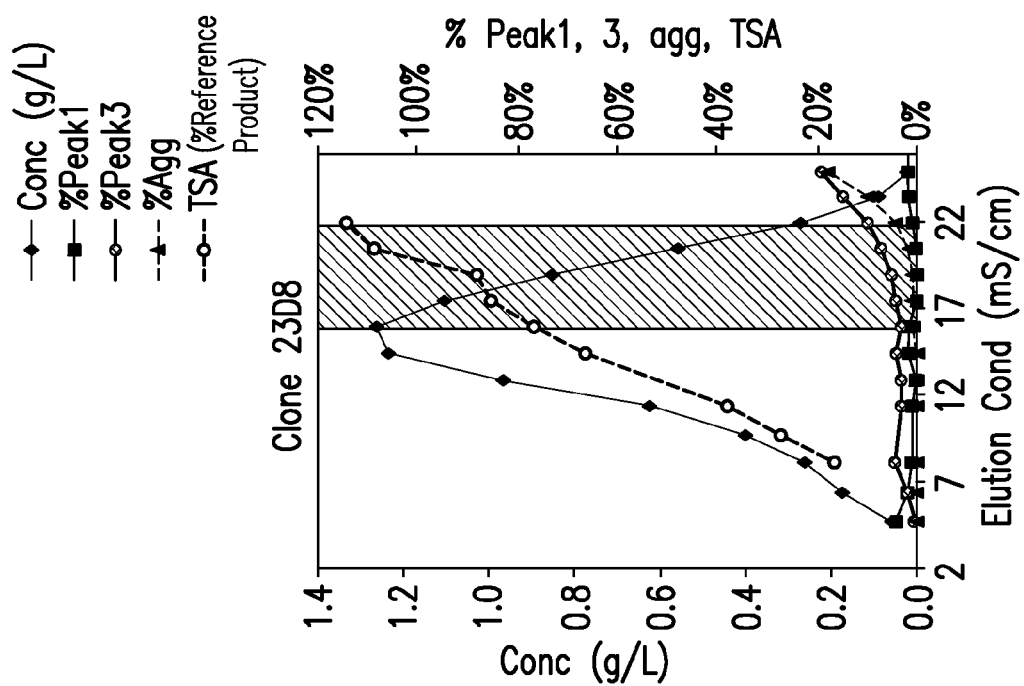
FIG.21B
FIG.21A

PURIFICATION OF FUSION PROTEINS

CROSS REFERENCE TO RELATED APPLICATIONS

This application is a U.S. National Phase application under 35 U.S.C. §371 of PCT Application No. PCT/US2012/045339, filed Jul. 3, 2012 which claims priority under 35 U.S.C. §119(e) from U.S. Provisional Application Ser. No. 61/505,710, filed Jul. 8, 2011.

FIELD OF THE INVENTION

The invention relates generally to methods for purifying an Fc-fusion protein produced in a eukaryotic expression system. More specifically, the invention provides a robust and scalable downstream purification process suitable for use in manufacturing TNFR:Fc for human administration.

BACKGROUND OF THE INVENTION

To ensure the safety of biopharmaceuticals, regulatory agencies impose stringent purification standards and quality attributes (identity, strength, and purity) for proteins intended for human administration. The standards mandate that protein-based therapeutic products are substantially free from impurities, including product related contaminants, such as aggregates, fragments and variants of a recombinant protein, and process related contaminants, such as leached chromatography resins, media components, DNA, host cell proteins, viral contaminants and endotoxins.

Process development can often be the rate-limiting step in the production of suitable quantities of biopharmaceutical drug candidates for clinical trials. Manufacturers of recombinant biopharmaceuticals have to deliver products with consistent quality attributes in order to assure reproducible clinical performance. Production of high purity biopharmaceuticals to support clinical development usually requires more than a single-step purification process. One of the greatest challenges in the development of a biopharmaceutical is the establishment of efficient and cost effect manufacturing processes which can reproducibly produce product of sufficient purity and biological activity.

Typically, down-stream processing of recombinant proteins relies heavily on process chromatography, with between two and five chromatography unit operations. Because downstream processing constitutes between 50-80% of all manufacturing costs, the biopharmaceutical industry considers bioprocess development as in integral component of product development and as a source of competitive advantage. Accordingly, companies involved in the large-scale manufacturing of monoclonal antibodies (mAbs) have made significant investments to establish upstream and downstream bioprocess platforms, in order to ensure their ability to consistently produce large quantities of pharmaceutical-grade mAbs.

Commercial scale purification processes typically include at least the following steps: cell lysis to recover an intracellular protein or recovery of a protein from the media in case of a secreted protein; removal of cellular debris using differential centrifugation or filtration to obtain a clarified sample containing the protein of interest; use of a variety of chromatography media in a multi-step process to separate a protein of interest from the various impurities in the sample. The primary consideration in downstream process development is drug purity. In addition, the process must be robust, reliable and scalable (Shukla, A et al. *Journal of Chromatography B*, 848:28 (2007).

Despite the recognized advantages of a having an established purification platform, differences in the biochemical properties and purification behavior of individual mAbs has led to the realization that downstream processing cannot be reduced to a single templated process that will be generally applicable to every biopharmaceutical drug. As a result, downstream purification processes have evolved towards defined operation parameters and a set of unit operations which are employed to create a common framework that is suitable for use the development of a product-specific process. The operation parameters serve to establish performance expectations for the individual unit operations and to bracket acceptable operating conditions, thereby limiting the amount of experimentation required to develop a protein-specific purification scheme. In practice, the unit operations initially developed for the downstream processing of mAbs can be modified for use in the development of processes suitable for use in the manufacturing of alternative types of biopharmaceuticals, including human IgG Fc fusion proteins.

Currently, there is still an unmet need for efficient and robust purification methods for Fc-fusion proteins which are amenable to the large-scale production of final products that are suitable for human administration.

The references cited in the present application are not admitted to be prior art to the claimed invention.

SUMMARY OF THE INVENTION

A downstream process for TNFR:Fc has been developed resulting in highly purified TNFR:Fc with an overall reduction of misfolded Fc-fusion protein to less than 5% (range 4.5% to 0.2%), reduction of aggregates to less than 5% (range 5% to 0.5%) and reduction of fragments (including free Fc levels) to less than 5% (range 4.5% to 0%). In addition, the process disclosed herein improves the total yield of sialylated TNFR:Fc.

The present invention is based, in part, on the development of a purification method which includes an optimized pre-harvest conditioning protocol in combination with three optimized chromatography unit operations, including a Protein A capture step and two ion exchange chromatography steps both of which are run in bind and elute mode. The methods of the invention are outlined in the flowcharts provided in FIGS. 1 and 2. The purification process of the invention significantly reduce the amount and extent of impurities such as incomplete Fc-containing protein fragments, aggregates and host cell proteins (HCPs) that may be present in the source media obtained from a eukaryotic expression system and produces high yields of biologically active and pure protein suitable for human administration.

In one embodiment the invention provides a method of purifying a Fc-fusion protein from one or more impurities present in a sample, comprising the steps of: a) providing a sample comprising a Fc-fusion protein produced in a eukaryotic expression system; b) binding the Fc-fusion protein present in the sample to a Protein A affinity chromatography resin; c) eluting the Fc-fusion protein from the Protein A resin, wherein the eluted product provides a second sample, optionally referred to as a Protein A Product (PAP); d) binding the PAP to a cation exchange (CEX) chromatography resin; e) eluting the second sample from the CEX resin, wherein the eluted product provides a third sample, optionally referred to as a CEX Product (CEXP); f)

binding the CEXP to an anion exchange (AEX) chromatography resin; and g) eluting the third sample from the AEX resin wherein the eluted product provides a purified Fc-fusion protein composition.

In a particular embodiment, the downstream purification process is used to purify a dimeric recombinant glycoprotein (e.g., a Fc-fusion protein) produced in either a glycoengineered *Pichia pastoris* yeast expression system. In an alternative embodiment the process is used to purifidy a Fc-fusion protein produced in a mammalian (CHO cell) expression system. More specifically, the examples provided herein exemplify the methods of the invention by using the disclosed downstream process to purify a p75 TNFR:Fc fusion protein, consisting of the extracellular ligand binding portion of the human 75 kilodalton human tumor necrosis factor receptor linked to a constant region (Fc) of human IgG1. However, the use of this particular Fc-fusion protein in the examples is not intended to limit the scope of the invention, which is more broadly useful for the downstream purification of any Fc-fusion protein.

As shown herein the optimized downstream purification process of the invention can be used to prepare a highly purified TNFR:Fc protein isolated from a CHO cell culture expression system and purified, wherein the purified protein has a purity of >99% and a TSA level of >18 mMol. According to the method disclosed herein, the TNFR:Fc protein is eluted from Protein A using a linear pseudo gradient that incorporates the elution stregths of sodium citrate buffer (50 mM to 100 mM citrate) and a decreasing pH gradient ranging from pH 5.0 to 3.5. As shown herein, use of a pseudo elution gradient, starting at higher pH and lower buffer strength, mitigates the effect of aggregate formation during Protein A elution due to the shallow pH transition curve.

As shown herein, use of the optimized operational parameters disclosed herein function to decrease the burden on subsequent chromatography steps. The optimized protein A step disclosed herein improves the purity of the Protein A product to greater than 80% after the first capture step. The disclosed Protein A chromatography step has been optimized to remove product-related impurities (misfolded protein of interest, aggregates, fragments and improperly siaylated species) which has the effect of reducing the burden of downstream purification steps Both of the ion exchange chromatography steps of the invention are operated in bind-and-elute mode. The cation exchange chromatography is preferably performed with NaCl elution gradient at pH 4.0. In an alternative embodiment, an isocratic elution can be performed with buffer at a conductivity and pH that will prevent the elution of aggregates and HCPs. Preferably, the Fc-containing protein is eluted from the cation exchange resin with a step gradient at a conductivity ranging from about 10 to about 50 mS/cm at a pH of about 3.5 to about 6.0. The CEX step of the process has been optimized to efficiently eliminates Host Cell Protein (HCP), DNA and leached protein A ligand while retaining TNFR:Fc fusion proteins with high TSA levels. The CEX step of the disclosed method provides an intermediate purification step for the Fc-containing protein.

In accordance with the present invention, the eluate from the cation exchange step is then subjected to an anion exchange chromatography (AEX) operated in bind and elute mode as a product polishing step. AEX was performed at pH 8.0, with elution by a 20 CV linear ionic strength gradient from 0-0.3M NaCl, with collection of 1 CV fractions. The optimized AEX unit operation of the disclosed e invention further reduces aggregates 1 to 2 fold and host cell proteins 1 to 5 fold. Using the optimized operating conditions disclosed herein the anion exchange chromatography step further enriched TSA levels and removed remaining process residuals.

Use of the optimized Protein A capture step in sequence with the two optimized ion exchange polishing chromatography steps, both of which are run in the bind and elute mode, further increase the purity of the Fc-fusion protein preparation to >90%, with concomitant control of the total sialic acid (TSA) content of the final purified protein. In practice, the disclosed purification process can be used to purify an Fc-fusion protein product with purity of >99%. In one embodiment, the downstream purification process of the invention is used to prepare highly purified TNFR:Fc protein, obtained from a CHO cell culture expression system, a having a purity of >99% and a TSA level of >18 mMol.

Reference to open-ended terms such as "comprises" allows for additional elements or steps. Occasionally phrases such as "one or more" are used with or without open-ended terms to highlight the possibility of additional elements or steps.

Unless explicitly stated, reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 21 Eluate product profiles of two clones in CHO cell line during AEX chromatography.

DETAILED DESCRIPTION OF THE INVENTION

Definitions

Figure 1:
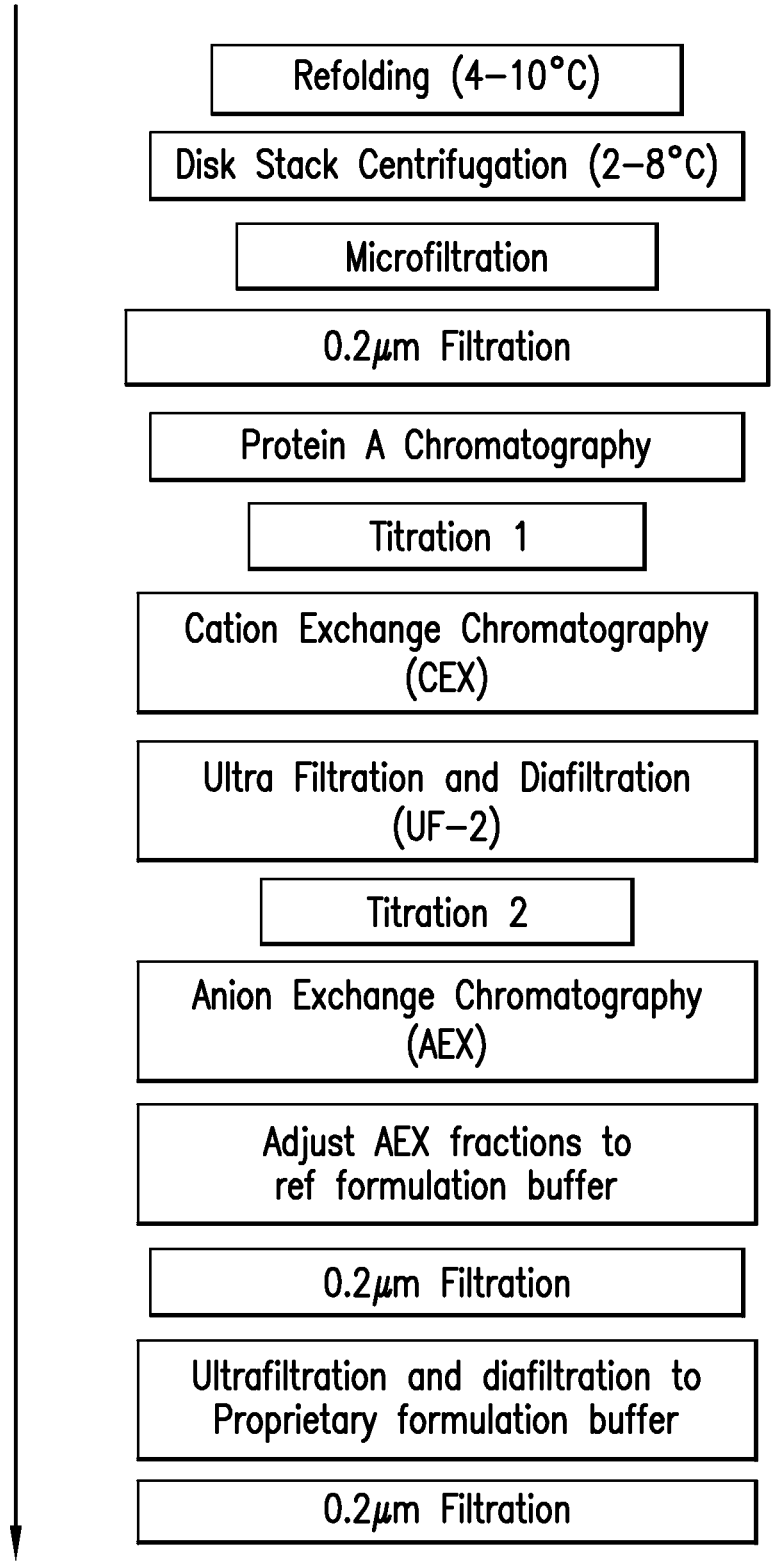
FIG. 1 Depicts a purification scheme for TNFR:Fc produced in glycoengineered *Pichia pastoris*.

As used herein the term "upstream process" refers to process steps associated with the production of a recombinant protein by culture and propagation of host cells. Upstream process considerations include clone selection methodologies, media selection, fed-batch culture operating conditions, culture feeding strategies.

As used herein the term "downstream process" refers to process steps associated with the purification of a recombinant protein and removal of impurities.

As used herein the term "robust process" refers to a process that performs adequately within it operation parameters, consistently providing material of defined quality, purity and yield.

The term "chromatography" refers to any kind of technique which separates an analyte of interest (e.g., an Fc region containing protein such as IgG fusion protein) from other molecules present in a mixture. Usually, the analyte of interest is separated from other molecules as a result of differences in rates at which the individual molecules of the mixture migrate through a stationary medium under the influence of a moving phase, or in bind and elute processes.

The terms "purifying," "separating," or "isolating," as used interchangeably herein, refer to increasing the degree of purity of a polypeptide or protein of interest or a target protein from a composition or sample comprising the polypeptide and one or more impurities or contaminants. Typically, the degree of purity of the target protein is increased by removing (completely or partially) at least one impurity from the composition.

A "purification step" or "unit operation" may be part of an overall purification process resulting in a "homogeneous" composition or sample, which is used herein to refer to a composition or sample comprising less than 1000 ppm HCP in a composition comprising the protein of interest, alternatively less than 900 ppm, less than 800 ppm, less than 700 ppm, less than 600 ppm, less than 500 ppm of HCP.

The terms "contaminant," "impurity," and "debris," as used interchangeably herein, refer to any foreign or objectionable molecule, including a biological macromolecule such as a DNA, an RNA, one or more host cell proteins, endotoxins, lipids and one or more additives which may be present in a sample containing the Fc containing target protein that is being separated from one or more of the foreign or objectionable molecules using a process of the present invention. Additionally, such a contaminant may include any reagent which is used in a step which may occur prior to the purification process.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate {e.g., a harvested cell culture fluid ("HCCF") comprising a protein of interest such as a fusion protein expressed in a CHO cell). The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another cell type, e.g., a eukaryotic cell other than CHO cells, an insect cell, or a plant cell, of a yeast cell, HCP refers to the proteins, other than target protein, found in a lysate of the host cell.

As used herein the term "preharvest conditioning" refers to treatment or adjustment of the cell containing fermentation broth prior to harvest or obtaining the harvested cell culture fluid or any form of purification. This includes but is not limited to adjustment of temperature, addition of stabilizing excipients, the addition of oxidizing and reducing agents, dilution of the fermentation broth to reduce concentration of protein, the addition of surfactants, the addition of salt and the addition of organic solvents.

The term "affinity separation," or "affinity purification," as used herein, refers to any purification or assaying technique which involves the contacting a sample containing a target analyte (e.g., an Fc region containing protein) with an affinity media (e.g., a solid support carrying on it an affinity ligand known to bind the analyte such as, for example, e.g., Protein A or a variant thereof) known to bind the target analyte.

The terms "affinity chromatography" and "protein affinity chromatography," as used interchangeably herein, refer to a protein separation technique in which a target protein (e.g., an Fc region containing protein of interest or antibody) is specifically bound to a ligand which is specific for the target protein. Such a ligand is generally referred to as a biospecific ligand. In some embodiments, the biospecific ligand (e.g., Protein A or a functional variant thereof) is covalently attached to a chromatographic solid phase material and is accessible to the target protein in solution as the solution contacts the chromatographic solid phase material. The target protein generally retains its specific binding affinity for the biospecific ligand during the chromatographic steps, while other solutes and/or proteins in the mixture do not bind appreciably or specifically to the ligand.

Binding of the target protein to the immobilized ligand allows contaminating proteins or protein impurities to be passed through the chromatographic medium while the target protein remains specifically bound to the immobilized ligand on the solid phase material. The specifically bound target protein is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. In various methods according to the present invention, Protein A is used as a ligand for an Fc region containing target protein As used herein the term "fed-batch culture" refers to a production process based upon feeding a growth limiting nutrient to the culture. This allows the culture to achieve a high cell density in the production bioreactor and facilitates metabolic control of the cells to avoid the generation of side products.

The term "cell culture supernatant", as used herein, refers to a medium in which cells are cultured and into which proteins are secreted provided they contain appropriate cellular signals, so-called signal peptides. It is preferred that the Fc-fusion protein expressing cells are cultured under serum-free culture conditions. Thus, preferably, the cell culture supernatant is devoid of animal-serum derived components. Most preferably, the cell culture medium is a chemically defined medium.

The term "aggregates", as used herein, is meant to refer to protein aggregates. It encompasses multimers (such as dimers, tetramers or higher order aggregates) of the Fc-fusion protein to be purified and may result, e.g., in high molecular weight aggregates.

As used herein, the term "misfolded Fc-Fusion protein" refers to Fc-Fusion proteins that are incorrectly or improperly folded thus altering the three-dimensional structure. Misfolds can also encompass the term "aggregate". However, aggregates do not necessarily have to be misfolds.

The term "refolding agent" refers to compounds or a combination of compounds and/or conditions which assist during the process of correctly folding of a protein that is improperly folded, unfolded or denatured. Such compounds may function by stabilizing the native conformation of the protein (i.e., arginine, glycerol), acting as chelators (i.e. EDTA), or preventing aggregation (i.e., trimethylamine N-oxide (TMAO), PEG-3500), redox agents (i.e., glutathione, cysteine).

The term "disaggregation agent" refers to compounds or a combination of compounds and/or conditions which assist during the process of reversing the process of protein aggregation (such as dimmers, tetramers or higher order aggregates). Such compounds may function as mild denaturants (i.e., urea, guanidine hydrochloride), stabilizers of the native conformation of the protein (i.e., arginine, glycerol), and acting as chelators (i.e., EDTA).

The term "acidic variant" is a variant of a target protein which is more acidic (e.g., as determined by cation exchange chromatography) than the target protein. An example of an acidic variant is a deamidated variant.

As used herein the term "capture step" refers to the first downstream processing step which captures the product of interest (POI) from the harvested culture media, concentrates the product, and achieves a first separation of the POI from impurities (e.g., cells, cell debris, DNA, host cell proteins).

As used herein the term "polishing step" refers to a downstream processing step which occurs after the initial capture step and which is intended to remove smaller amounts of impurities that are present in the product stream and which are typically have more similarity to the product than the impurities removed during the capture step (e.g., aggregated forms of the product, structural variants including misfolded product and modified product).

The terms "target protein" and "protein of interest" as used interchangeably herein, refer to a protein or polypeptide, including but not limited to, an Fc-fusion protein that is to be purified by a method of the invention, from a mixture of proteins and, optionally, other materials such as cell debris, DNA, host cell proteins, media components, and the like.

By "binding" a molecule to a chromatography resin is meant exposing the molecule to chromatography resin under appropriate conditions (pH/conductivity) such that the molecule is reversibly immobilized in or on the chromatography resin by virtue of ligand-protein interactions. Non-limiting examples include ionic interactions between the molecule and a charged group or charged groups of the ion exchange material and a biospecific interaction between Protein A and an immunoglobulin.

The term "specific binding" as used herein, such as to describe interactions between a target protein (e.g., an Fc region containing protein) and a ligand bound to a solid support (e.g., Protein A bound to a solid phase matrix or resin), refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. Generally, the greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like.

The term "non-specific binding" as used herein, such as to describe interactions between a molecule of interest (e.g., a target protein has described herein) and a ligand or other compound bound to a solid support (e.g., Protein A bound to a solid phase matrix or resin), refers to binding of a protein of interest to the ligand or compound on a solid support through electrostatic forces, hydrogen bonding, hydrophobic forces, and/or van der Waals forces at an interaction site, but lacking structural complementarity that enhances the effects of the nonstructural forces. Examples of non-specific interactions include, but are not limited to, electrostatic, hydrophobic, and van der Waals forces as well as hydrogen bonding.

By "washing" a chromatography media is meant passing an appropriate buffer through or over the media.

The terms "flow-through process," "flow-through mode," and "flow-through chromatography," as used interchangeably herein, refer to a product separation technique in which at least one product {e.g., an Fc region containing protein) contained in a sample along with one or more contaminants is intended to flow through a chromatographic resin or media, while at least one potential contaminant or impurity binds to the chromatographic resin or media. The "flow-through mode" is generally an isocratic operation (i.e., a chromatography process during which the composition of the mobile phase is not changed).

As used herein, the term "buffer exchange step" refers to an in-line solution condition adjustment, which is typically an alternative in many conventional processes, to the use of a holding tank. In a typical buffer exchange step, two solutions can be mixed or titrated during transfer using solution blending in a pipe or mixing vessel, filtration device or apparatus. For example, a solution may be required to be diluted in order to reduce conductivity by blending the solution with another lower conductivity solution. Buffer exchange can be accomplished with the help of filtration devices, such as diafiltration, ultrafiltration and the like.

To "elute" a molecule (e.g., a polypeptide of interest or an impurity) from chromatography resin is meant to remove the molecule therefrom by altering the solution conditions such that buffer competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

The term "isocratic elution" is used here to refer to conditions in which the composition of the mobile phase is unchanged during the entire elution process.

The term "gradient elution" is used herein to refer generally to conditions wherein the salt strength of the mobile phase in increased during the elution starting with a solvent of relatively low ionic strength.

The term "pre-elution step" refers to the penultimate chromatography step prior to elution, where the target molecule remains bound to the column, but the buffer mixing during loading onto the next column does not adversely effect target yield or target purity. Non-limiting examples include equilibrating a Protein A column loaded with an Fc containing protein in a buffer suitable for cation exchange column loading such as pH 5.4 sodium acetate or pH 5.0 sodium citrate, then elution of the column with pH 3 sodium acetate onto a cation exchange column.

The terms "bind and elute mode" and "bind and elute process," as used interchangeably herein, refer to a product separation technique in which at least one product contained in a sample (e.g., an Fc region containing protein) binds to a chromatographic resin or media and is subsequently eluted.

The term "pooling strategy" and "pooling criteria" as used interchangeably herein, is used to describe the approach of combining and eliminating chromatography process eluate fractions to achieve target impurity clearance and enhance desired product quality attributes.

The term "chromatography resin" or "chromatography media" are used interchangeably herein and refer to any kind of solid phase which separates an analyte of interest (e.g., an Fc region containing protein such as an immunoglobulin) from other molecules present in a mixture. Usually, the analyte of interest is separated from other molecules as a result of differences in rates at which the individual molecules of the mixture migrate through a stationary solid phase under the influence of a moving phase, or in bind and elute processes. Non-limiting examples include cation exchange resins, affinity resins, anion exchange resins, anion exchange membranes, hydrophobic interaction resins and ion exchange monoliths. The volume of the resin, the length and diameter of the column to be used, as well as the dynamic capacity and flow-rate depend on several parameters such as the volume of fluid to be treated, concentration of protein in the fluid to be subjected to the process of the invention, etc. Determination of these parameters for each step is well within the average skills of the person skilled in the art.

The term "POROS chromatography media" refers to chromatography resins characterized by having very large throughpores and smaller diffusive pores. The relative balance of the two is manipulated in manufacturing to optimize surface area, and therefore capacity. Surface coatings and introduction of functional groups independently augment capacity and control selectivity. Control of functional group type, ligand density, and coating structure are used to fine-tune selectivity.

The terms "Protein A", "ProA", and "PrA" are used interchangeably herein and encompasses Protein A recovered from a native source thereof, Protein A produced synthetically (e.g., by peptide synthesis or by recombinant techniques), and variants thereof which retain the ability to bind proteins which have a CH2/CH3 region, such as an Fc region. Protein A is generally immobilized on a solid phase support material. The term "ProA" also refers to an affinity chromatography resin or column containing chromatographic solid support matrix to which is covalently attached Protein A.

A functional derivative, fragment or variant of Protein A used in the methods according to the present invention may be characterized by a binding constant of at least $K=10^{-8}$ M, and preferably $K=10^{-9}$ M, for the Fc region of mouse IgG2a or human IgG1. An interaction compliant with such value for the binding constant is termed "high affinity binding" in the present context. Preferably, such functional derivative or variant of Protein A comprises at least part of a functional IgG binding domain of wild-type Protein A, selected from the natural domains E, D, A, B, C or engineered mutants thereof which have retained IgG binding functionality.

Also, Protein A derivatives or variants engineered to allow a single-point attachment may also be used in the affinity chromatography step in the claimed methods. Single point attachment generally means that the protein moiety is attached via a single covalent bond to a chromatographic support material of the Protein A affinity chromatography. Such single-point attachment may also occur by use of suitably reactive residues which are placed at an exposed amino acid position, namely in a loop, close to the N- or C-terminus or elsewhere on the outer circumference of the protein fold. Suitable reactive groups are e.g. sulfhydryl or amino functions.

As used herein the term "contaminant Protein A" is any type of functional, IgG binding offspring of a Protein A or a functional derivative thereof as defined above which is obtained upon eluting bound antibody from a Protein A affinity chromatography column. Such contaminant Protein A species may result, e.g., from hydrolysis of peptide bonds which is very likely to occur by means of enzyme action in particular in industrial manufacturing. For example, dying cells in the cell culture broth or cells disrupted in initial centrifugation or filtration steps are likely to have set free proteases which can degrade the Protein A resin. This is particularly likely because Protein A chromatography is applied as an early step in downstream processing when the crudely purified, fresh product solution still harbors considerable protease activity.

As used herein the terms "ion-exchange" and "ion-exchange chromatography" are used to refer to a chromatographic process in which a solute or analyte of interest (e.g., an Fc region containing target protein) in a mixture interacts with a charged compound linked (such as by covalent attachment) to a solid phase ion exchange material such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode ion exchange chromatography.

The "pI" or "isoelectric point" of a polypeptide refer to the pH at which the polypeptide's positive charge balances its negative charge, pi can be calculated from the net charge of the amino acid residues or sialic acid residues of attached carbohydrates of the polypeptide or can be determined by isoelectric focusing.

The phrase "ion exchange material" refers to a solid phase that is negatively charged (i.e., a cation exchange resin) or positively charged (i.e., an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

The phrase "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g., SP-SEPHAROSE FAST FLOW™ or SP-SEPHAROSE HIGH PERFORMANCE™, from Pharmacia) and sulphonyl immobilized on agarose (e.g., S-SEPHAROSE FAST FLOW™ from Pharmacia). For example, cation exchange chromatography can be performed under conditions in which the resin bind the target molecule (e.g., an Fc region containing target protein) followed by elution (cation exchange bind and elution chromatography or "CIEX"). Alternatively, CEX can be run in a mode which it predominately binds the impurities while the target molecule "flows through" the column (cation exchange flow through chromatography FT-CIEX). The purification method disclosed herein utilizes a cation exchange chromatography step which is performed in a bind and elute mode.

The term "anion exchange resin" is used herein to refer to a solid phase which is positively charged, e.g., having one or more positively charged ligands, such as quaternary amino groups, attached thereto. Commercially available anion exchange resins include DEAE cellulose, QAE SEPHADEX™ and FAST Q SEPHAROSE™ (Pharmacia). Anion exchange chromatography can bind the target molecule (e.g., an Fc region containing target protein) followed by elution or can predominately bind the impurities while the target molecule "flows through" the column. The purification method disclosed herein utilizes an anion exchange chromatography step which is performed in a bind and elute mode.

As used herein the term "buffer" refers to a solution that resists changes in pH by the action of its acid-base conjugate components. Various buffers which can be employed depending, for example, on the desired pH of the buffer are described in Buffers. *A Guide for the Preparation and Use of Buffers in Biological Systems*, Gueffroy, D., ed. Calbiochem Corporation (1975).

A "salt" is a compound formed by the interaction of an acid and a base. Various salts which may be used in the buffers described herein include, but are not limited to, acetate (e.g., sodium acetate), citrate (e.g., sodium citrate), chloride (e.g., sodium chloride), sulphate (e.g., sodium sulphate), or a potassium salt.

The term "cation exchange buffer" refers to equilibration buffers with a pH and conductivity such that the target molecule (e.g., immunoglobulin) will bind to the cation exchange material.

As used herein the term "loading buffer" refers to a buffer which is used to load the sample or composition comprising the target molecule of interest (e.g., an Fc region containing target protein) and one or more impurities onto a chromatography column (e.g., an affinity column or an ion exchange column). The loading buffer has a conductivity and/or pH such that the molecule of interest (and generally one or more impurities) is/are bound to the chromatography resin or such that the protein of interest flows through the column while the impurities bind to the resin.

An "intermediate buffer" is used to elute one or more impurities from the chromatography resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" or "equilibration buffer" are used interchangeably herein, refers to a buffer used to wash or re-equilibrate the chromatography resin prior to eluting the polypeptide molecule of interest. In some cases, the wash buffer and loading buffer may be the same.

An "elution buffer" is used to elute the target protein from the solid phase. The conductivity and/or pH of the elution buffer is/are usually such that the target protein is eluted from the chromatography resin. The term "isocratic elution" is used to refer elution condition in which the composition of the mobile phase is unchanged during the entire elution process.

The term "gradient elution" and "linear gradient elution" are used interchangeably herein to refer to conditions wherein the solvent strength, or the concentration of the eluate ion, in mobile phase is increased during the elution starting with a solvent of relatively low solvent strength.

The term "pseudo gradient elution" is used to refer to conditions wherein two or more conditions are being altered during a gradient elution. An example of pseudo gradient method includes but is not limited to, increasing solvent strength of the mobile phase while concurrently decreasing pH of the mobile phase during the elution phase of Protein A chromatography to achieve higher levels of purity when compared to performing an isocratic elution or a gradient that alters one mobile phase condition. The combined effect of altering pH and salt concentration concurrently during ion exchange elution is another example of pseudo gradient elution.

The term "virus inactivation," "virus clearance," or "virus reduction," as used interchangeably herein, refers to any process which may render a virus incapable of infecting a cell or inhibit a virus function through a physico-chemical means. Typical virus inactivation methods include, but are not limited to, low pH treatment (e.g., below pH 4.5, below 4.0 or below 3.8), heat treatment, treatment with surfactants and radiation (e.g., ultraviolet light exposure). In some embodiments, virus inactivation methods are directed against retroviruses. In a particular embodiment, low pH conditions are used for virus inactivation as such conditions typically disrupt the virus lipid envelope, thereby inactivating the virus.

As used herein the terms "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as CH2/CH3 regions, can bind selectively to affinity ligands such as Protein A or functional variants thereof. In some embodiments, an Fe region containing protein specifically binds Protein A or a functional derivative, variant or fragment thereof.

The term "Fc-fusion protein", as used herein, is meant to encompass proteins, in particular therapeutic proteins, comprising an immunoglobulin-derived moiety, which will be called herein the "Fc-moiety", and a moiety derived from a second, non-immunoglobulin protein, which will be called herein the "therapeutic moiety", irrespective of whether or not treatment of disease is intended. In alternative embodiments, the Fc-fusion protein comprises a therapeutic moiety selected from an extracellular domain of TNFR1, TNFR2, or a TNF superfamily member, or a TNF binding and optionally inhibiting fragment thereof. A hallmark of the members of the TNFR superfamily is the presence of cystein-rich pseudo-repeats in the extracellular domain, as described, e.g., by Naismith J. H. and Sprang S. R. *Trends Biochem. Sci.* 23, 74-79 (1998). The two TNF receptors, p55 (TNFR1) and p75 TNFR (TNFR2) are examples of such members of the TNFR superfamily. In a particular embodiment, the Fc-fusion protein is Etanercept, an Fc-fusion protein containing the soluble part of the human p75 TNF receptor (TNFR) (E.G. WO91/03553, WO 94/06476). Etanercept is also referred to herein as "TNFR:Fc."

As used herein, the term "reference product, is used to refer to Etanercept (ENBREL). ENBREL lot numbers 1009164, 1011147, 1011803, 1011858 and 1008885 were used herein for comparison purposes.

Fc Fusion Proteins

Etanercept (Enbrel®) is a dimeric recombinant therapeutic glycoprotein, produced in a Chinese hamster ovary (CHO) mammalian cell expression system, and consisting of the extracellular ligand binding portion of the human 75 kilodalton (p. 75, TNFRII, WO91/03553, WO 94/06476) human tumor necrosis factor receptor linked to the constant region (Fc) of human IgG1. Etanercept is marketed for the treatment of at least rheumatoid arthritis, psoriatic arthritis, psoriasis and ankylosing spondylitis. Etanercept mediates its beneficial effects in these chronic inflammatory diseases by binding to and neutralizing the effects of the pro-inflammatory cytokine TNF-α.

In order to create soluble, secreted Fc-fusion proteins, that are released into the cell culture supernatant, either the natural signal peptide of the therapeutic moiety of the Fc-fusion protein is used, or preferably a heterologous signal peptide, i.e., a signal peptide derived from another secreted protein being efficient in the particular expression system used. If the Fc-fusion protein to be purified is expressed by mammalian cells secreting it, the starting material of the purification process of the invention is cell culture supernatant, also called harvest or crude harvest. If the cells are cultured in a medium containing animal serum, the cell culture supernatant also contains serum proteins as impurities.

In accordance with the present invention, the recombinant Fc-fusion protein can be produced in eukaryotic expression systems, including mammalian cells and glycoengineered yeast cells, resulting in glycosylated Fc-fusion proteins. Preferably, the Fc-fusion protein expressing and secreting cells are cultured under serum-free conditions. The Fc-fusion protein may also be produced in a chemically defined medium. Typically, the starting material of the purification process of the invention is serum-free cell culture supernatant that mainly contains host cell proteins as impurities.

Glycosylation/TSA

TNFR:Fc (etanercept) is a therapeutic recombinant fusion protein comprised of the extracellular ligand binding portion of the human 75 kDa (referred to herein as p75, TNFR2 or TNFRII) human TNF-αreceptor linked to the constant region of human IgG1 (Fc region). Like the majority of proteins of therapeutic importance, etanercept requires N-glycosylation for biological activity. It is well-known that mammalian cells and yeast cells differ in their abilities to incorporate post-translation modifications found on native human proteins. Only mammalian cells have the inherent capacity to carry out N-linked glycosylation of protein during secretion.

Glycosylated proteins are complex molecules and even a well-controlled product may consist of several hundred or more glycoforms with different glycan compositions on the same amino acid sequence. The in vivo biological activity of glycosylated proteins is known to be dependent on the number of sialic acid units per molecule, which is a result of the available sialylation sites, the antenniarity of the N-glycans and the completeness of sialylation (Shiestl, M., et al. *Nature Biotechnology* 29(4):310 (2011).

Yeast provide an alternative protein expression system, however, glycoproteins produced in wild-type yeast contain potentially immunogenic high-mannose type N-glycans. The difference in glycosylation patterns between mammalian cells and yeast limits the use of yeast expression systems for the production of monoclonal antibodies and other therapeutic proteins, including IgG Fc-fusion proteins. Human glycosylation pathways have been engineered into the yeast *P. pastoris* to provide host cells which perform specific humananized N-glycosylation reactions with high fidelity. The glycoengineered cell lines of *P. pastoris* have been used to successfully produce recombinant monoclonal antibodies (Jiang, Y., et al. *Protein Expression and Purification*, (76) 7 (2011) and Fc-fusion proteins with humanized N-glycan structures.

Etanercept displays both O-linked and N-linked glycans. The N-linked carbohydrate structures exhibit many features characteristic of glycans naturally occurring in human proteins. For example, its mostly bi-antennary structures are produced with complex-type branches consisting predominantly of the disaccharide Gal 1,4 GlcNAc capped by a terminal sialic acid residue. However, incomplete synthesis of these structures in CHO cells often imparts a range of structural heterogeneity to the protein, leading to batch to batch variability. O-linked glycans found on Etanercept are of the so-called mucine type. Since the pharmacokinetic properties of etanercept are strongly dependent on the structure of the complex N-linked carbohydrates and the degree of sialic acid capping the O-linked glycans, insufficient or inconsistent sialylation and galactosylation can in turn result in variable clearance through the asialoglycoprotein or mannose/GlcNAc receptor-mediated pathways, potentially posing a significant problem for adequate reproducible dosing of the drug.

Heterogeneity can vary widely from clone to clone and is dependent on both culture conditions and mode of production. An ability to enrich for specific glycoforms would thus be highly desirable, and GlycoFi's *Pichia pastoris* yeast expression platform affords the production of this therapeutic protein with a more homogeneous, although not identical, humanized glycosylation pattern. In order to be considered as a biosimilar the terminal monosaccharide of the N-linked complex glycans of the *Pichia* produced protein should be occupied by sialic acid. However, insufficient or inconsistent sialylation can provide a significant obstacle in achieving process consistency. The purification challenges resulting from variations in the level of sialylation are addressed in the downstream process disclosed herein by defining appropriate unit operations and optimizing the conditions (e.g., resin selection, mode of operation, buffers, elution conditions) for each chromatography step.

Control of glycosylation pattern and terminal sialylation are carefully monitored during the purification of TNFR:Fc fusion protein due to the half-life and therapeutic potency of most glycoproteins, is dependent on the presence of terminal sialic acid. Sialylation, the final step of human glycosylation, is particularly difficult to accomplish in yeast, because wild-type yeast lacks all the ability to produce the N-glycosylated precursors terminating in β-1,4-galactose, the biosynthetic capability to produce the sugar nucleotide precursor cytidine monophosphate (CMP)-sialic acid [specifically, CMP-N-acetylneuraminic acid (CMP-NANA)], the transporter to shuttle CMP-sialic acid into the Golgi, and a sialyltransferase to transfer sialic acid to terminal galactose on the nascent glycoprotein. The loss of sialic acid frequency leads to reduced glycoprotein solubity and reduced circulatory half life. As a result the purification and therapeutic effectiveness is dependent on the sialic acid content Brousseau, D. T. and Sliwkowski, M. B., *Biotechnology*, 13, 692-698 (1995). Shantha Raju, T. S., et al. *Biochemistry* 40, 8868-8876 (2001) showed increasing the level of terminal sialylation in TNFR-Fc molecules expressed in Chinese hamster ovary (CHO) cells increased the serum half life.

Sialic acid content of the therapeutic protein is determined using the following method. Briefly, 10-20 ug of protein sample is mixed with 400 uL of 0.1 M Hydrochloric Acid. This is then followed by heating for 1 hour at 80° C. The resulting mixture is dried for an hour in SpeedVac. Then the product is reconstitute with 500 uL of HPLC water and processed for chromatographic analysis on Dionex HPAEC-PAD system. The area under the curve is used to calculate the amount of sialic acid in pmols and then the molar ratio of sialic acid to protein was calculated. The reference product is calculated at 100 percent TSA and percent TSA in the POI is expressed relative to reference product.

Parameters that contribute to the improved TSA levels in the eluate stream are present in all three chromatographic steps. For the Protein A step the pseudo gradient employed selectively enriches the TSA levels primarily in start of the product elution. The pseudo gradient uses both pH and buffer strength concomitantly and allows for a unique and highly selective product profile that exhibits high levels of TSA. The pooling strategy that was employed for the Protein A step also shows consistent enrichment of TSA content of TNFR:Fc produced in both glyco-engineered *Picchia* host cell and CHO cell lines. Improved TSA profiles are also evident in during CEX chromatography. Despite the heterogeneity present in multiple CHO cell lines and glyco-engineered *Picchia*, there is consistent improvement of the sialic acid content in the product pool of CEX chromatography. This can be attributed to the mode at which CEX chromatography is operated (bind and elute) and the pooling strategy employed at the conclusion of the unit operation. The modality in which AEX is operated (bind and elute) is a contributing factor to the enhanced TSA levels that are exhibited in the product pool. AEX is typically operated in flowthrough (F/T) mode, however use of an AEX F/T unit operation has been observed to provide minimal improvement of TSA levels in the F/T product.

Refolding/Misfolding

TNFR:Fc comprises 7 disulfide bonds in the Fc region and 22 disulfide bonds in the TNF receptor region of the protein. Accordingly, there is a high probability of disulfide scrambling during a downstream processing protocol. TNFR:Fc resulting from the fermentation of *Pichia* host cells had less than 20% correctly folded product of interest (POI), with the remainder aggregated or misfolded which presented significant challenges for the downstream purification efforts. The invention described in WO 2002/068455 is premised on the observation that expression of TNFR:Fc (p75TNFRII: Fc fusion protein also known as etanercept) in CHO results in a preparation comprising a mixture of correctly folding TNFR:Fc, fragments and misfolded and/or aggregated protein product. The disclosure indicates that while some regions or domains of recombinant proteins may be properly folded, other regions or domains may have undesired conformations. The disclosure indicates that fraction #3 of the hydrophobic interaction column (HIC) was of particular interest since it can comprise from 20 to 60% of the sample and was shown to exhibit low TNF binding activity and bioactivity in comparison with the protein collection in Fraction #2 of the HIC column eluate.

WO 2002/068455 provides a method of contacting a preparation of a recombinant protein (i.e., p75 TNFR:Fc) that has been produced by mammalian cells with a reduction/oxidation coupling reagent, at a pH of about 7 to about 11, and isolating a fraction of the preparation of the recombinant protein with a desired conformation. All of the experimental studies published in WO 2002/068455 used partially purified TNFR:Fc protein mixtures obtained CHO cell produced material that was eluted from either a Protein A or a HIC columns.

Prior Art Purification Schemes

WO 03/059935 discloses a purification process for a p75 TNFR:Fc-fusion protein using a combination of hydroxyapatite chromatography and affinity chromatography on Protein A. The disclosed purification method provides for separating proteins comprising at least one constant antibody immunoglobulin domain using hydroxyapatite resin in flow-through mode such that the Fc-fusion protein does not bind to hydroxyapatite but the other protein(s) do bind. The method disclosed herein does not utilize hydroxyapatite chromatography. In addition to this, use of ion exchange chromatography is not mentioned for purification of the p75 TNFR:Fc-fusion protein.

U.S. Pat. No. 7,427,659 discloses a purification process for separating a target protein including a recombinant TNFR:Fc fusion protein produced in a cell culture) fro a mixture containing the target protein and contaminants (such as HCP), by contacting the mixture with a hydrophobic absorbent comprising branched hydrocarbon functional groups (e.g., a HIC resin) in an aqueous salt solution and collecting the unbound flow-through fraction containing the target protein. Use of HIC in flow-through was described as being surprisingly efficient, resulting in a significantly higher recovery of the target protein in a single step, thus simplifying and improving the efficiency and cost of the protein purification process. The method disclosed herein does not utilize HIC chromatography.

U.S. Pat. No. 6,870,034 discloses a method for purifying CH2/CH3 region-containing proteins, such as antibodies and immunoadhesins, by Protein A affinity chromatography. The disclosure describes the use of intermediate wash buffers, other than TMAC or TEAC (both of which are disclosed in U.S. Pat. Nos. 6,127,526 and 6,333,398) for use in Protein A chromatography, to remove the contaminants, but not the immobilized the protein of interest, bound to the Protein A column. One of the disclosed intermediate buffers comprises a detergent and a salt, another comprising a solvent and a salt and a third wash buffer comprises a polymer and a salt. The CH2/CH3 region-containing proteins exemplified in the disclosure are antibodies.

In contrast to the wash buffers described in U.S. Pat. No. 6,870,034, the wash buffer used in the Protein A purification step disclosed herein, which targets non product related impurities, is an aqueous (phosphate) based buffer with salt at pH at pH 5.5-5.8. In addition, the pseudo gradient used during elution removes non-product related impurities, fragments, aggregates and misfolds. Use of the disclosed optimized Protein A conditions also results in an enhancement of the desired sialylation pattern of the protein (i.e., improved TSA content).

EP 1 561 756 discloses that Protein A or G based chromatography alone may not be sufficient for the separation of DNA contaminants from proteins and that in order to purify a protein, further steps such as anion or cation exchange chromatography, hydroxyapatite chromatography or combinations thereof may be used. No specific order has been proposed for these chromatographic steps. Additionally, the proteins EP 1 561 756 refers to are hematopoietic factors, cytokines and antibodies. Fc-fusion proteins are not mentioned in EP 1 561 756.

EP 1 614 693 describes a method for purification of antibodies based on Protein A affinity chromatography, anion exchange chromatography and cation exchange chromatography. In this document, it is specified that the antibodies are purified via anion exchange and cation exchange chromatography in that order, or, alternatively, via cation exchange chromatography followed by hydrophobic chromatography. The hydrophobic chromatography may be replaced by any other type of chromatography including hydroxyapatite chromatography. Fc-fusion proteins are not mentioned in EP 1 614 693.

US2010/0267932 discloses methods for the purification of Fc-fusion proteins having a pI between 6.9 and 9.5 comprising Protein A or G affinity chromatography, cation exchange chromatography, anion exchange chromatography and hydroxyapatite chromatography. The sequence or order of purification steps used for purification is unlike one used in US2010/0267932. The downstream process disclosed herein comprises one less chromatography step and utilizes an AEX purification step that is operated in bind and elute mode, as opposed to the flow-through mode described in US 2010/0267932.

Therefore, there is still an unmet need for efficient purification methods for Fc-fusion proteins resulting in such purity as to be suitable for human administration.

Present Invention

The present invention is based, in part, on the development of a purification method based on an optimized pre-harvest conditioning protocol in combination with three optimized chromatography unit operations, including a Protein A capture step and two ion exchange chromatography steps which can significantly reduce the amount or extent of impurities such as incomplete Fc-containing protein fragments, aggregates and host cell proteins (HCPs) that may be present in a fluid or composition of an Fc-containing protein.

The downstream process disclosed herein includes a novel pH shift refolding strategy which was incorporated into the harvest step to improve productivity, and a high throughput method was used to rapidly optimize the affinity Protein A chromatography step, thereby upgrading the purity of the POI to >80% after the primary capture step. Integration of these steps with two newly developed ion exchange polishing chromatography steps which are run in the bind and elute mode further increased the purity to >90%, with concomitant control of the total sialic acid content of the final drug substance. The downstream process was originally developed *Pichia*-expressed TNFR:Fc fusion protein, and subsequently adapted for the purification of CHO-expressed TNFR:Fc.

Cho-Expressed TNF-R Fusion Protein

In the methods disclosed herein production of TNFR:Fc is achieved by the large-scale culturing of either glycoengineered *Pichia pastoris* or Chinese Hamster Ovary (CHO) cells that have been engineered to express a recombinant dimeric TNFR DNA construct. Recombinant proteins are proteins produced by the process of genetic engineering. The term "genetic engineering" refers to any recombinant DNA or RNA method used to create a host cell that expresses a gene at elevated levels, at lowered levels, and/or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in Current Protocols in Molecular Biology, Ausubel et al., eds. (Wiley & Sons, New York, 1988, and quarterly updates) and Sambrook et at., Molecular Cloning: A Laboratory Manual (Cold Spring Laboratory Press, 1989).

The purified Fc-fusion proteins resulting from the downstream processing method of the invention is preferably highly purified Fc-fusion protein. Highly purified Fc-fusion protein is determined, for example, by the presence of a single band in a silver-stained, non-reduced SDS-PAGE-gel. Purified Fc-fusion protein may also be defined as eluting as a single peak in HPLC.

The Fc-fusion protein preparation obtained from the purification process of the invention may contain less than 20% of impurities, preferably less than 10%, 5%, 3%, 2% or 1% of impurities, or it may be purified to homogeneity, i.e., being free from any detectable proteinaceous contaminants as determined e.g., by silver stained SDS-PAGE or HPLC, as explained above.

Purified Fc-fusion proteins may be intended for therapeutic use, in particular for administration to human patients. If purified Fc-fusion protein is administered to patients, it is preferably administered systemically, and preferably subcutaneously or intramuscularly, or topically, i.e., locally. For this purpose, the purified Fc-fusion protein of the invention may be formulated into pharmaceutical composition, i.e., together with a pharmaceutically acceptable carrier, excipients or the like.

Chromatography Steps

Generally speaking chromatography unit operations are used to separate a protein of interest from other proteins and contaminants present in a mixture on the basis of protein charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents.

Typically, downstream process platforms developed for monoclonal antibodies utilize a Protein A affinity purification step as the capture step followed by two or more polishing chromatography steps which have sufficient redundancy between them to assure product purity and robust operation of the downstream process. Usually one or more of the polishing steps is operated in flow-through mode (in which the POI does not bind to the column which retains the impurities). Hydroxyapatite interaction chromatography steps (HIC) and anion-exchange chromatography (AEX) steps are usually operated in flow-through mode for monoclonal antibodies, which tend to have high isoelectric points.

Protein A Capture Step

Protein A is a 43,000 Dalton protein that is produced by the bacteria *Staphylococcus aureus* and contains four binding sites to the Fc regions of IgG. Protein G is produced from group G Streptococci and has two binding sites for the IgG Fc region. Both proteins have been widely characterized for their affinity to various types of immunoglobulins. Since the binding sites for Protein A and Protein G reside in the Fc region of an immunoglobulin, Protein A and Protein G affinity chromatography also allows purification of so-called Fc-fusion proteins.

Protein A is widely used in downstream processes developed for the manufacture of monoclonal antibodies expressed in mammalian cell culture. Typically, Protein A affinity chromatography is used as a first purification step to directly capture the mAb product at a neutral pH, and it is usually operated under conditions designed to clear process residuals (such as host cell proteins (HCP, host cell DNA, and media components). The product eluted from the Protein A column at low pH usually contains process and product related impurities (including aggregated, variant and misfolded product), which necessitate subsequent chromatography steps.

The Protein A used for the affinity chromatography may can be recombinant. It may also be modified in order to improve its properties (such as, e.g., in the resin called MabSelect SuRe, commercially available from GE Healthcare). In one embodiment, the capture step is carried out using POROS MabCapture A perfusion chromoatography media. POROS MabCapture A media is a polymeric media designed for preparative purification of mAbs. The media consists of rigid cross-linked poly(styrene-divinylbenzene) flow-through particles with pore structure optimized for very rapid mass transport. The particle surface is coated with a polyhydroxylated polymer, which is further derivitized by convalent immobilization of a recombinant Protein A.

The purification methods disclosed herein utilize a Protein A affinity chromatography step as a capture step to bind the TNFR:Fc fusion protein produced in eukaryotic expression systems, including mammalian host cells and glycoengineered yeast strains. In practice, the Protein A unit operation functions to eliminate host cell proteins (HCPs), to concentrate the Fc-fusion protein stream and to remove Fc-fusion protein aggregates. Another objective of the Protein A capture step is enrichment of Total Sialic Acid (TSA) of the POI. As shown herein, using optimized operating parameters the Protein A capture step of the disclosed downstream processing method can reduce Fc-fusion protein aggregate levels to final aggregate values ranging form 0.5% to 3%. Host cell protein values were also reduced to ranging from 1000 ppm to 200 ppm.

In the method disclosed herein the wash buffer 6 mM sodium phosphate 500 mM NaCl, pH 5.5 is preferred. However, salt concentration of 400 mM to 1 M and/or a combination of pH ranging from 5.3 to pH 7.0 may also be used. Sodium phosphate buffer strength ranging from 2 mM to 35 mM sodium phosphate may also be used. The wash buffer is used to clear non-product related impurities such as host cell protein, DNA and other media related additions.

In the method disclosed herein, the POI is eluted from Protein A is carried using a linear gradient that incorporates the elution stregths of sodium citrate buffer (50 mM to 100 mM citrate) and a decreasing pH gradient ranging from pH 5.0 to 3.5. The Protein A elution step can be carried out in a buffer selected from sodium acetate or sodium citrate. Suitable buffer concentrations are, e.g., selected from 50 mM or 100 mM or 150 mM or 200 mM. The low pH conditions required for Protein A elution can often lead to aggregation issues for these products (Shukla, A. A., et al. *J Chromatogr A.* (2007)). The Protein A pseudo elution, gradient starting at higher pH and lower buffer strength, mitigates the effect of aggregate formation during Protein A elution due to the shallow pH transition curve. Higher levels of leached Protein A ligand is also encountered in Protein A product streams with lower pH elutions. The pseudo gradient elution dampens the effect of high levels of leached Protein A ligand in the product stream.

In practice, there are some significant disadvantages associated with the use of Protein A resins, including the fact that Protein A residues, which can be immunogenic can leach into the eluate, a consideration which requires the use of additional chromatagrophy steps to clear the Protein A residues. Other disadvantages include the cost of the resin, which can represent more than 30% of the total cost of raw material used for a commercial scale purification process, and the fact that the resin is difficult to sanitize because it is easily denatured by common sanitization solutions such as sodium hydroxide.

Ion Exchange Chromatography

Ion exchange chromatography systems are used for separation of proteins primarily on the basis of differences in charge. In ion exchange chromatography, charged patches on the surface of the solute are attracted by opposite charges attached to a chromatography matrix, provided the ionic strength of the surrounding buffer is low. Although protein retention on IEX resins is predominantly a function of electrostatic interactions, the interaction mechanisms of proteins with charged surfaces are known to be multimodal and to include non-electrostatic interactions including hydrophobic interactions, hydrogen bonding and van der Waals interactions.

Elution is generally achieved by increasing the ionic strength (i.e., conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

The "isoelectric point" or "pI" of a protein is the pH at which the protein has a net overall charge equal to zero, i.e. the pH at which the protein has an equal number of positive and negative charges. Determination of the pI for any given protein can be done according to well-established techniques, such as e.g. by isoelectric focusing. The method of the invention is used for purifying a TNFR:Fc-fusion protein having a pI ranging from 6.9 to 9.5.

The optimization of an LEX process requires the consideration of numerous interrelated parameters including the mode of operation (bind-and-elute or flow-through), dimensions of the column, loading buffer (type, concentration, pH), mode of elution (gradient, step-wise, isocratic), slope of an elution gradient and operational flow rate. In practice, the most significant factors are mode of operation and loading pH.

CEX

Cation exchangers can also be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Carboxymethyl (CM) and sulphopropyl (SP) have sodium as counter ion, for example.

In accordance with the present invention, the eluate from the Protein A chromatography unit operation is subjected to cation exchange chromatography. The cation exchange chromatography may be carried out on any suitable cation exchange resin, such as e.g. weak or strong cation exchangers. In one embodiment of the invention the CEX purification step is carried out POROS HS strong cation exchange resin run in bind and elute mode. POROS HS is a polymeric packings for cation exchange chromatography of peptides, proteins, and other biomolecules in a perfusion chromatography mode. It consists of cross-linked poly(styrene-divinylbenzene) flow-through particles with a bimodal pore size distribution for very rapid mass transport. The particles are surface coated with a polyhydroxylated polymer functionalized with sulfopropyl. POROS HS, is a strong cation exchangers, with complete surface ionization over a pH range of 1 to 14. POROS HS has the highest binding capacity and is recommended for applications leading to scale-up. Other resins that may be considered include source 30 S, Toyopearl SP and SP sepharose.

Jiang, et al. disclose the use of cation exchange chromatography with a NaCl elution gradient at pH 4.5-6.0 to purifiy a recombinant anti-HER2 monoclonal antibody expressed in glycogenineered *Pichia pastoris* (*Protein Expression and Purification* 76:7 (2011).

The cation exchange chromatography CEX step of the disclosed method is preferably operated in a bind-and-elute mode. The cation exchange chromatography is preferably performed with NaCl elution gradient at pH 4.0. This buffer also contains a stabilizing excipient (Arginine) that allows for successful operation at a lower pH. As shown herein, it has been found that CEX efficiently eliminates Host Cell Protein (HCP), DNA and leached Protein A ligand while retaining TNFR:Fc fusion proteins with high TSA levels. The CEX step of the disclosed method provides an intermediate purification step for the Fc-containing protein. The step is intended to provide the reduction, decrease or elimination, of host cell proteins, Fc-containing protein aggregates and incomplete for fragments of the Fc-containing protein, and to concentrate the Fc-containing protein preparation.

Preferably, the Protein A eluate (PAP) is loaded directly on the cation exchange column. It is preferred that loading is carried out at a pH of at least one unit below the pI of the Fc-fusion protein to be purified. Before loading the fluid comprising an Fc-containing protein onto the cation-exchange resin the pH of the Protein A eluate either adjusted to a pH of less than 5, preferably about 4 or as an alternative diluted with water to a conductivity of less than about 4 mS/cm at about pH 7. Adjustment of pH to about 4 is preferred since it is easily performed by addition of concentrated acetic acid without increasing the load volume significantly. This is essential to allow binding of the Fc-containing protein to the cation-exchange resin.

After loading, the CEX column is washed with preferably a 20 mM to 50 mM phosphate based buffer, which contain arginine at pH 4.0. pH range of 3.5 to 6.0 (i.e pH 3.8) may be used in the presence of protein stabilizing excipients (i.e., arginine, urea) and/or lower temperatures during the step. Acetate based buffers (20-50 mM) may also be used to replace the phosphate based buffers. CEX wash may also employ an intermediate conductivity that is higher than that of the equilibration conditions but lower that elution conductivities i.e., 8 mS/cm, 10 mS/cm, 12 mS/cm.

In the CEX step of the invention, the Fc-containing protein is eluted from the cation exchange resin at a pH about 1 unit below the isoelectric point of the Fc-containing protein using an increasing salt gradient. The elution of the Fc-containing protein may be carried out using any suitable salt e.g. NaCl or KCl. In one embodiment, the increasing salt gradient according to the method of the invention is preferably a shallow NaCl gradient. Preferably, the Fc-containing protein is eluted from the cation exchange resin with an increasing NaCl gradient at a conductivity ranging from about 10 to about 50 mS/cm at a pH of about 3.5 to about 6.0. The conductivity gradient ranging from about 10 to about 60 mS/cm may be generated by increasing the sodium chloride concentration from 0 mM to about 400 mM or 600 mM, or 800 mM or 1000 mM or 1200 mM. The pH is maintained constant during the gradient and may be between 3.5 and 6.0.

Alternatively, an isocratic elution can be performed with buffer at a conductivity and pH that will prevent the elution of aggregates and HCPs. Preferably, the Fc-containing protein is eluted from the cation exchange resin with a step gradient at a conductivity ranging from about 10 to about 50 mS/cm at a pH of about 3.5 to about 6.0. The conductivity isocratic elution ranging from about 10 to about 60 mS/cm may be generated by steping the sodium chloride concentration from to about 400 mM or 600 mM, or 800 mM or 1000 mM or 1200 mM. An increase in pH higher that that used during binding can also be used as an elution step.

It is well known that arginine is effective in suppressing protein aggregation and it is common practice for it to be included at moderate concentration during column chromatography (Arakawa, T et. al., *Protein Expression and Purification* 54:110 (2007). CEX wash and elution buffers also contains a stabilizing excipient (e.g., arginine) that allows for successful operation at a lower pH. Presence of excipients (e.g., arginine, guanidine) at 5 mM to 400 mM in TNFR-FC containing solution lowers the tendency for the protein to aggregate and/or fragment and can in some cases reverse the effect or aggregates or misfolds. In the absence of a stabilizing excipient, unacceptable levels of aggregation may occur during the CEX step.

In accordance with the present invention, cation exchange chromatography can preferably be used for elimination or reduction of contaminant Protein A in the range of 2 to 5 fold.

In addition, the optimized CEX unit operation of the disclosed method of the present invention also reduces the concentration of host cell proteins from the Fc-fusion protein preparation, e.g. in the range of 2 to 5 fold, thus contributing significantly to the host cell protein (HCP) clearance.

Elution of Fc-containing protein is monitored by the absorbance at 280 nm and fractions are collected during the descending phase of the peak of absorbance. Fractions are then pooled so as to avoid aggregates and HCPs in the tail of the peak of elution and enrich TSA levels, this is referred herein as "cutting out of the tail". The tail of the peak of elution may present a distinct shoulder which may preferably be removed from the main peak.

AEX

Anion exchangers can be classified as either weak or strong. The charge group on a weak anion exchanger is a weak base, which becomes de-protonated and, therefore, looses its charge at high pH. DEAE-sepharose is an example of a weak anion exchanger, where the amino group can be positively charged below pH~9 and gradually loses its charge at higher pH values. Diethylaminoethyl (DEAE) or diethyl-(2-hydroxy-propyl)aminoethyl (QAE) have chloride as counter ion, for instance. A strong anion exchanger, on the other hand, contains a strong base, which remains positively charged throughout the pH range normally used for ion exchange chromatography (pH 1-14). Q-sepharose (Q stands for quaternary ammonium) is an example for a strong anion exchanger.

In accordance with the present invention, the eluate from the cation exchange step is then subjected to an anion exchange chromatography which is utilized as the product polishing step in the present invention. In accordance with the present invention, the eluate from the cation exchange step is subjected to an anion exchange chromatography. The anion exchange chromatography may be carried out on any suitable anion exchange resin, such as e.g. weak or strong anion exchangers A column commercially available under the name POROS HQ is an example of an anion exchange resin that is particularly suitable for the AEX unit operation of the present method.

POROS HQ is a polymeric packing resin designed for anion exchange chromatography of peptides, proteins, polynucleotides and other biomolecules It consists of crosslinked poly(styrene-divinylbenzene) flow-through particles with a patented bimodal pore size distribution for very rapid mass transport.POROS HQ media is surface-coated with fully quaternized polyethyleneimine. It is a strong anion exchanger with complete surface ionization over a pH range of 1 to 14.

Typically, the CEX column eluate is diluted or dialysed into an appropriate loading buffer before loading it on the anion exchange column. The anion exchange column equilibrated with the loading buffer. A preferred pH for the loading buffer is one unit above the pI. Suitable pH values range from 6.0 to 8.5. A preferred conductivity for the loading buffer is in the range of 2.0 to 4.6 mS/cm. An appropriate equilibration/loading buffer for use in the disclosed purification process is sodium phosphate at a concentration ranging from 5 to 35, preferably from 20 to 30 mM. A preferred pH for the elution buffer is one unit above the pI. Suitable pH values range from 6.0 to 8.5. A preferred conductivity for the elution buffer is in the range of 7 to 20 mS/cm. An appropriate elution buffer may e.g. be sodium phosphate at a concentration ranging from 5 to 35, preferably from 70 to 200 mM.

The optimized AEX unit operation of the disclosed downstream processing method of the invention further reduces aggregates 1 to 2 fold and host cell proteins 1 to 5 fold.AEX chromatography further enriched TSA levels and removed remaining process residuals. Preferably, the NaCl gradient elution from 0 mM to 100 mM with elution of Fc-containing protein monitored by the absorbance at 280 nm and fractions are collected during the descending phase of the peak of absorbance. Fractions are then pooled so as to avoid aggregates and HCPs. In the tail of the peak cotains enrich TSA levels.

Ultrafiltration

The present purification process of the invention includes, one or more ultrafiltration steps. Ultrafiltration is useful for removal of small organic molecules and salts in the eluates resulting from previous chromatrographic steps, to equilibrate the Fc-fusion protein into a buffer required for the next step of the downstream purification process, or to concentrate the Fc-fusion protein to the desired concentration. Such ultrafiltration may be performed on ultrafiltration membranes, with pore sizes allowing the removal of components having molecular weights below 5, 10, 15, 20, 25, 30 or more kDa.

If the protein purified according to the process of the invention is intended for administration to humans, it is advantageous to include one or more steps of virus removal in the process. In practice, a virus removal filtration step is carried out after the final chromatography step before formulation of the bulk product.

Examples are provided below to further illustrate different features of the present invention. The examples also illustrate useful methodology for practicing the invention. These examples do not limit the claimed invention.

Glossary of Abbreviations
Anion exchange chromatography AEX
Anion exchange product AEXP
Cation exchange chromatography CEX
Cation exchange product CEXP
Capillary isoelectric focusing cIEF
Cell Culture Supernatant CCS
Chinese hamster ovary CHO
Column volume CV
Host cell protein HCP
Microfiltration MF
Microfiltration product MFP
Quenched Protein A product QPAP
Protein A chromatography PrA
Protein A Product PAP
Ultrafiltration-2 UF2
Ultrafiltration-2 product UF2P
Ultrafiltration-4 UF4
Ultrafiltration-4 product UF4P
TSA Total sialic acid

EXAMPLES

Example 1

Optimization of Chromatography Unit Operations

Methods and Materials

Centrate collected from *Pichia* culture fermentation broths containing human TNFR:Fc fusion protein was further clarified by microfiltration an sterile filtered. Filtrate was stored at 4° C. and used as feed for all experiments.

All of the chromatography steps were performed on columns at lab scale using AKTA explorer equipped with UNICORN software. Centrate was fed onto the columns which were subsequently washed. Protein A resin with bound product was subsequently resuspended and the resulting slurry dispensed into the wells of a 96-well filter plate. High throughput methods using GENESIS software on TECAN equipment equipped with a liquid handling arm, a robotic manipulation arm, vacuum filtration, magnetic stirrer and microplate reader with MAGELLAN software were employed to evaluate alternative wash/elution conditions.

Intact, aggregated and misfolded product was detected using analytical HIC butyl column. HCP was detected using UV at 410 nm on a microtiter plate, and monomer content was evaluated using a 3 ml size exclusion column. Accurate titer calculations were made with analytic Protein A columns.

Resins and Buffers

In order to optimize the downstream purification process of the invention, each of the three chromatography steps were optimized individually. Table 28 identifies the resins that were evaluated during the optimization process and also provides a summary of all of the buffers that were evaluated in the high throughput optimization screens used to develop the instant process.

TABLE 28

Protein A Chromatography
Resins

MabSelect Sure
MabSelect
Mab Capture A
Buffers 6 mM Sodium 100 mM NaCl pH 7.2
6 mM Sodium 300 mM NaCl pH 5.0
6 mM Sodium 300 mM NaCl pH 5.5
6 mM Sodium 300 mM NaCl pH 6.0
6 mM Sodium 300 mM NaCl pH 6.5
6 mM Sodium 500 mM NaCl pH 5.0
6 mM Sodium 500 mM NaCl pH 5.5
6 mM Sodium 500 mM NaCl pH 6.0
6 mM Sodium 500 mM NaCl pH 6.5
6 mM Sodium 700 mM NaCl pH 5.0
6 mM Sodium 700 mM NaCl pH 5.5
6 mM Sodium 700 mM NaCl pH 6.0
6 mM Sodium 700 mM NaCl pH 6.5
6 mM Sodium 1000 mM NaCl pH 5.0
6 mM Sodium 1000 mM NaCl pH 5.5
6 mM Sodium 1000 mM NaCl pH 6.0
6 mM Sodium 1000 mM NaCl pH 6.5
100 mM Sodium Citrate 3.5
100 mM Sodium Citrate 3.8
100 mM Sodium Citrate 3.9
100 mM Sodium Citrate 4.0
100 mM Sodium Citrate 4.1
100 mM Sodium Citrate 4.2
100 mM Sodium Citrate 4.3
100 mM Sodium Citrate 4.4
100 mM Sodium Citrate 4.5
100 mM Sodium Citrate 5.0
100 mM Sodium Citrate 5.5
100 mM Sodium Citrate 6.0
50 mM Sodium Citrate 3.8
50 mM Sodium Citrate 3.9
50 mM Sodium Citrate 4.0
50 mM Sodium Citrate 4.1
50 mM Sodium Citrate 4.2
50 mM Sodium Citrate 4.3
50 mM Sodium Citrate 4.4
50 mM Sodium Citrate 4.5
CEX Chromatography
Resins Poros 50 HS
Buffers 25 mM Sodium Phosphate pH 4.5
25 mM Sodium 500 mM NaCl Phosphate pH 4.5
25 mM Sodium 1000 mM NaCl Phosphate pH 4.5
25 mM Sodium Phosphate pH 4.0
25 mM Sodium 500 mM NaCl Phosphate pH 4.0
25 mM Sodium 1000 mM NaCl Phosphate pH 4.0
25 mM Sodium Phosphate, 25 mM Arginine pH 4.0
25 mM Sodium, 25 mM Arginine, 500 mM NaCl Phosphate pH 4.0
25 mM Sodium, 25 mM Arginine 1000 mM NaCl Phosphate pH 4.0
AEX Chromatography
Resins Poros 50 HQ
Capto Adhere
Buffers 25 mM Sodium Phosphate pH 8.0
25 mM Sodium Phosphate pH 4.0

TABLE 28-continued 25 mM Sodium Phosphate pH 7.5
25 mM Sodium Phosphate pH 7.0
25 mM Sodium Phosphate pH 6.5
25 mM Sodium Phosphate pH 6.0
12.5 mM Sodium Phosphate pH 8.0
12.5 mM Sodium Phosphate pH 8.6
12.5 mM Sodium Phosphate 100 mM NaCl pH 8.6
12.5 mM Sodium Phosphate 200 mM NaCl pH 8.6
12.5 mM Sodium Phosphate 100 mM NaCl pH 8.0
12.5 mM Sodium Phosphate 200 mM NaCl pH 8.0

The procedure for quantitation of residual DNA in process samples utilizes the Quant-iT™ PicoGreen® dsDNA kit from Invitrogen™. The Quant-iT™ PicoGreen® dsDNA reagent is a fluorescent dye that selectively binds double-stranded DNA. A standard curve is prepared from the supplied λDNA standard, samples are diluted, the PicoGreen® reagent is added, and the fluorescence is measured at excitation 485 nm, emission 535 nm. The entire assay has been automated on a Tecan workstation.

The method for quantifying residual host cell proteins (HCP) and residual Protein A (leached from chromatography columns) in therapeutic protein process intermediates and final products. The method is an enzyme-linked immunosorbent assay (ELISA) performed in a 96-well microplate. Microplates are coated with anti-HCP or anti-Protein A polyclonal antibodies and then blocked with assay diluent containing 1% BSA and 0.05% polysorbate-20. The calibration curve and samples are then prepared and added to the plate. Following the capture step, biotinylated anti-HCP or anti-Protein A polyclonal antibodies are added to the plate, forming an immune complex. This complex is detected by the addition of streptavidin-alkaline phosohatase (AP) conjugate and the fluorogenic substrate, 4-methylumbelliferyl phosphate (4-MUP). A standard curve is generated by plotting fluorescence intensity vs. the log of concentration. The curve is fit with a four-parameter logistic equation, and unknown sample concentrations are determined by interpolation from the curve. This assay is fully automated on a Tecan workstation.

Enzyme activity (EC50) can be quoted in absolute values as μmol/min. Thus, 1 unit of enzyme activity is the amount of the enzyme which catalyzes the transformation of 1/μmol of substrate per minute. This amount is measured against the reference which has an absolute value of 1 or 100% (Roe, S. ed. *Protein Purification Techniques* $2^{nd}$ ed. 36-38 (2001).

Optimization of Protein A Chromatography

The primary capture step of a downstream processing scheme, if run using parameters which remove impurities at the optimum yield, can significantly decrease the burden on subsequent chromatography steps. Therefore, high throughput screening methods (HTPS) were used to evaluate alternative Protein A resins for their abilities to enrich appropriately folded product, enhance TSA; and their ability to minimize the level of aggregates and reduce the amount of host cell proteins present in the PAP.

MabSelect, MabSelect Sure and Poros MabCapture Capture A perfusion media were evaluated using 20 ml columns. The resin screen protocol utilized 5 CV 25 mM sodium phosphate pH 7.2 as an equilibration buffer, the columns were subsequently washed with the same buffer (wash1, 2 CVs). Resuspended resin with bound protein is dispended into the filter plates and the TECAN is programmed to execute slurry method for wash 2 (3 CVs of equilibration buffer), and elutions using a 50-100 mM Citrate buffer pH 3.4-4.5 (Elution 5 CVs 50-100 mM Citrate pH 3.4-4.5, 5

CVs 100 mM Citrate pH 3.5). Equivalent mass balance on all three resins was achieved.

Filtrate was loaded on each column and purified using the above resin screening protocol. MabSelect sure column provided a poor yield at pH 4 and was eliminated from further consideration. Equivalent mass balance on all three resins was achieved. Poros MabCapture A was observed to provide greater than 2 times higher selectivity in elution of properly folded product compared to MabSelect, thereby achieving a higher purity of quenched Protein A product (QPAP).

Analytical HIC chromatograms revealed the increased selectivity of Poros MabCapture A for properly folded product. TNFR:Fc elutes off a hydrophobic interaction column (HIC) as three distinct peaks termed Fraction #1 (comprising TNFR:Fc fragments), Fraction #2 (comprising properly folded TNFR:Fc) and Fraction #3(comprising misfolded disulfide scrambled TNFR:Fc variants and aggregated protein product) (see FIG. 1). Protein aggregation is a common problem in bioprocessing and can occur during expression, purification or storage. Aggregation is a particular challenge in downstream processes designed for the purification of Fc-fusion preparations which contain high levels of high molecular weight species; and is dependent on experimental variables such as, the amino acid sequence of the protein, the complexity of the protein, temperature, pH, and the type of ion present in a buffer and the buffer's ionic strength.

Fraction #2 is the desired fraction. The data provided in the chromatograms of FIG. 1 illustrate that the QPAP obtained from the Poros MabCapture A resin comprises significantly more (i.e. approximately 40% of the desired product) intact properly folded product in peak #2 than the MabSelect resin which only comprises about 15% of the properly folded product.

In order to further optimize the performance of the Protein A capture step, an additional HTPS experiment using the same reagents and steps outlined above was performed to evaluate the selectivity of Poros MabCapture A using native and refolded media feed as sources of the Fc-fusion protein. The results indicated that the Poros MabCapture A resin continued to exhibit high selectivity for intact properly folded product (i.e., the protein present in peak #2 of the HIC chromatographs), and that the purity and yields of the QPAP was increased almost 2-fold using refolded media feed.

Efficiency of the wash conditions as a function of HCP and DNA clearance was evaluated at different salt concentration at various pH values. The results indicate that HCP removal is mediated by both hydrophobic and electrostatic conditions. In general, better HCP clearance was observed at lower pHs and better DNA clearance was observed at higher wash pHs. Therefore, optimal wash conditions were selected in order to reduce the levels of both HCP and DNA levels. The data suggested that optimum wash conditions require lower pH and mid to low ionic strength based on the ranges explored.

Figure 4A:
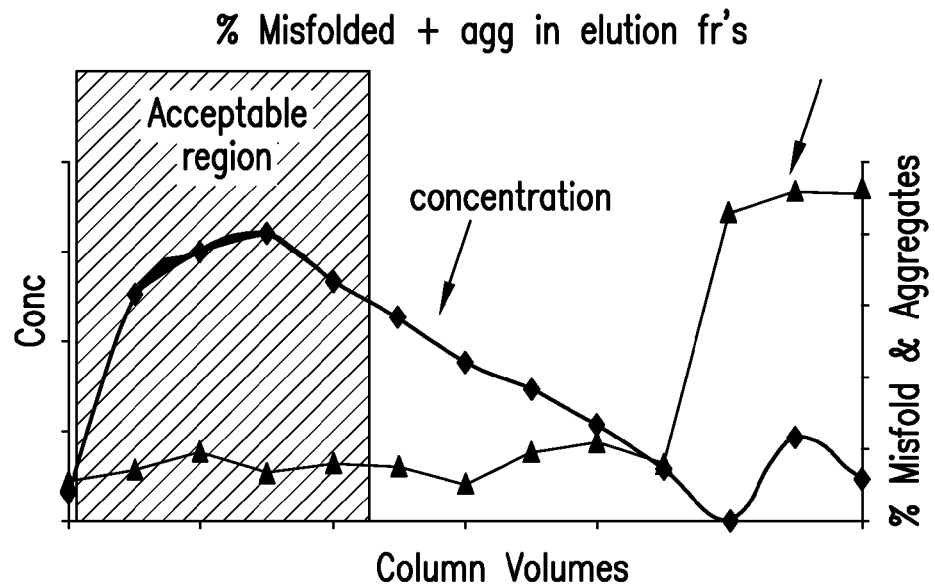
FIG. 4 Development of Protein A elution conditions We observed enrichment of TSA levels, while reducing misfolds and aggregates in the pooled Protein A product.

Elution conditions were also optimized by examining the yield and purity of product and TSA content present in elution fractions as a function of citrate buffer strength (50 mM or 100 mM) and pH (ranging from 3.5 to 4.5). TNFR:Fc was eluted from the Protein A column using a pH gradient. A linear gradient was used so as to further enhance selectivity for resolution of the aggregates and misfolds. Fractions were collected and analyzed before pooling. The data provided in FIG. 4A illustrates that 50 mM Citrate buffer was observed to have a low yield based on recovery across the pH range examined. For 100 mM Citrate buffer, although purity (e.g., peak 2 content) was comparatively high across the pH range examined, yield was notably lower at the low end of the pH range, and appeared to be optimal around pH 4. The lower purity resulted from increasing amounts of peak 3# material in the eluate as pH was decreased below pH 3.8. The levels of aggregates or misfolds in the acceptable fractions was below 1% (i.e. 0.5%-3.0%).

Figure 4B:
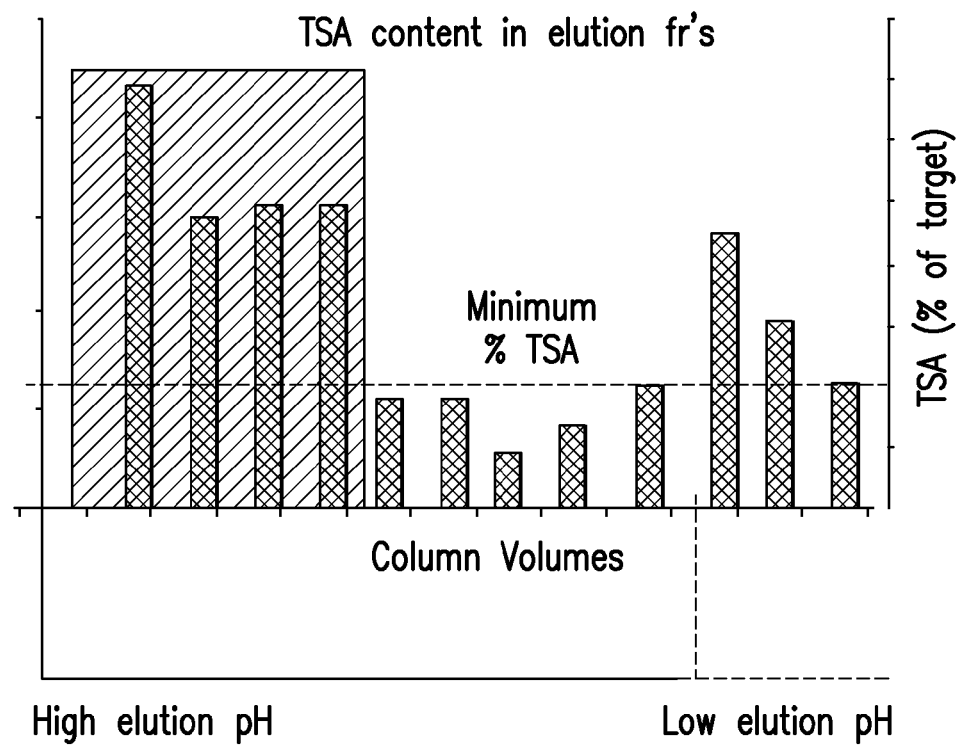

With regard to TSA levels, the earlier eluting fractions had the highest TSA levels. Species with high TSA were generally observed to have lower pI values (FIG. 4B). Therefore, it was determined that in order to maximize purity and yield of correctly folded TNFR:Fc Protein A elution should be perfomed at a higher citrate concentration with an intermediate pH. TSA levels of the Protein A eluate was determined to be similar to the levels calculated for the etanercept reference product.

Optimization of CEX

Cation exchange chromatography (CEX) was used as the first polishing step (after Protein A). The CEX step was optimized using a 20 mL column. The Protein A product, feed to the CEX step, was titrated to pH 4.0 then loaded on the column. Thereafter, the column was washed with 25 mM sodium phosphate, 25 mM arginine, pH 4.0 and elution was carried out in different linear gradient slopes (from 100% 25 mM sodium phosphate, 25 mM arginine, pH 4.0 to 100% 25 mM sodium phosphate, 25 mM arginine, +1M NaCl, pH 4.0 in four different gradient slopes: 10 CV, 20 CV, 30 CV, 40 CV, and 50 CV). Fraction were collected the analyzed. The results demonstrate that optimum selectivity for resolution of fragments, aggregates, and misfolds, with concomitant enhancement of TSA levels was achievable with a 40 CV gradient slope.

Optimization of AEX

Anion exchange chromatography (AEX) was used as the Final polishing step. The AEX step was optimized using a 20 mL column. The CEX product, feed to the AEX step, was buffer exchanged into 12.5 mM Na-Phosphate, pH 6.3 in preparation using a 30 kDa, 2.5 m² regenerated cellulose acetate membrane after which the feed was loaded on the column. Thereafter, the column was washed with 25 mM sodium phosphate, 25 mM arginine, pH 4.0 and elution was carried out in different linear gradient slopes (from 100% 25 mM sodium phosphate, 25 mM arginine, pH 4.0 to 100% 25 mM sodium phosphate, 25 mM arginine, +1M NaCl, pH 4.0 in four different gradient slopes: 10 CV, 20 CV, 30 CV, 40 CV, and 50 CV). Fraction were collected the analyzed.

Example 2

Purification of Recombinant Human TNFR:Fc from Glycoengineered *Pichia Pastoris* Fermentation The primary objectives of this experiment was to demonstrate scale-up of a purification process comprising the above-described unit operations which were optimized using small scale purification experiments and high-throughput screening methods.

In practice, the objectives of Protein A chromatography are enrichment of Total Sialic Acid (TSA), and decrease in aggregates and misfolds in the product. Objectives for the intermediate CEX chromatography step include retaining POI with high TSA levels, while clearing Host Cell Protein (HCP), DNA and leached Protein A ligand. The AEX polishing chromatography step is used to further enrich TSA levels and remove remaining process residuals.

Methods and Materials

Protein A resin—Poros MabCapture A run in bind and elute mode.

Cation exchange resin—POROS HS strong cation exchange adsorbent run in bind and elute mode.

Anion exchange resin—POROS HQ resin run in bind and elute mode.

All buffers were sourced from HyClone® Rapid Response Production Manufacturing, and as required as required salt and concentrated adjust salt and/or pH by were adjusted. In-process protein concentrations were determined via analytical Protein A HPLC (POROS 50A, used with Agilent 1100 series chromatography system) with a response factor 5630 and via UV/VIS post Protein A purification utilizing the extinction coefficient ($\epsilon$) of 1.2.

A. Pre-Harvest Treatment of Fermentation Broth

Fermentation of TNFR:Fc was concluded after 55 hr of methanol induction and adjusted for temperature, cysteine concentration, and pH prior to initiation of centrifugation. The fermentation broth was first cooled to between 4-10° C. using the fermentation reactor's jacketed cooling system. 11 L of 250 mM cysteine hydrochloride monohydrate, pH 8.5, was added to the fermentor to bring the final cysteine concentration in the fermentation broth to 5 mM. The target pH of 8.6 was achieved by the addition of 29 L of 1.5 M Tris, 0.5 M from an initial pH of 6.55. Table 1 summarizes the process parameters for harvest pre-treatment of cell culture.

The pre-harvest treatment of the fermentation broth is designed to provide conditions which favor disulfide isomeriation in order to allow misfolded POI products harvested from the fermentation broth an opportunity to refold correctly, thereby increasing the yield of correctly folded POI. Table 1 summarizes the process parameters for harvest pre-treatment of cell culture.

The optimal operating pH of the pre-harvest treatment was determined to be pH 8.6 (range 8.0 to 9.0). In general, low temperature was observed to be more effective than room temperature treatments, and refolding efficiency was independent of protein concentration. The effective refolding agent tested (including guanidine chloride, arginine, cysteine, and cysteine and cystine) was a combination of cysteine and cystine. In general the bioreactor pH step pretreatment step improved both the yield and the purify of the TNFR:Fc collected from the glycoengineered *Pichia* fermentation.

TABLE 1

| Fermentation broth treatment conditions | |
| --- | --- |
| Fermentation volume (L) | 590 |
| 250 mM Cysteine added (L) | 11 |
| 1.5M Tris, 0.5M Arg added (L) | 29 |
| Total volume after treatment (L) | 630 |
| WCW before treatment | 32.8% |
| WCW after treatment | 31.2% |

B. Centrifugation

The initial primary recovery step employed the use of disc stack centrifugation for the removal of *Pichia pastoris* cellular biomass. The treated cell culture was processed at 0.73 L/min and 9470 RPM using a WESTFALIA CSC-6 continuous disc stack centrifuge. The CSC-6 has a bowl volume of 600 mL with solids holding space of 250 mL. The cell culture was pumped from the bottom outlet of the bioreactor to the centrifuge feed inlet using a peristaltic pump. Centrifugation supernatant was pumped into a chilled holding tank for processing by microfiltration (MF); centrifugation discharge was collected in drums for analysis and disposal. The fermentor was flushed with 25 L of 6 mM sodium phosphate, 100 mM NaCl, pH 8.6 after processing the cell culture through centrifugation to maximize step yield.

Centrifugation operating conditions were optimized during the first 30 minutes of centrifugation to match the turbidity of the disk-stack centrifuge supernatant to that of batch centrifuge supernatant, while maintaining between 70%-80% solids in the centrifugation discharge. The optimized operating conditions were then kept constant for the remainder of the centrifugation step. Table 2 summarizes operating conditions and processing parameters for the centrifugation step.

TABLE 2

| Centrifugation Process Conditions | |
| --- | --- |
| Treated Cell Culture Total Cell Density | 0.312 tc/mL |
| Treated cell culture volume | 602 L |
| Cell Culture Titer | 120 g/L |
| Feed Rate | 0.73 LPM |
| Bowl Speed | 11,730 RPM |
| Flow rate, Q | $1.22 \times 10^{-2}$ m³/sec |
| Q/Sigma | $1.8 \times 10^{-9}$ m/sec |
| Discharge Frequency | 2.5 min |
| Centrate Backpressure | 15-20 psig |
| Centrifugation Results | |
| Processing Time | 12.5 hrs |
| Total # of Discharges | 300 |
| Mass of Discharged Waste | 241 kg |
| Average Offline Centrate Turbidity | 377 NTU |

Figure 5:
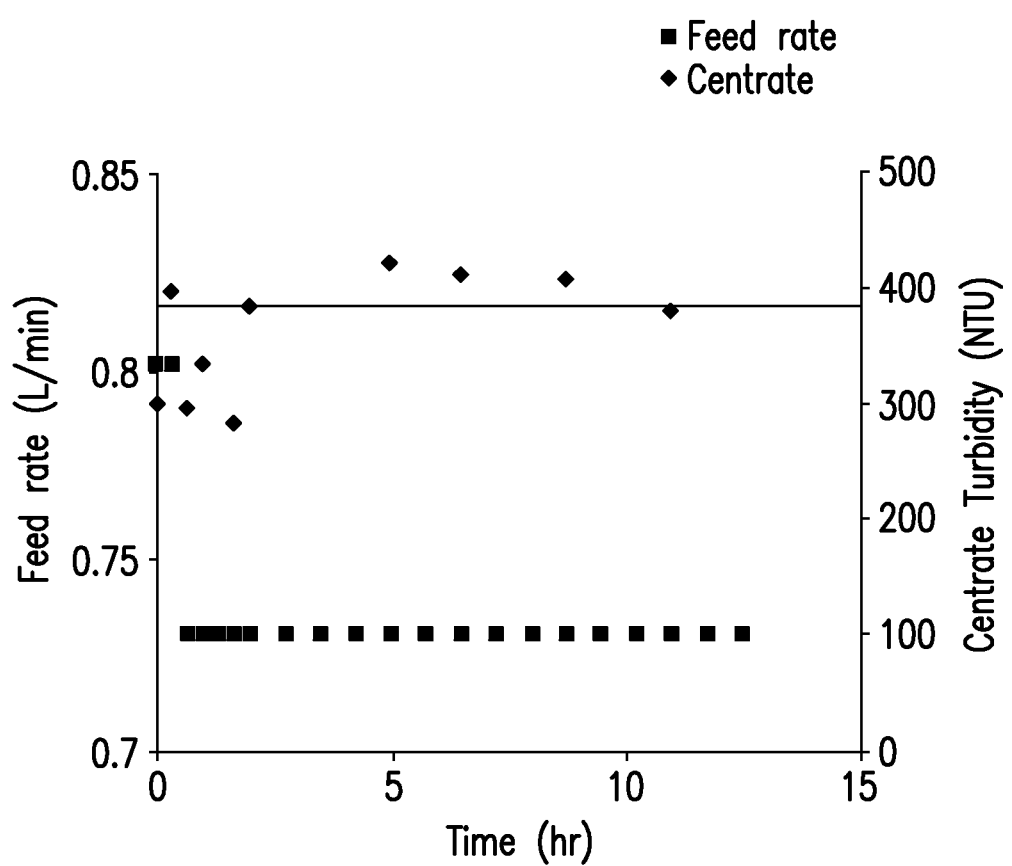
FIG. 5 Feed rate and supernatant turbidity over the course of centrifugation. Solid gray line indicates the supernatant turbidity obtained from batch centrifugation @ 4700 rpm for 20 minutes.

FIG. 5 depicts the turbidity of the disc stack centrifugation supernatant, turbidity of a sample batch centrifugation supernatant, and feed rate into the disc stack centrifuge over the course of centrifugation processing. Supernatant samples were taken every 30 minutes, and were chilled in ice for 30 minutes before measuring turbidity. It is important to note the high turbidity observed for the centrifuge supernatant (~400 NTU). Although this turbidity was significantly higher than previously processed batches (traditionally between 250 and 300 NTU when processed at pH 8.6), it was in close agreement to the turbidity after batch centrifugation (385 NTU). In addition, the turbidity was relatively constant throughout the batch, which suggests that lysis was minimal during centrifugation unit operation. Coupled with the successful loading of greater than 135 L/m2 of centrifugation supernatant onto the MF membrane, the datum suggests that a likely explanation for the high turbidity readings is the presence of lipids or colloids that interfered with the turbidity assay.

C. Microfiltration and Sterile Filtration

The centrifugation supernatant was further clarified using microfiltration. This unit operation, performed at constant permeate flux, utilized a PALL SUPOR regenerated cellulose acetate microfiltration membrane with 0.1 μm cutoff and an area of 2.5 m². A peristaltic pump was used to draw centrifugation supernatant from the holding tank into the membrane. The MF permeate (product) was pumped through a 0.22 um filter for bio-burden reduction, and was stored in 200 L sterile bags at 4° C., whilst the MF retentate was recycled into the holding tank. Microfiltration was initiated after accumulation of approximately 75 L of centrifugation supernatant. With approximately 50 L remaining in the holding tank, constant volume diafiltration ensued and was completed after 3 diavolumes (150 L) of 6 mM sodium phosphate, 100 mM NaCl, pH 8.6. MF was paused between 8-9 hours of operation to allow for the accumulation of additional centrifugation supernatant. Table 3 summarizes the process parameters and results for the microfiltration (MF) and sterile filtration steps.

TABLE 3

| MF/SF Process Conditions | |
| --- | --- |
| MF Filter | 0.1 um regenerated cellulose |
| | 2.5 m2 |
| | Pall Supor |

TABLE 3-continued

| | |
|---|---|
| Sterile Filter | 1.8 m² Sartorius 30" MaxiCap with Sartopore 2 media (cat# 5441307H3SS) Dual layer 0.45/0.2 □m PES membrane |
| Feed Turbidity | ~400 NTU |
| Equilibration/ diafiltration buffer | 6 mM sodium phosphate, 100 mM NaCl, pH 8.6 |
| Feed volume | 440 L |
| Diafiltration volume | 150 L |
| MF/SF Results | |
| Permeate flux | 10-15 LMH |
| MF Yield | 90% |
| TMP | 2-8 psig |
| MF product turbidity | 2-13 NTU |
| MF/SF product volume | 590 L |
| MF loading | 145 L/m2 |
| Total harvest yield | 82% |

Figure 6:
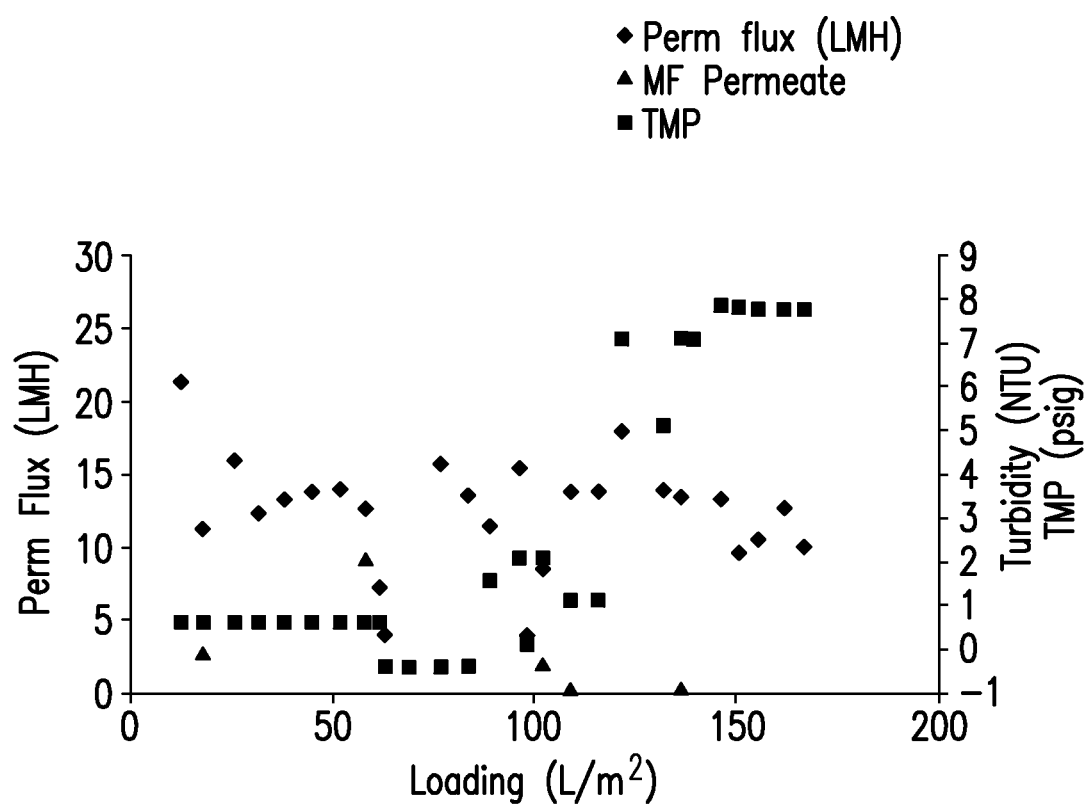
FIG. 6 MF performance as determined by flux and turbidity as a function of loading.

FIG. 6 displays the flux, trans-membrane pressure (TMP) and permeate turbidity over the course of MF. Despite the high turbidity of the centrifugation supernatant, the permeate flux and trans-membrane pressure (TMP) were nearly constant at ~13LMH and 1 psig respectively.

D. Protein A Chromatography

Protein A affinity chromatography was employed as the primary capture step in the purification of TNFR:Fc. The GE BioProcess Skid in FPP (CCS-1444), equipped with UNICORN version 5.2 was utilized for Protein A chromatograhy step. Sterile filtered MF product was loaded on the A 5.2 L column packed in BPG (COL-56-1190-30) 20 cm ID×19.5 cm (BPG 200/500). Elution was based on a linear gradient that incorporates the elution stregths of sodium citrate buffer and a pH gradient ranging from pH 5.0 to 3.5, with 1 CV fractions collected across main product peak.

The pooling stategy for Protein A product collection is based on previous TSA data collected through small scale experiments. As expected, the operating parameters for Protein A resulted in product that was enriched in TSA towards the front of peak, with low levels of misfolds and associated aggregates. Table 4 summarizes the operating conditions and results for the Protein A chromatography step.

TABLE 4

| Protein A conditions | |
|---|---|
| Resin | Poros MabCapture A |
| Packing/Equilibration/ Wash#1/Wash #3/ Flush Buffer | 6 mM Na-phosphate, 100 mM NaCl, pH 7.2 |
| Packing integrity check | 0.5% CV 5M NaCl solution |
| Wash #2 | 25 mM Na-phosphate, 500 mM NaCl, pH 5.5 |
| Product Elution buffer 1A | 50 mM citrate, pH 5.0 |
| Product Elution buffer 1B | 0.1M citrate, pH 4.0 |
| Product Elution buffer 2 | 0.1M citrate, pH 3.5 |
| Regeneration Buffer 2 | 50 mM NaOH, 1M NaCl |
| Quench buffer | 1M Trizmabase (10-20% addition) |
| Equilibration | 5 CV |
| Wash#1 | 2 CV |
| Wash#2 | 5 CV |
| Wash#3 | 3 CV |
| Elution 1A/1B - Gradient | 10 CV |
| Elution 1B | 5 CV |
| Elution 2 | 5 CV |
| Regeneration buffer | 5 CV |
| Product collection | 5 CV (starts at Fraction 2) |
| Packing method | Flow pack |
| Post packing column sanitization/storage | 2CV wash with 20% EtOH in equilibration buffer |

TABLE 4-continued

| | Range | Process Result |
|---|---|---|
| Column Packing[14] | | |
| Column ID (cm) | N/A | 20 |
| Height (cm) | N/A | 16.5 |
| Cross Area (cm2) | N/A | 314 |
| Column Volume (L) | N/A | 5.18 |
| Peak Symmetry | 0.8-1.5 | 1.25 |
| Plates/meter | >1200 | 1599 |
| Packing flow rate (cm/hr)/(L/min) | N/A | 535/2.8 |
| Packing Pressure (psi) | 30-50 | 48.5 |
| Process Parameters | | |
| Load/wash Residence time (min) | ≥6 | 4 |
| Equilibration/Elution/ Regeneration flow rate (cm/hr) | ≤450 | 229 |
| Elution/Regeneration residence time (min) | <6 | 4 |
| Loading (g/L CV) Injection | ≤20 | 9.56 |
| PrA Product collection | 4-6 CV (starts at 100 mAU (A280)) | 4 CV |
| Unquenched product pH Fr. # 2/3/4/5 | 5.0-4.0 | 4.8/4.6/ 4.45/4.4 |
| Quench Buffer Addition (%) Fraction 2/3/4/5 | 10-20 | 4/5/9/13 |
| Quenched product pH | 6.2-7.0 | 6.5/6.2/ 6.3/6.3 |
| Quenched product Conc. (g/L) pool fraction 2/3/4/5 | 1-5 | 1.37 g/L |
| Step Yield (%) | ≥70 | 71.3 |
| Mass Balance (%) | ≥95 | 98.9 |

E. Titration 1

The Protein A affinity chromatography fractions 2-5 were titrated to pH 4.0 before loading onto the next chromatography step. The titration was first performed using 0.5M acetic acid. After adding 10% v/v of titrant, it was changed to 50% glacial acetic acid in DI water in order to increase the acidic strength. Process information for titration 1 is summarized in Table 5.

TABLE 5

| Titration 1 | |
|---|---|
| Volume of pooled fractions | 21.5 L |
| Titrant 1 | 0.5M Acetic acid |
| Titrant 2 | 50% v/v Acetic acid |
| Volume of titrant 1 | 1 L |
| Volume of titrant 2 | 0.65 L |
| final volume | 23.2 L |
| Total M10681 mass | 29.47 g |

The Protein A product (PAP) was observed to be stable for up to a period of 16 hours when stored at the temperature range of 4-8° C. In order to circumvent possible aggregation and protein scrambling that may occur during the process of pH shifting through titration and quenching of the PAP, it is possible to not quench the PAP but rather to load it directly onto the CEX column at pH 4.0.

F. Cation Exchange Chromatography

The second chromatography step utilized cation exchange chromatography (CEX) for intermediate purification. CEX was performed on the CCS-1444 Chromatography System FPP bioprocess skid, using a in BPG (COL-56-1190-30) 20 cm ID×19.5 cm (BPG 200/500) column packed with 5.65 L of POROS HS strong cation exchange adsorbent. The titration 1 product was loaded onto the POROS HS column. The column was washed and eluted in a 40 CV linear ionic strength gradient with fractions collected at one CV intervals. Table 6 summarizes the operating conditions and results for the CEX chromatography step.

TABLE 6

CEX conditions

| | |
|---|---|
| Resin | Poros HS (Lot # HS 250 -396 01382, 01398) |
| Packing Buffer | 6 mM sodium phosphate, 100 mM NaCl, pH 7.2 |
| Packing integrity check | 0.5% CV 5M NaCl solution |
| Buffer A | 25 mM sodium phosphate, 25 mM arginine, pH 4.0 |
| Buffer B | 25 mM sodium Phosphate, 25 mM arginine, 1M NaCl, pH 4.0 |

Process Operation

| Step | Buffer | Volume (CV) |
|---|---|---|
| Pre- Equilibration | Buffer B | 5 |
| Equilibration | Buffer A | ≥8 |
| Wash | Buffer A | 3 |
| Elution | Gradient from 100% buffer A to 60% buffer | 40 |
| Regeneration | Buffer B | 5 |
| Sanitization and Storage | 0.1N NaOH | 3 |

| | Range | Process Result |
|---|---|---|
| Column Packing*Error! Reference source not found.* | | |
| Column ID (cm) | N/A | 20 |
| Height (cm) | N/A | 18 |
| Cross Area (cm2) | N/A | 314 |
| Column Volume (L) | N/A | 5.7 |
| Peak Symmetry | 0.8-1.5 | 1.1 |
| Plates/meter | >1200 | 4785 |
| Packing flow rate (cm/hr)/(L/min) | N/A | 667/3.5 |
| Packing Pressure (psi) | 30-50 | 42 |
| Process Parameters | | |
| Load/wash Residence time (min) | ≥4 | 4 |
| Equilibration/Elution/ Regeneration flow rate (cm/hr) | ≤450 | 267 |
| Elution/Regeneration residence time (min) | <6 | 4 |
| Loading (g/L CV) Injection | ≤10 | 5 |
| CEX Product collection | 10-12 CV (starts at 100 mAU (A280)) | 11 CV |
| Step Yield (%) | ≥75 | 91 |

CEX yield was 91%. This yield and purity improvement should largely be attributed to the optimized Protein A operation, which demonstrated a significant increase in product purity over operations which did not utilize the optimized loading, wash and elution buffers. Although pI values for the CEX fractions do not exhibit significant shifting with increasing ionic strength, the electropherograms in FIG. 7 confirms the premise that the earlier CEXP fractions had more desirable sialic acid patterns.

Figure 7:
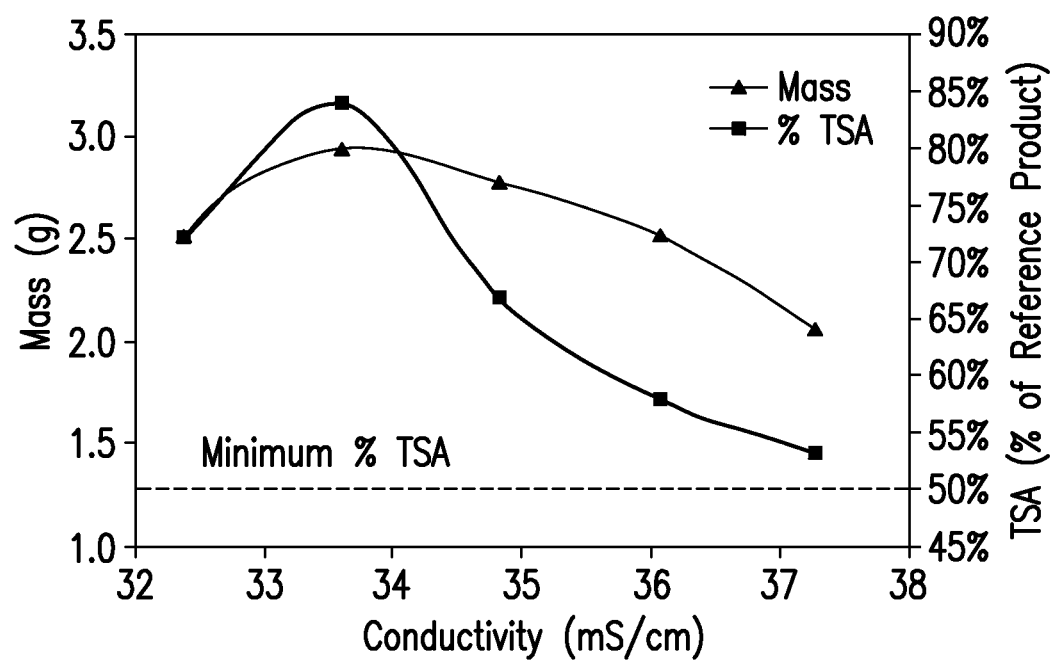
FIG. 7 Reproduction of CEX of Elution profile and corresponding TSA values. TSA values are reported relative to reference compound. Dotted line represents the minimum percent TSA specified for the final product.
Figure 8:
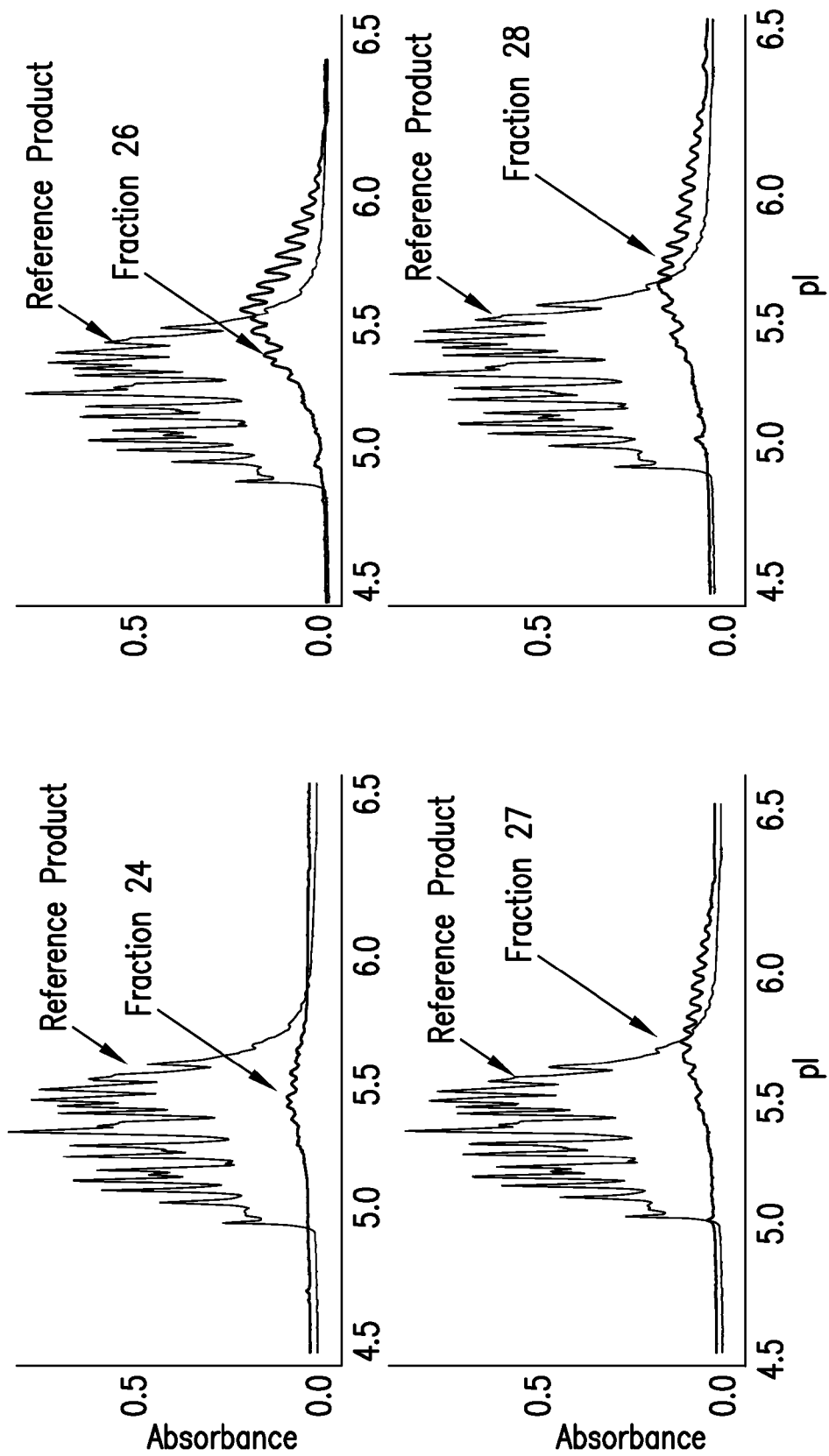
FIG. 8 cIEF electropherograms of CEX fractions across ionic gradient elution.
Figure 9:
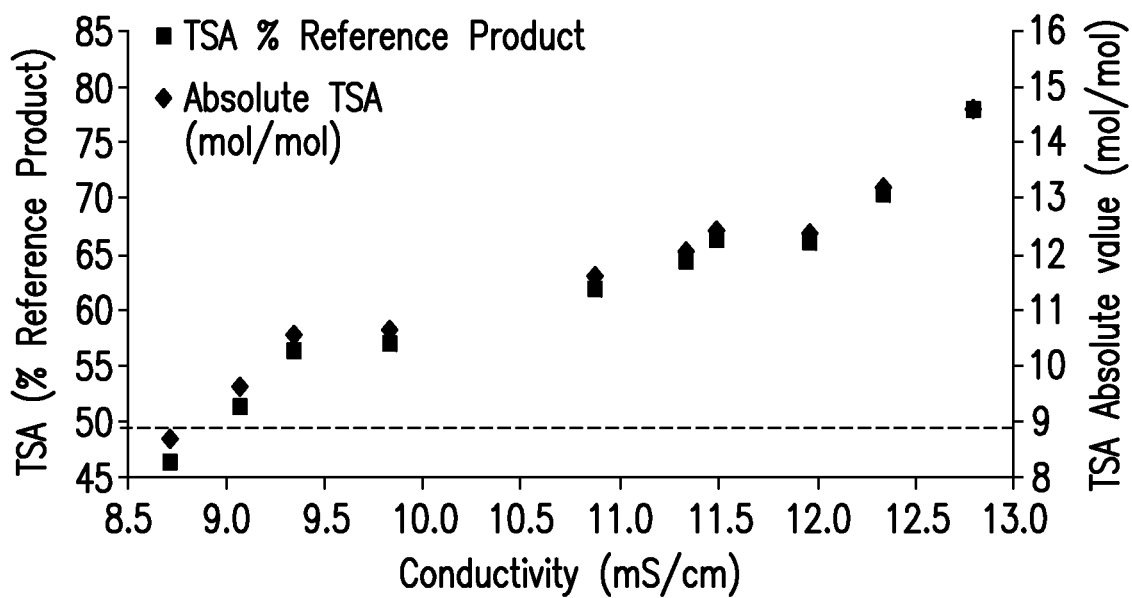
FIG. 9 AEX TSA profile as a function of column conductivity. TSA values are reported relative to reference compound. Dotted line represents the minimum percent TSA specified for the final product.

The TSA levels are shown in FIGS. 7 and 9. The results demonstrate the ability to reduce levels of product fragments, aggregates, and misfolds, as well as exhibiting selectivity for TSA (FIG. 7). The individual CEX product fractions were diluted approximately 2× with 10 mM Tris base, pH 8.0, and then titrated to pH 6.3 with 1M Tris base. The fractions were stored separately at 2-8° C. and pooled after in process determination of product quality attributes.

G. Ultrafiltration 2

The purpose of the Ultrafiltration-2 (UF-2) crossflow filtration step is to concentrate the pooled CEX product to <3 g/L and buffer exchange into 12.5 mM Na-Phosphate, pH 6.3 in preparation for the AEX step. The UF was performed with a 30 kDa, 2.5 m² regenerated cellulose acetate membrane (Pellicon 2 Maxi 30 kDa PLCTK-C) in RY805-208 cold lab. Concentration was operated in fed-batch mode, followed by diafiltration which was performed continuously with 4 diavolumes of 12.5 mM sodium phosphate, pH 6.3. The crossflow rate was maintained by using multiple peristaltic pumps, the retentate backpressure was controlled by a diaphragm valve, and the permeate rate was controlled by a peristaltic pump. Following the diafiltration, the membrane was flushed with buffer to maximize product recovery. Table 7 summarizes the UF-2 operating conditions and process results.

TABLE 7

UF-2 Process Conditions

| | |
|---|---|
| UF-2 Membrane | 2.5 m² Millipore Pellicon 2 PLCTK C Screen membrane 30 kDa regenerated cellulose |
| Pre-conditioning buffer | 12.5 mM sodium phosphate, pH 6.3 |
| Pre-conditioning buffer volume | 20 L/m² |
| Feed Volume | 105.5 L |
| Feed Concentration | 0.222 g/L |
| Target Concentration | 0.666 g/L |
| Diafiltration buffer | 12.5 mM sodium phosphate, pH 6.3 |
| Target Diavolumes | 4 |
| Diafiltration buffer volume | 140 L |
| Recovery buffer volume | 6.47 L |
| Average Crossflow Rate | 3.4 L/min/m² |

UF-2 Results

| | |
|---|---|
| Product Volume (L) | 30 |
| Product pH | 6.3 |
| Product conductivity (mS/cm) | 1.7 |
| Filter Loading | 77 L/m² |
| Average Flux | 34 LMH |
| Average TMP | 4.6 psig |
| Product Concentration | 0.732 g/L |
| Yield | 94% |

H. Titration 2

The UF-2 product was titrated with 0.1 M Trisbase pH 8.0 (1-1.5% v:v UF-2 Product) to pH 8.0 and conductivity <3 mS/cm. Table 8 summarizes titration step performed on the UF-2 Product prior to the AEX injection.

TABLE 8

| Process Parameters | Range | Process Result |
|---|---|---|
| UF-2P after Titration Conductivity (mS/cm) | <3 | 2.3 |
| AEXP after Titration pH Injection 1/2/3 | 7.9-8.1 | 7.99 |
| Added 0.1M Trisbase pH 8.0 | 1-3% | 1% |

I. Anion Exchange Chromatography

The last chromatography step, anion exchange chromatography (AEX), was utilized as the product polishing step. AEX was performed on the CCS-1444 Chromatography System FPP bioprocess skid, using a in BPG (COL-56-1190-30) 20 cm ID×19.5 cm (BPG 200/500) column packed with 5 L of POROS HQ resin. The UF-2 product was loaded onto the POROS HQ column. The column was washed and eluted in a 30 CV linear ionic strength gradient followed by a 10 CV isocratic elution with fractions collected at one CV intervals. Table 9 summarizes the process parameters and results for AEX chromatography step.

TABLE 9

AEX Conditions

| | |
|---|---|
| Resin | Poros HQ |
| Buffer A | 12.5 mM Na-Phosphate, pH 8.0 |
| Buffer B | 12.5 mM Na-Phosphate, 100 mM NaCl, pH 8.0 |
| Packing integrity check | 0.5% CV 5M NaCl solution |

TABLE 9-continued

AEX Process operation

| Step | Buffer | Volume (CV) |
|---|---|---|
| Pre-equilibration | Buffer B | 5 |
| Equilibration/Wash buffer | Buffer A | 9 |
| Elution 1 | Gradient 100% Buffer A to 100% Buffer B | 30 |
| Elution 2 | Gradient 100% Buffer B | 10 |
| Regeneration | 12.5 mM Na-Phosphate, 1M NaCl, pH 7.5 | 5 |
| Regeneration 2/Storage Buffer | 0.1N NaOH | 3 |
| Packing method | Flow pack | |

| | Range | Process Result |
|---|---|---|
| Column Packing[22] | | |
| Column ID (cm) | N/A | 20 |
| Height (cm) | N/A | 16 |
| Cross Area (cm2) | N/A | 314 |
| Column Volume (L) | N/A | 5 |
| Peak Symmetry | 0.8-1.5 | 0.75 |
| Plates/meter | >800 | 1161 |
| Packing flow rate (cm/hr)/(L/min) | N/A | 535/2.8 |
| Packing Pressure (psi) | 25-50 | 48.5 |
| Process Parameters | | |
| Process flow rate (cm/hr) | ≤450 | 230 |
| Loading (g/L CV) | ≤10 | 6 |
| Feed Conductivity (mS/cm) | <3 | 2.3 |
| Feed pH | 7.9-8.1 | 7.99 |
| Product Concentration fraction range | 0.2-0.5 | 0.113-0.217 |
| Step Yield (%) | ≥ | 82 |
| Mass Balance (%) | ≥95 | 98 |

Figure 10:
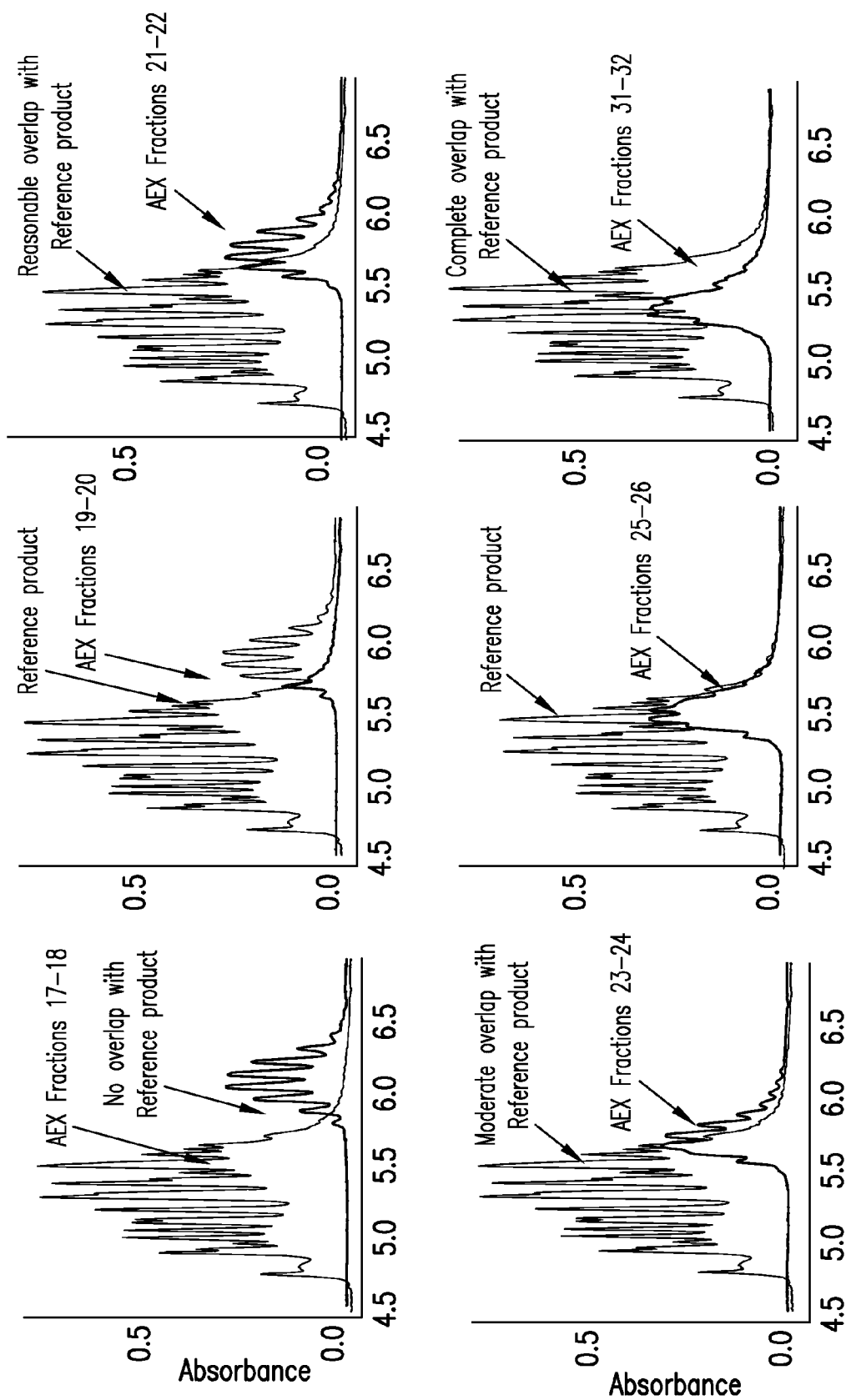
FIG. 10 cIEF electropherograms of AEX fractions across ionic gradient elution.

FIG. 9 illustrates the strong correlation between conductivity and TSA content during elution in the AEX chromatography step. As expected, this dependence is also evident in the relationship between product fraction isoelectric point (pI) and conductivity (FIG. 10).

In comparison to CEX, AEX demonstrated superior capabilities in its enrichment of TSA. The yield for AEX chromatography was 82%, based on the pooling criteria the relied on TSA values. In addition to TSA, improvements were also demonstrated in terms of levels of, aggregates, and misfolds.

J. Formulation and Storage

AEX fractions were stored for a period of 1-3 weeks to allow for the generation of fraction quality attributes (TSA, misfold, fragment, and aggregate levels), as well as decision regarding finalization of the formulation buffer and fraction pooling. To minimize product degradation during this wait period AEX fractions were titrated to pH 6.3, spiked with a 10x formulation buffer, sterile filtered into bags, and stored at 4° C.

K. Ultrafiltration-4 and Formulation

Ultrafiltration 4 (UF-4) was used to formulate the stored and pooled AEX fractions. 3 g of AEXP has been allocated to purification development efforts. A portion of that material was used to execute a small scale experiment was to monitor product quality during the course of the final formulation in a proprietary formulation buffer.

The data suggests that product quality was maintained up to a final concentration of 56 g/L27. 11.8 g of the pooled AEX product was processed during the final UF to support material deliveries and reference standards. UF-4 was performed with a 30 kDa, 0.5 m2 regenerated cellulose acetate membrane (Pellicon 2 Maxi 30 kDa PLCTK-C). The filtration was performed in RY805-208 cold lab. After achieving an intermediate target concentration of 3 g/L, the material was diafiltered into a suitable formulation buffer. The product was then brought to a final concentration of 50 g/L after membrane flushes were performed and combined to maximize product recovery. 1% PS-20 was spiked into the diafiltered product, to achieve a final concentration of 0.01% PS-20. To reduce bioburden, a final 0.2 um sterile filtration is performed. Table 12 summarizes the UF-4 operating conditions and results.

TABLE 10

UF-4 Process Conditions

| | |
|---|---|
| UF4 Membrane | 0.5 m² Millipore Pellicon 2 PLCTK C Screen membrane (cat#) 30 kDa regenerated cellulose |
| Pre-conditioning buffer volume | 10 L |
| Feed Volume | 55.9 L |
| Feed Concentration | 0.211 g/L |
| Target Concentration | 50 g/L |
| Target Diavolumes | 5 |
| Diafiltration buffer volume | 20 L |
| UF-4 Results | |
| Product Volume | 236 mL |
| Product Concentration | 50 g/L |
| Yield | 92 |

Summary

Figure 11:
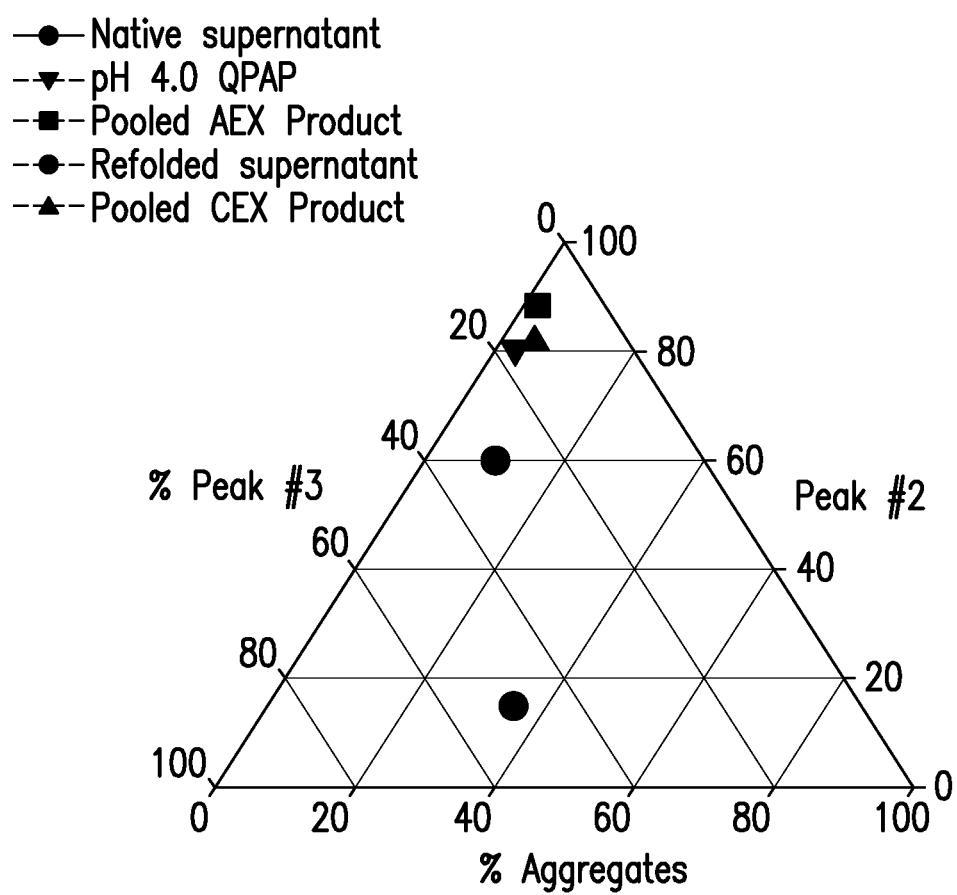
FIG. 11 Impurity clearance in the course of M0010681 purification.
Figure 12:
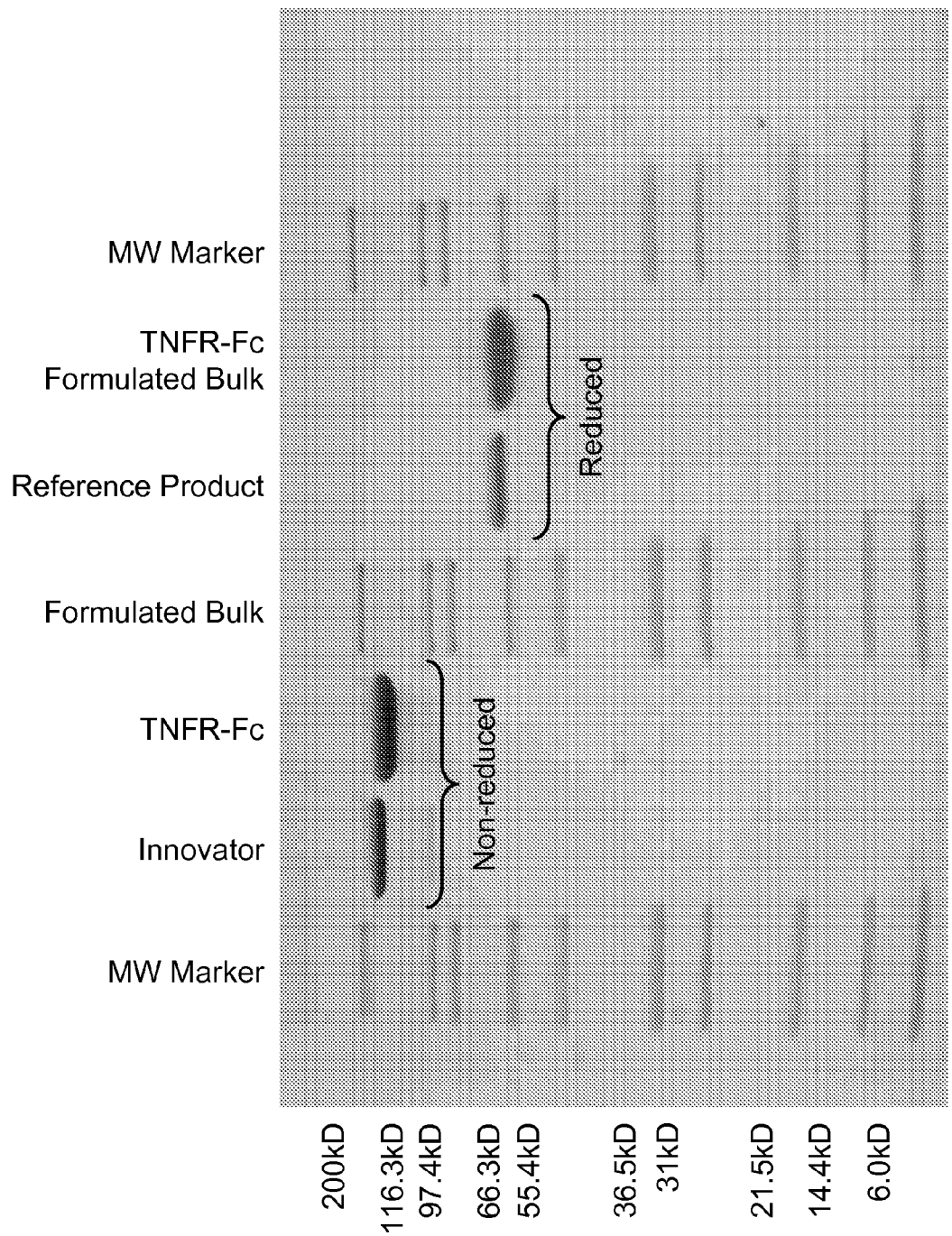
FIG. 12 SDS PAGE analysis of final formulated Bulk.

The ternary plot provided in FIG. 11 summarizes the course of impurity clearance throughout the purification process. Refolding improves productivity, by increasing the level of properly folded (peak #2) while decreasing misfolds (peak #3) and aggregate. Optimized Protein A condition allows for purity enhancement, thus decreasing the burden on subsequent CEX and AEX chromatography of this requirement. Although FIG. 11 depicts a modest increase in the level of purity between CEX and AEX product, a process that includes three chromatography modalities provides greater level of clearance of process residuals, thus increasing overall process robustness. Analytical results summarizing the purity of the process streams and final formulated bulk product are summarized in the Table 11 and the SDS PAGE in comparison to the reference product is represented in FIG. 12.

The overall yield through purification was 33%, resulting in 18 g of purified product. Step yields and concentrations are summarized in Table 12.

TABLE 11

| Process Stream ID | TNFR:Fc (g/L) | DNA (ppm) | DNA Rejection Factor | HCP (ppm) | HCP Rejection Factor | Protein A (ppm) | Protein A Rejection Factor | TSA (%) | Aggregates (%) | Misfold (%) |
|---|---|---|---|---|---|---|---|---|---|---|
| MFP | 0.560 | 1437 | NA | 8.9E+05 | NA | NA | NA | NA | NA | NA |
| QPAP | 1.4 | <3 | >479 | 790 | 1127 | 1025 | NA | 62 | 3.0 | 11 |
| CEXP/UF-2 | 0.67 | <3 | >1 | 303 | 2.6 | 497 | 2.1 | 62 | 3.0 | 8 |
| AEXP/UF-4 | 50 | 0.25 | >12 | 93 | 3.3 | 3 | 166 | 75 | 1.4 | 11 |

TABLE 12

| Product Stream | Volume (L) | TNFR:Fc Mass (g) | StepYield (%) | Target Yield (%) |
|---|---|---|---|---|
| Feed | 590 | 49.7 | — | — |
| Harvest product | 590 | 40.8 | — | — |
| QPAP | 23.4 | 28.9 | 71% | 70 |
| CEX | 105 | 24.3 | 84% | 80 |
| UF-2 | 30 | 22.8 | 94% | 90 |
| AEX | 77 | 18.7 | 82% | 80 |
| UF-4/BRF | 0.301 | 16.9 | 90% | 90 |
| Total | | 16.9 | 33 (57%**) | |

Example 3

Purification of TNFR:Fc from Cho Cell Culture Supernatant (CCS)

Materials and Methods:

The CCS used in the experiment, described herein, was produced using two different CHO cell lines (23D8 and 18G10). TNFR:Fc was purified from each culture separately, according to the downstream process flow scheme as outlined in FIG. 2. Briefly the downstream process involves a Protein A primary recovery step, a CEX intermediate purification step, at least one ultrafiltration step, an AEX polishing step, and a final formulation step.

A. Primary Recovery and Refolding

The CCS was refolded to convert misfolded and aggregated species to correctly folded monomer. The refolding conditions used were those developed for *Pichia*-expressed TNFR:Fc in which the broth was cooled to <10° C., cysteine added for a final concentration of 5 mM, and pH adjusted to 8.6 using 1.0M Trizmabase plus 0.5M arginine. The refolding and titration were done at <10° C., to minimize the effect of temperature on pH. The volume and titers of the delivered cell broth are summarized in Table 13.

TABLE 13

| Clone | Vol (L) | WCW | Titer (g/L) | Mass (g) |
|---|---|---|---|---|
| 23D8 | 25 | 2% | 0.35 | 8.7 |
| 18G10 | 24 | 1% | 0.34 | 17.0 |
|  | 25 | 1% | 0.36 |  |

Clarification was done by MF, rather than centrifugation and depth filtration, for simplicity. During later scale-up batches, we would have examined the use of a disc-stack centrifuge and depth filters for primary recovery. MF was performed using a Pall Centramate II membrane with 0.65 um pore size. The retentate feed volume was reduced to $\frac{1}{10}^{th}$ of its starting volume, and diafiltered 3×. The permeate turbidity was measured to be ~10NTU before being passed through a 0.22 um sterile filter, and held for >16 hrs at 4° C. for refolding.

CCS samples were analyzed to compare the effects of refolding and pH titration on the yield of correctly folded TNFR:Fc (i.e., peak #2 from a QPAP HIC analysis) recovered from native and pre-treated supernatant. Analysis consisted of loading feed onto a Poros MabCapture A column, & following a procedure that is outlined in Table 14.

The data presented in Table 14 for clone 18G10 (which is representative of the data obtained for clone 23D8) indicate that the pH titrated and refolded CCS had a slightly higher yield across Protein A, and significantly higher Peak2 content in the quenched Protein A product (QPAP). Table 14 presents data obtained from QPAP using HP-HIC and HP-SEC.

TABLE 14

| Sample | HP-PrA QPAP (pH 4.0) conc (g/L) | HP-HIC on QPAP (pH 4.0) | | | HP-SEC on QPAP (pH 4.0) | | |
|---|---|---|---|---|---|---|---|
| | | % Peak1 | % Peak2 | % Peak3 | % Agg | % Monomer | % Clip |
| 18G10-unadjusted | 0.53 | 2% | 61% | 38% | 1% | 99% | 0% |
| 18G10-adjusted | 0.60 | 2% | 91% | 8% | 0% | 100% | 0% |

B. Protein A Chromatography

Protein A affinity chromatography was employed as the primary capture step in the purification of CHO-expressed TNFR:Fc, using the operating conditions elucidated above for *Pichia*-expressed TNFR:Fc.

Refolded MFP was loaded onto a Protein A column. Processing conditions are summarized in Table 15. A single injection was performed for each clone, with loading at ≤10 g/L column volume (CV). The residence time was 5.3 min, which was the lowest residence time possible due to the flowrate limitation of the system. Loading was followed by 3 washes to remove product fragments and impurities. No loss of POI was detected in the washes or flowthrough.

Elution was performed with a gradient over 10 CV from 50 mM Na-citrate, pH 5.0 to 100 mM Na-citrate, pH 4.0, followed by a 5 CV hold at 100 mM Na-citrate, pH 4.0. Fractions were left unquenched overnight, because prior data showed that PrA product was stable for at least 10 days without quenching. During elution, fractions of 1 CV were collected and analyzed by HP-PrA, BP-HIC, and HP-SEC, to determine protein concentration, and percentages of Peaks 1-3, aggregates, and clips.

TABLE 15

| Step | Buffer | Column volume (CV) |
|---|---|---|
| Equi | 6 mM NaPi, 100 mM NaCl, pH 7.2 | 5 |
| Load | Feed | — |
| Wash1 | 6 mM NaPi, 100 mM NaCl, pH 7.2 | 2 |
| Wash2 | 6 mM NaPi, 500 mM NaCl, pH 5.5 | 5 |
| Wash3 | 6 mM NaPi, 100 mM NaCl, pH 7.2 | 3 |
| Elution1 | 50 mM Na-Citrate, pH 5.0 --> 100 mM Na-Citrate, pH 4.0, collect 1CV fractions | 10 |
| Elution2 | 100 mM Na-Citrate, pH 4.0, collect 1CV fractions | 5 |
| Regen | 50 mM NaOH + 1M NaCl | 4 |
| Flush | 6 mM NaPi, 100 mM NaCl, pH 7.2 | 3 |
| Storage | 20% EtOH in Equi buffer | 2 |

Figure 13B:
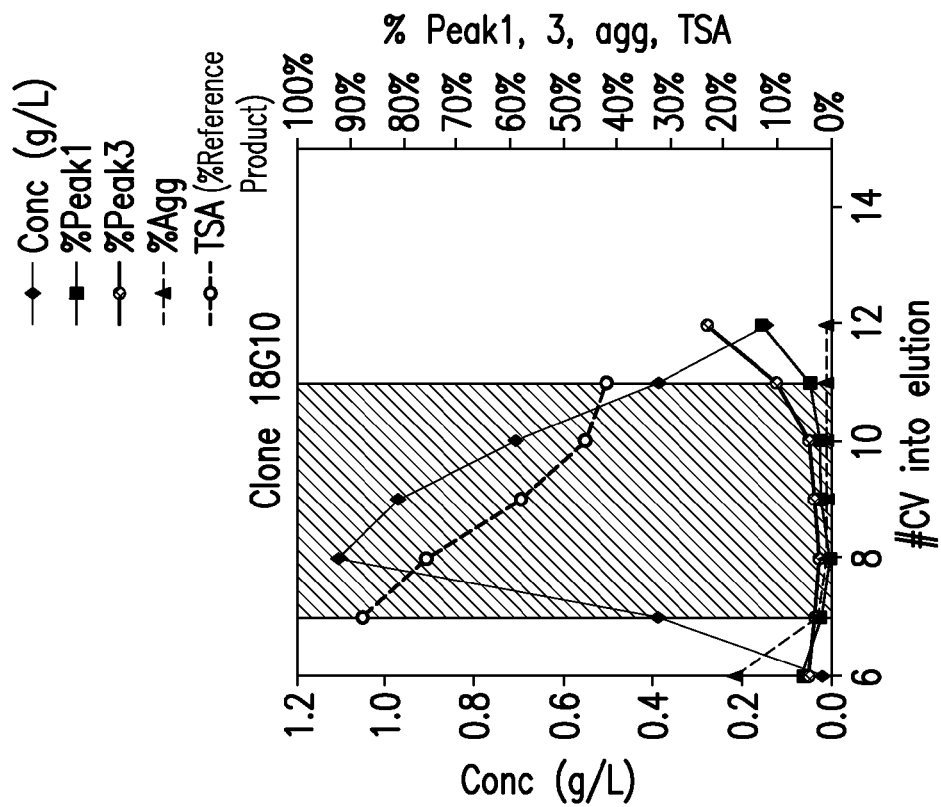
FIG. 13 Eluate product profiles of two clones in CHO cell line during Protein A chromatography.
Figure 13A:
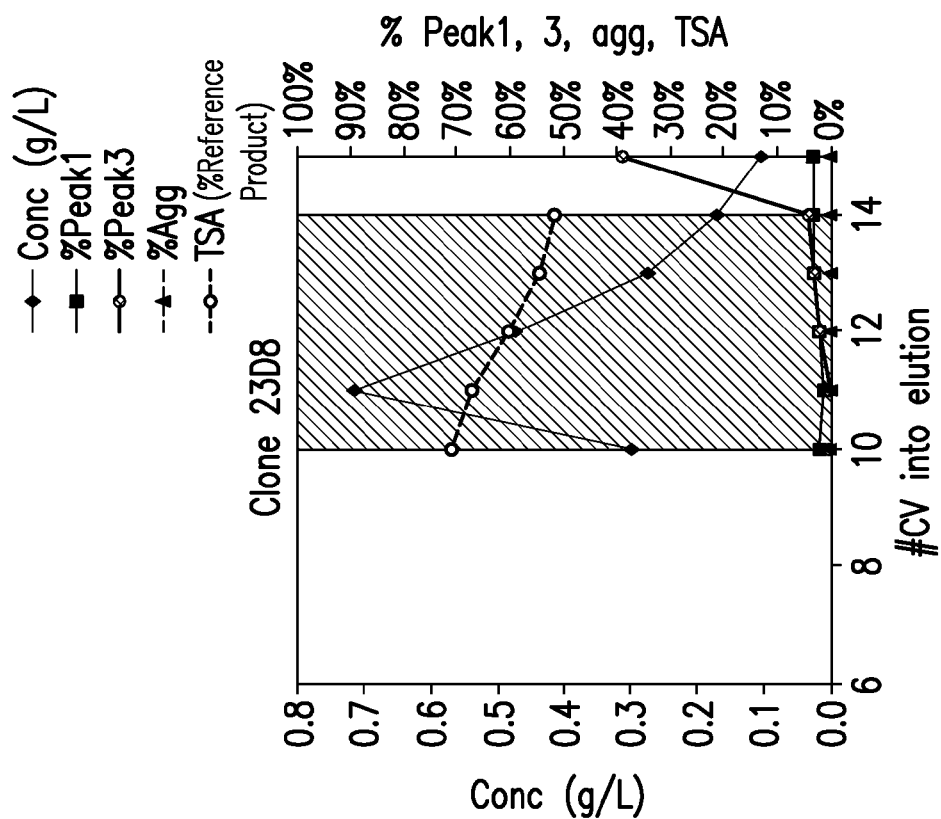

PrA fractions with high Peak#2 percentage and monomer content were pooled for further processing. The elution profile for CHO cell clones 18G10 and 23D8 is shown in FIG. 13. Clone 23D8 eluted between 10-15 CVs after the start of elution. All fractions were pooled for further processing, with the exception of fraction #15, which had high Peak #3 content. Clone 18G10 eluted earlier than 23D8, between 6-12 CVs after the start of elution. All fractions except for #6 and 12 were pooled for further processing, due to their low product content, and comparatively high Peak #3 content.
Yield and product quality are summarized in Table 16. Clone 23D8 had significantly higher yield during PrA than clone 18G10.

TABLE 16

| Clone | | 23D8 | 18G10 |
|---|---|---|---|
| Pooled PAP fr's (#CV into elution) | | 10-14 | 7-11 |
| % Yield | | 70% | 56% |
| % MB | | 82% | 95% |
| Pooled PAP TSA (% innovator lot 1011803) | | 53% | 60% |
| Pooled PAP Normalized EC50 | | 1.07 | 0.96 |
| HP-SEC on Pooled PAP | % Agg | 0% | 0% |
| | % Monomer | 100% | 100% |
| HP-HIC on Pooled PAP | % Peak1 | 4% | 1% |
| | % Peak2 | 94% | 96% |
| | % Peak3 | 2% | 3% |
| Residuals for Pooled PAP (ng/mL) | HCP | <27 | <25 |
| | PrA ligand | TBD | TBD |
| | DNA | <3.8 | <3.8 |

Figure 14:
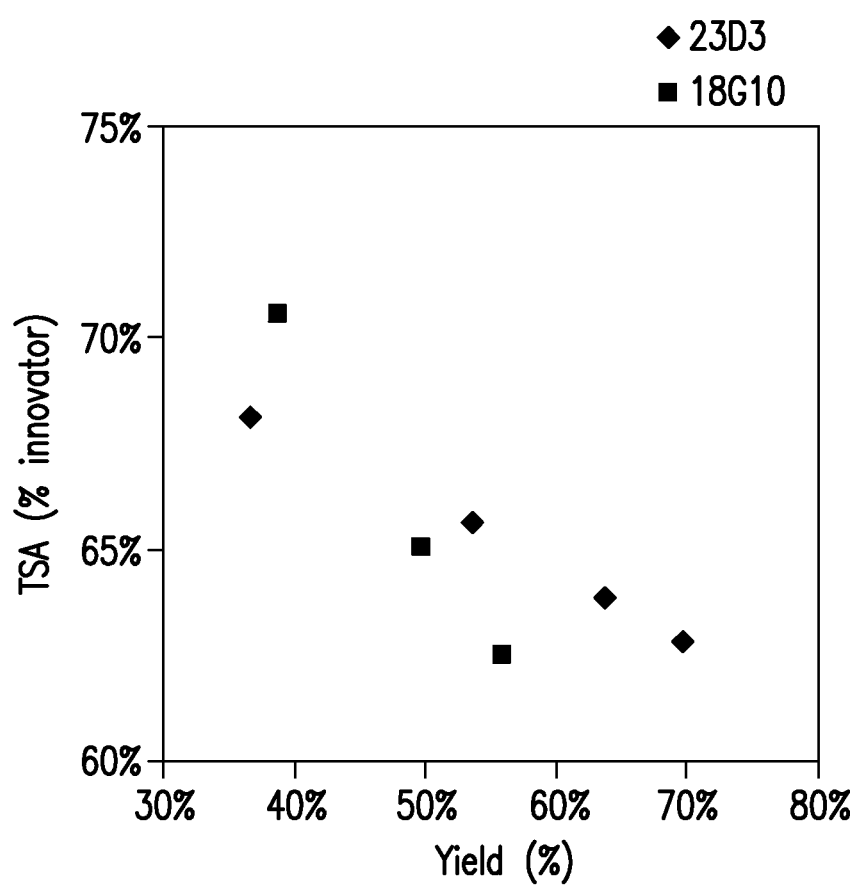
FIG. 14 TSA levels of pooled Protein A fractions as a function of yield. TSA values are reported relative to reference compound.

Fractions with high Peak2 and monomer content were pooled for further purification. Samples were also analyzed for TSA content, cIEF profile, EC50, and impurities. For both clones, earlier eluting fractions were enriched in TSA (FIG. 13). As later fractions were pooled, TSA decreased as yield increased (FIG. 14). TSA values are reported as a percentage of the TSA content of reference product ENBREL® lot 1011803. It appears that a better balance between yield and TSA was attained for clone 23D8 than 18G10.

Figure 15A:
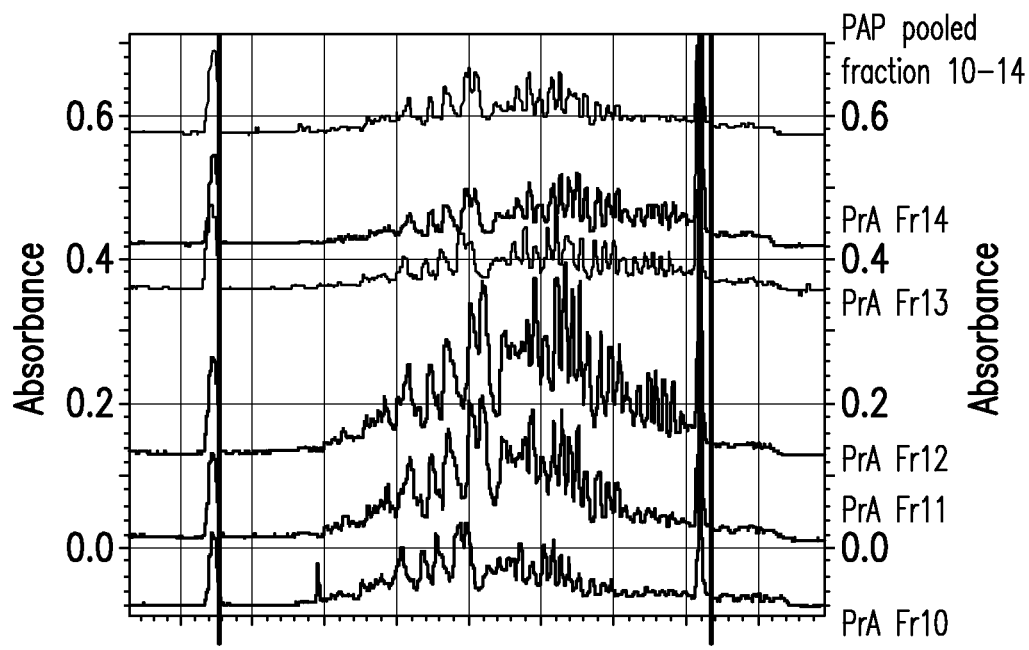
FIG. 15 cIEF profile for Protein A eluate fractions from CHO cell line clone 18G10 as compared to reference compound.
Figure 15B:
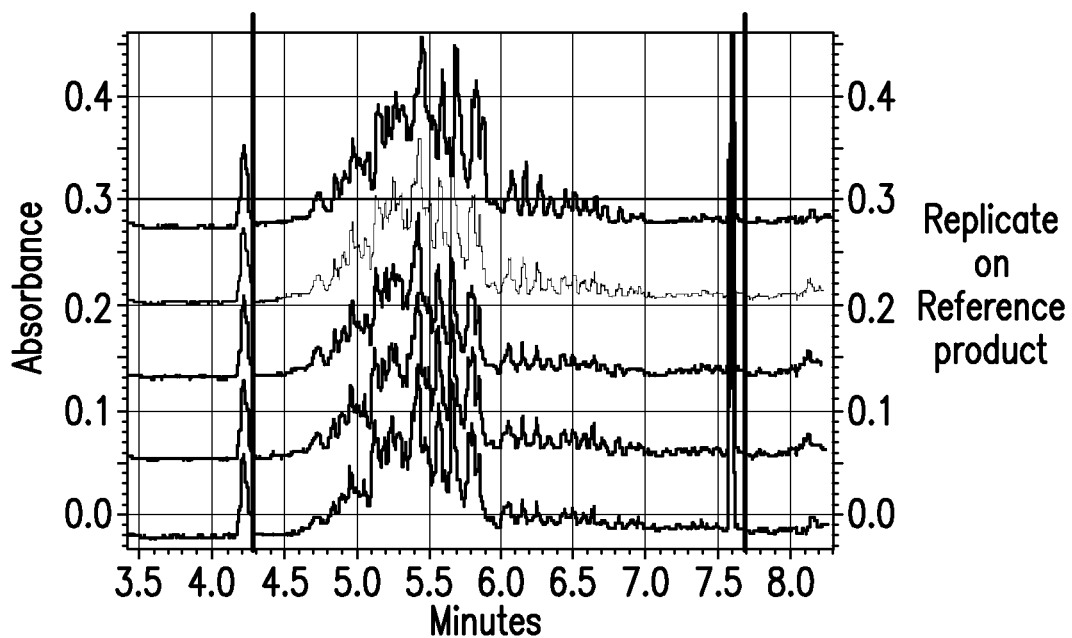
Figure 16:
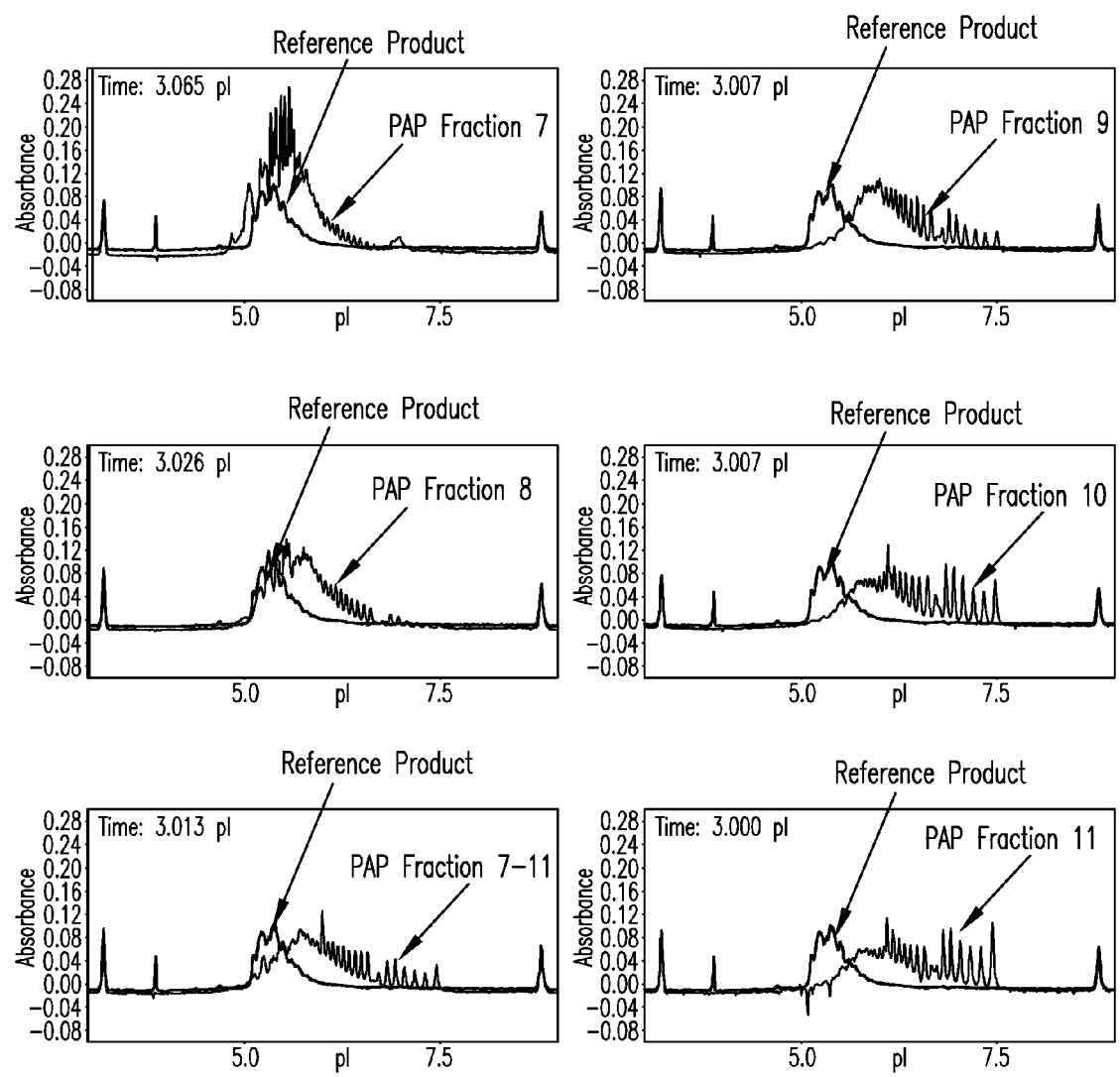
FIG. 16 cIEF profile for Protein A eluate fractions from CHO cell line clone 23D8 as compared to reference compound.

For both clones, earlier eluting PrA fractions are more acidic and have cIEF profiles that overlap well with the reference product compared to later fractions (FIG. 15 and FIG. 16). FIG. 15A compares cIEF profile for PAP fractions from clone 18G10 of fractions 10 to 14 and a pooled sample. FIG. 15 B display replicate cIEF profiles for samples of the reference product (etanercpet) for comparison. FIG. 16 provide cIEF profiles comparing a single PAP fraction from clone 23D8 to the cIEF profile of the reference product (i.e., ENBREL® lot 1011803).

For both clones, the PAP fractions contained host cell protein (HCP) and DNA impurities below the limit of detection when measured by an ELISA assay for CHO HCP and a picogreen assay for DNA. Both contained leached PrA ligand on the order of hundreds of ng/mL when detected by an ELISA assay for the ligand (Table 17). Clone 23D8 was observed to have higher levels of the contaminant PrA, this is most likely attributed to the lower pH needed to elute it from the PrA column.

TABLE 17

| Clone | Sample | HCP (ng/mL) | PrA ligand (ng/mL) | DNA (ng/mL) |
|---|---|---|---|---|
| 23D8 | MFP | 22124 | | 3264 |
| | PrA Fr11 | <26 | 193 | <3.8 |
| | PrA Fr12 | <26 | 154 | |
| | PrA Fr13 | <27 | 188 | <3.8 |
| | PrA Fr15 | <27 | 152 | <3.8 |

TABLE 17-continued

| Clone | Sample | HCP (ng/mL) | PrA ligand (ng/mL) | DNA (ng/mL) |
|---|---|---|---|---|
| 18G10 | MFP | | | 33907 |
| | PrA Fr7 | <26 | 24 | <9.5 |
| | PrA Fr8 | <26 | 15 | <3.8 |
| | PrA Fr9 | <26 | 482 | <3.8 |
| | PrA Fr10 | <25 | 450 | <3.8 |
| | PrA Fr11 | <25 | 45 | <3.8 |
| | Pooled PAP | <25 | 30 | <3.8 |

Table 18 summarizes the normalized EC50 values for the PAP fractions. The normalized EC50 result of pooled PAP fractions for clone 23D8 was 1.07, which was slightly higher than that of 18G10, which was 0.96. No trend was apparent with the fraction number, with all fractions having values ~1.

TABLE 18

| Clone | Sample | Normalized EC50 |
|---|---|---|
| 23D8 | PrA Fr10 | 0.94 |
| | PrA Fr11 | 1.09 |
| | PrA Fr12 | 1.15 |
| | PrA Fr13 | 1.30 |
| | PrA Fr14 | 0.93 |
| | Pooled PAP | 1.07 |
| 18G10 | PrA Fr7 | 0.97 |
| | PrA Fr8 | 1.10 |
| | PrA Fr9 | 1.04 |
| | PrA Fr10 | 0.96 |
| | PrA Fr11 | 0.77 |
| | Pooled PAP | 0.96 |

C. Cation Exchange Chromatography

CEX was performed on pooled PrA products to further enrich the content of TSA, Peak2, and monomer, and clear residual impurities. Processing conditions are summarized below.

TABLE 19

| Feed | Pooled PrA product fr's |
|---|---|
| Resin | Poros 50 HS |
| Col loading (g/L CV) | ≤15 |
| Residence time (min) | ≥4 |

| Step | Buffer | Column Volume (CV) |
|---|---|---|
| Sanitize | 0.1N NaOH | 1 |
| Pre-equi | 25 mM NaPi, 25 mM Arg, 1M NaCl, pH 4.0 | 2 |
| Equi | 25 mM NaPi, 25 mM Arg, pH 4.0 | 8 |
| Load | Feed | — |
| Wash | 25 mM NaPi, 25 mM Arg, pH 4.0 | 2 |
| Elution | 25 mM NaPi, 25 mM Arg, pH 4.0, 0.25M --> 0.65M NaCl, collect 1CV fractions | 20 |
| Salt strip | 25 mM NaPi, 25 mM Arg, 1M NaCl, pH 4.0 | 3 |
| Storage | 0.1N NaOH | 3 |

Loading was ≤15 g/L CV, which was the loading generally used for *Pichia* feed. A single injection was done for 23D8 feed, & two injections were done for 18G10 feed to remain below the loading limit. CEX was performed at pH 4.0, with elution by a 20 CV linear gradient from 0.25-0.65M NaCl. Product was collected in 1 CV fractions that were then analyzed by HP-PrA, HP-HIC, and HP-SEC. Those with high Peak2 and monomer content were pooled for further processing. Fractions were also later analyzed for TSA, cIEF profile, EC50, and residual impurities.

Figure 17B:
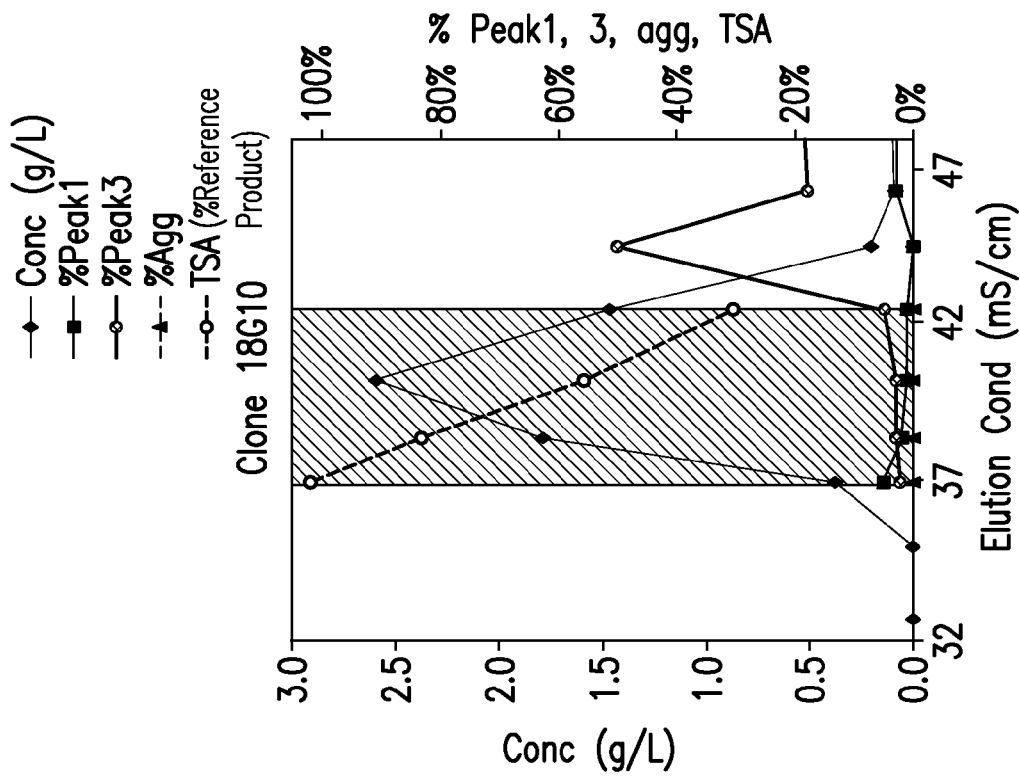
FIG. 17 Eluate product profiles of two clones in CHO cell line during CEX chromatography.
Figure 17A:
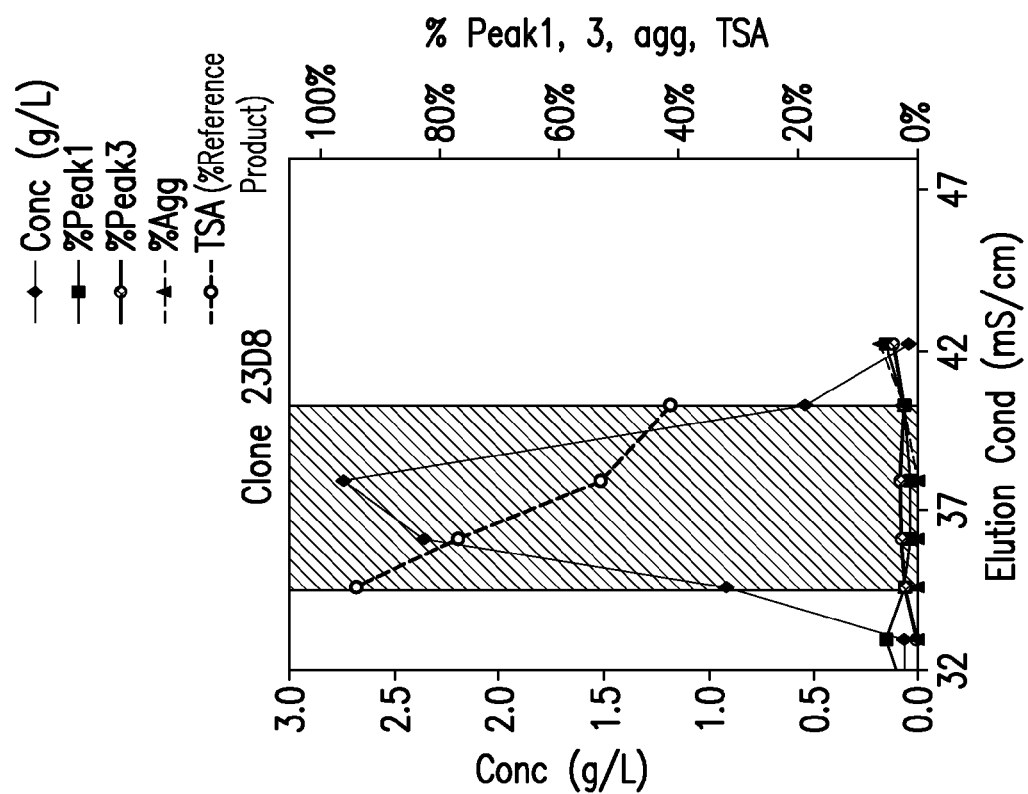

The elution profile for the two clones is shown in FIG. 17 (23D8 Panel A, 18G10, Panel B). For clone 23D8, the bulk of the elution peak was between 35-40 mS/cm. There was also a small peak at the very start of elution. Since all product fractions had high Peak2 and monomer content, all were pooled. The bulk of clone 18G10 eluted between 37-45 mS/cm, with a small peak at the very beginning of elution. Product that eluted between 37-42 mS/cm was pooled for further processing. The two injections performed for 18G10 had identical profiles, indicating that CEX performance is reproducible. The data in Table 20 summarizes Yield and product quality.

TABLE 20

| Clone | | 23D8 | 18G10 |
|---|---|---|---|
| Cond of pooled CEXP fr's (mS/cm) | | 35-40 | 37-43 |
| % Yield | | 98% | 89% |
| % MB | | 99% | 99% |
| Pooled CEXP TSA (% innovator lot 1011803) | | 70% | 61% |
| Pooled CEXP Normalized EC50 | | 1.07 | 1.01 |
| HP-SEC on Pooled CEXP | % Agg | 1% | 1% |
| | % Monomer | 99% | 99% |
| HP-HIC on Pooled CEXP | % Peak1 | 2% | 4% |
| | % Peak2 | 96% | 93% |
| | % Peak3 | 2% | 3% |
| Residuals for Pooled CEXP (ng/mL) | HCP | <26 | <24 |
| | PrA ligand | TBD | 28 |
| | DNA | <3.8 | <3.8 |

Figure 18:
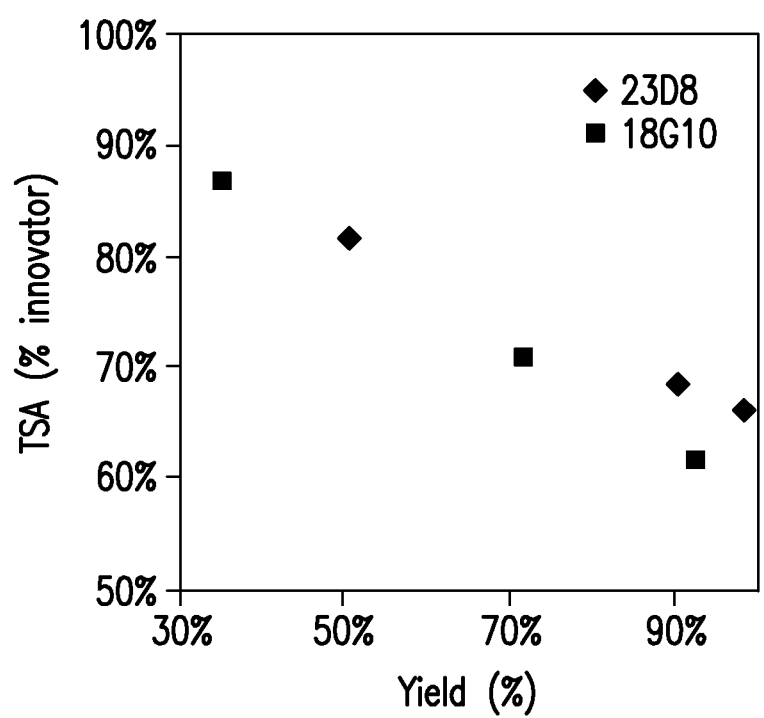
FIG. 18 TSA levels of pooled CEX fractions as a function of yield. TSA values are reported relative to reference compound.

For both clones, TSA decreased with increasing elution conductivity. FIG. 18 illustrates that as later eluting fractions were pooled, TSA decreased as yield increased. TSA is expressed as a percentage of sialic acid present in the reference product (ENBREL® lot 1011803). During CEX, higher yields and TSA values were attained for clone 23D8 than 18G10.

Figure 19A:
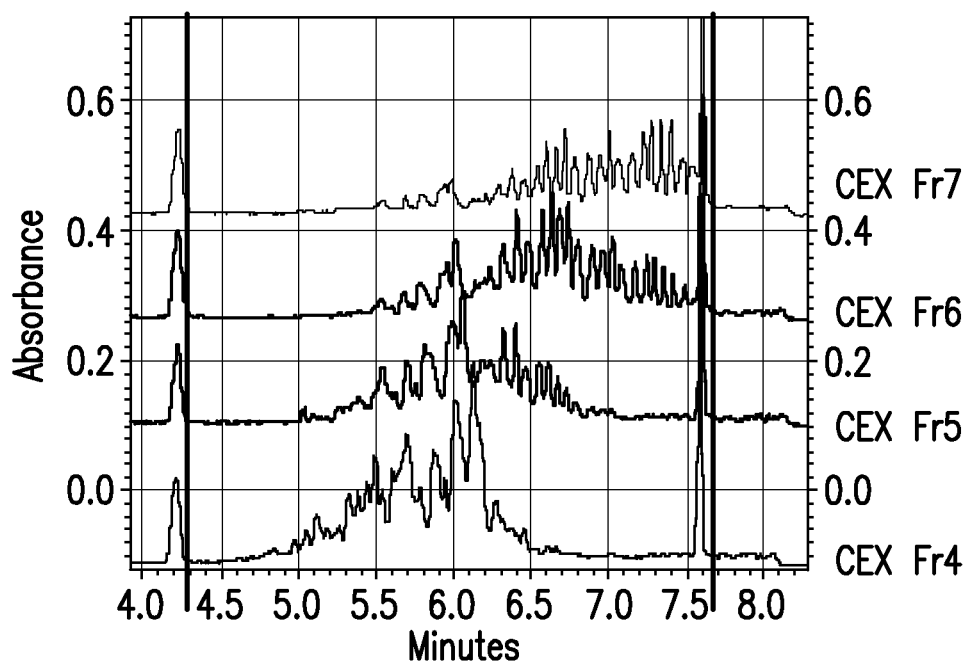
FIG. 19 cIEF profile for CEX eluate fractions from CHO cell line clone 23D8 as compared to reference compound.
Figure 19B:
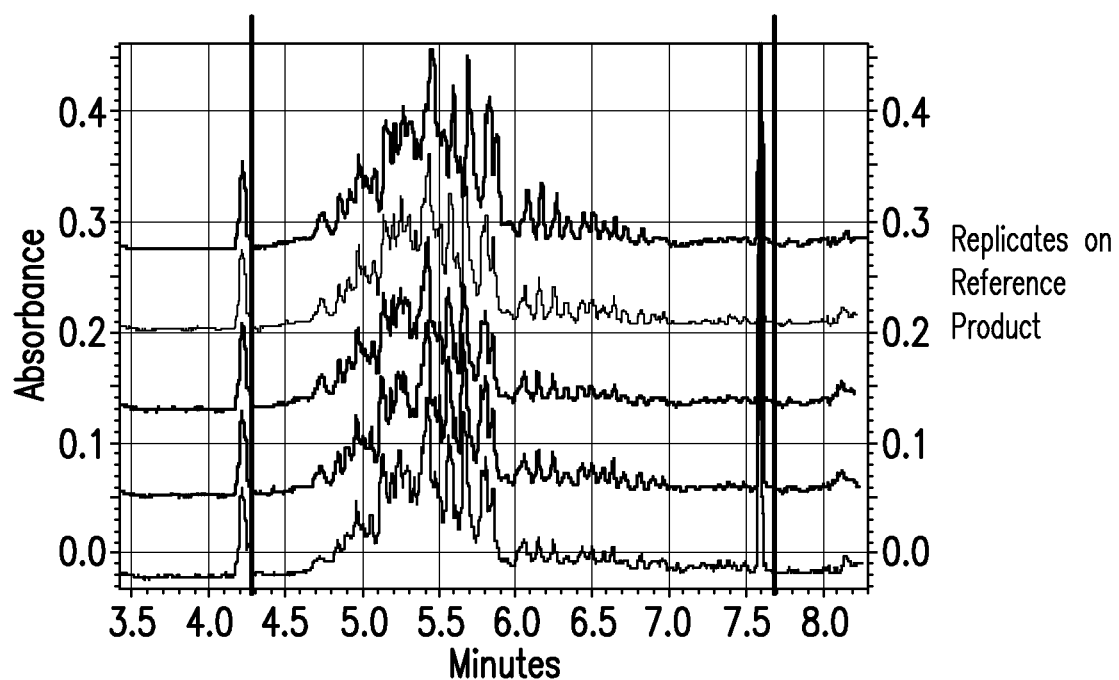
Figure 20:
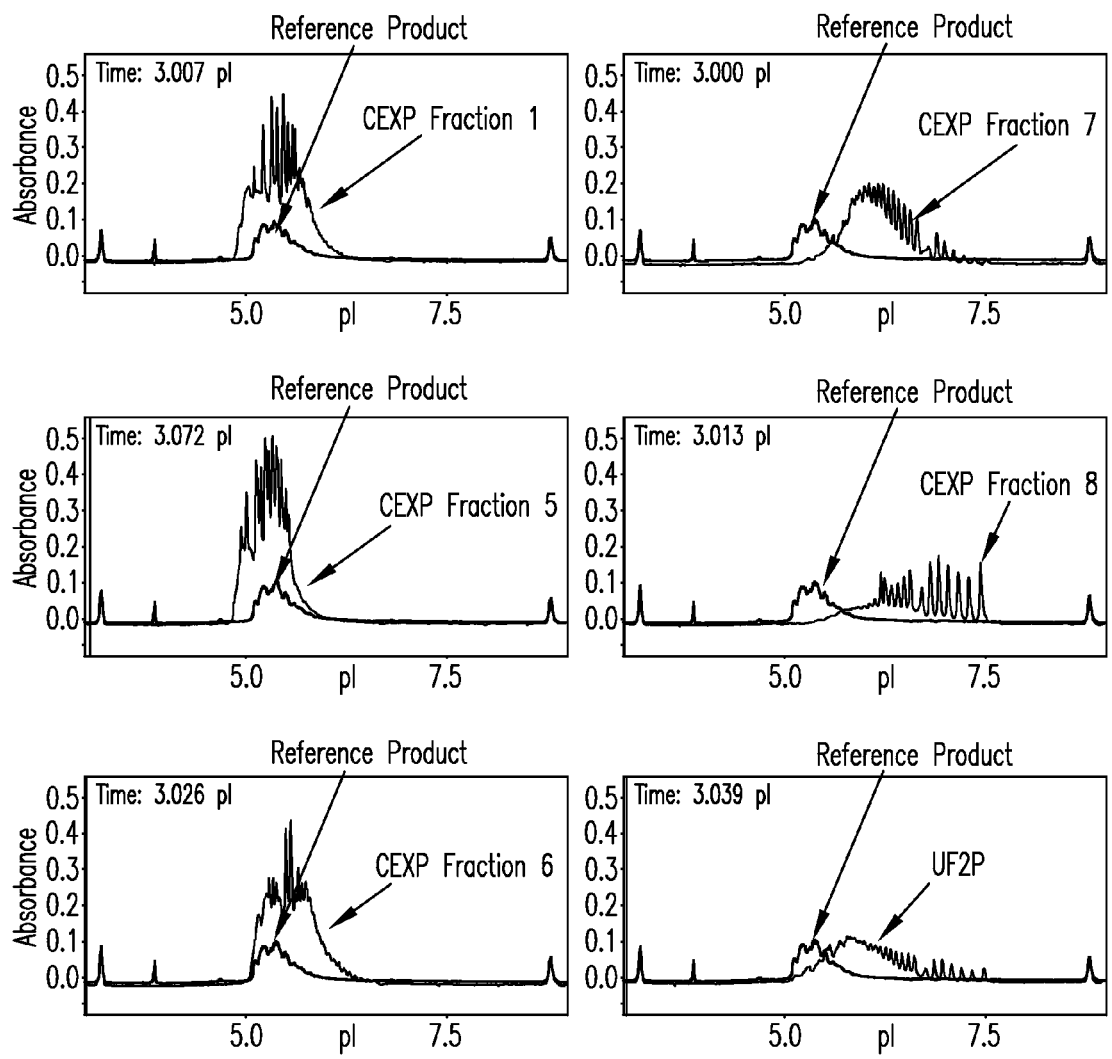
FIG. 20 cIEF profile for CEX eluate fractions from CHO cell line clone 18G10 as compared to reference compound.

For both clones, earlier eluting. CEXP fractions are more acidic, with cIEF profiles that overlap well with the innovator compared to later eluting fractions (FIG. 19 and FIG. 20). FIG. 19 A provides cIEF profiles for clone 23D8 CEXP fractions 4-7. FIG. 19B provide cIEF profiles for provides replicate cIEF profiles for samples of the reference product (ENBREL® Lot 1011803) for comparison. FIG. 20 cIEF profile for CEXP fractions 1, 5, 6, 7, 8 and UF2P from clone 18G10.

For both clones, the CEX feed had HCP and DNA levels below the limit of detection. Table 21 provides data summarizing the clearance of leached PrA ligand across CEX fractions. The data indicate that later eluting fractions have higher levels of the impurity.

TABLE 21

| Clone | Sample | PrA ligand (ng/mL) |
|---|---|---|
| 23D8 | CEXP Fr1 | <0.7 |
| | CEXP Fr2 | <0.7 |
| | CEXP Fr3 | <0.7 |
| | CEXP Fr4 | <0.7 |
| | CEXP Fr5 | 0.7 |
| | CEXP Fr6 | 146 |
| | CEXP Fr7 | 1533 |
| | UF2P | 171 |
| 18G10 | CEXP Fr1 | 12 |
| | CEXP Fr2 | 4.1 |
| | CEXP Fr5 | <1.2 |
| | CEXP Fr6 | <1.2 |

TABLE 21-continued

| Clone | Sample | PrA ligand (ng/mL) |
|---|---|---|
| | CEXP Fr7 | 3 |
| | CEXP Fr8 | 38 |
| | UF2P | 28 |

The normalized EC50 result of pooled CEXP fractions for clone 23D8 was 1.07, which was similar to that of 18G10, which was 1.01. No trend was apparent with the fraction number (Table 22).

TABLE 22

| Clone | Sample | Normalized EC50 |
|---|---|---|
| 23D8 | CEXP Fr4 | 1.08 |
| | CEXP Fr5 | 1.00 |
| | CEXP Fr6 | 0.87 |
| | CEXP Fr7 | 1.11 |
| | Pooled CEXP | 1.07 |
| 18G10 | CEXP Fr1 | 0.90 |
| | CEXP Fr2 | 0.85 |
| | CEXP Fr5 | 0.94 |
| | CEXP Fr6 | 1.16 |
| | CEXP Fr7 | 1.04 |
| | CEXP Fr8 | 1.02 |
| | Pooled CEXP | 1.01 |

D. Ultrafiltration

The pooled CEXP fractions were concentrated and diafiltered prior to AEX to reduce the conductivity of the feed. Pooled CEXP was concentrated ~5× and diafiltered 5× into 12.5 mM NaPi, pH 6.3, using a Millipore regenerated cellulose membrane w/30 kD pore size.

The yield across UF2 was lower than expected, at 77% for clone 23D8, possibly due to an imperfection in the membrane. The permeate contained 13% of the material. The yield for clone 18G10 was 98%.

E. Anion Exchange Chromatography

AEX was performed to further enrich the content of TSA, Peak2, and monomer, and clear residual impurities. AEX Feed was UF2P adjusted to pH 8.0 with 1M Trizmabase. The processing conditions are summarized in Table 23. Loading was ≤10 g/L CV. A single injection was done for 23D8 feed, and two injections were done for 18G10 feed to remain below the loading limit. AEX was performed at pH 8.0, with elution by a 20 CV linear gradient from 0-0.3M NaCl, with collection of 1 CV fractions. Data from all the analytical assays available (HP-PrA, HP-HIC, HP-SEC, TSA, cIEF, EC50, and residual impurities) were examined before deciding which fractions to pool for the final formulation.

TABLE 23

| Feed | UF2P, adjusted to pH 8.0 |
|---|---|
| Resin | Poros 50 HQ |
| Col loading (g/L CV) | ≤10 |
| Residence time (min) | ≥4 |

| Step | Buffer | Column Volume (CV) |
|---|---|---|
| Sanitize | 0.1N NaOH | 1 |
| Pre-equi | 12.5 mM NaPi, 1M NaCl, pH 8.0 | 2 |
| Equi | 12.5 mM NaPi, pH 8.0 | 5 |
| Load | Feed | — |
| Wash | 12.5 mM NaPi, pH 8.0 | 2 |
| Elution | 12.5 mM NaPi, pH 8.0, 0M --> 0.3M NaCl, collect 1CV fractions | 20 |

TABLE 23-continued

| | | |
|---|---|---|
| Salt strip1 | 12.5 mM NaPi, 0.5M NaCl, pH 8.0 | 1 |
| Salt strip2 | 12.5 mM NaPi, 1M NaCl, pH 8.0 | 3 |
| Storage | 0.1N NaOH | 3 |

The elution profile for the two clones is shown in FIG. 21 (23D8 in 21A and 18G10 in 21B). Both clones 23D8 and 18G10 eluted between ~4-24 mS/cm. Two injections performed for 18G10 had identical profiles (data not shown), indicating that AEX performance is reproducible. Table 24 summarizes yield and product quality for each of the clones. In order to assure the purity and quality of the POI later eluting fractions which were observed to contain higher Peak3 content were not be pooled. Clone 23D8 had significantly higher yield during AEX than clone 18G10.

TABLE 24

| | Clone | 23D8 | 18G10 |
|---|---|---|---|
| Cond of pooled AEXP fr's (mS/cm) | | 16-22 | 19-22 |
| % Yield | | 50% | 23% |
| % MB | | 98% | 99% |
| Pooled AEXP TSA (RP lot 1011803) | | 88% | 89% |
| Pooled AEXP Normalized EC50 | | 0.97 | 0.95 |
| HP-SEC on Pooled AEXP | % Agg | 1% | 3% |
| | % Monomer | 99% | 97% |
| HP-HIC on Pooled AEXP | % Peak1 | 1% | 4% |
| | % Peak2 | 95% | 90% |
| | % Peak3 | 5% | 6% |
| Residuals for Pooled AEXP (ng/mL) | HCP | <29 | <24 |
| | PrA ligand | 210 | 150 |
| | DNA | <3.8 | <3.8 |

Figure 22:
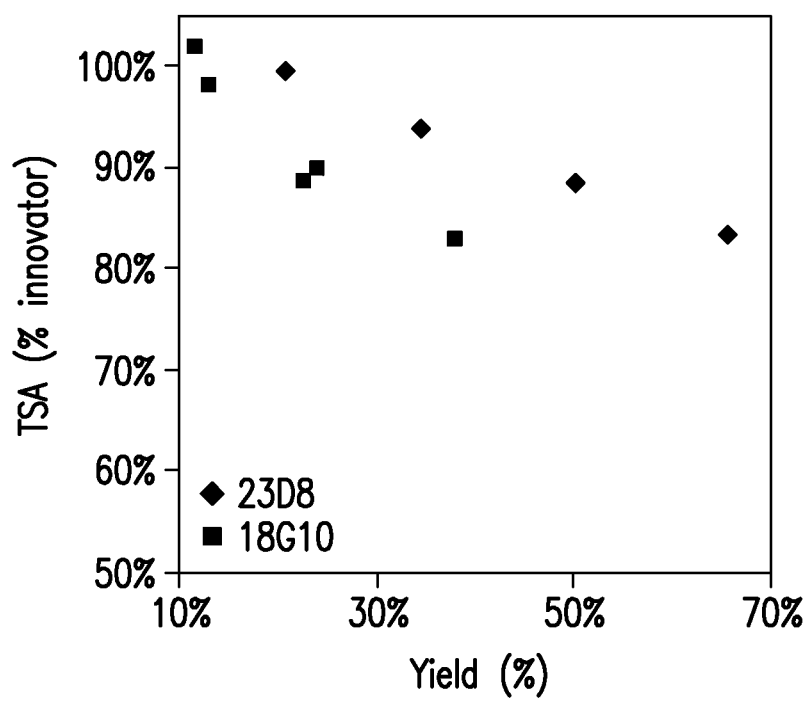
FIG. 22 TSA levels of pooled AEX fractions as a function of yield. TSA values are reported relative to reference compound.
Figure 23A:
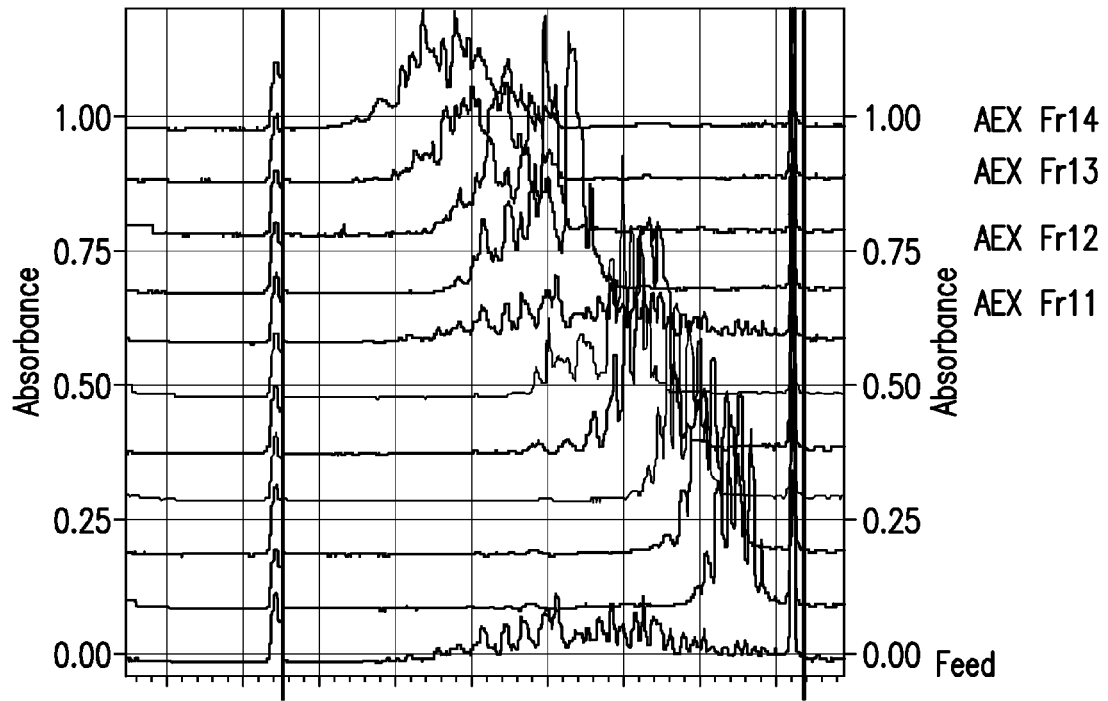
FIG. 23 cIEF profile for AEX eluate fractions from CHO cell line clone 23D8 as compared to reference compound.
Figure 23B:
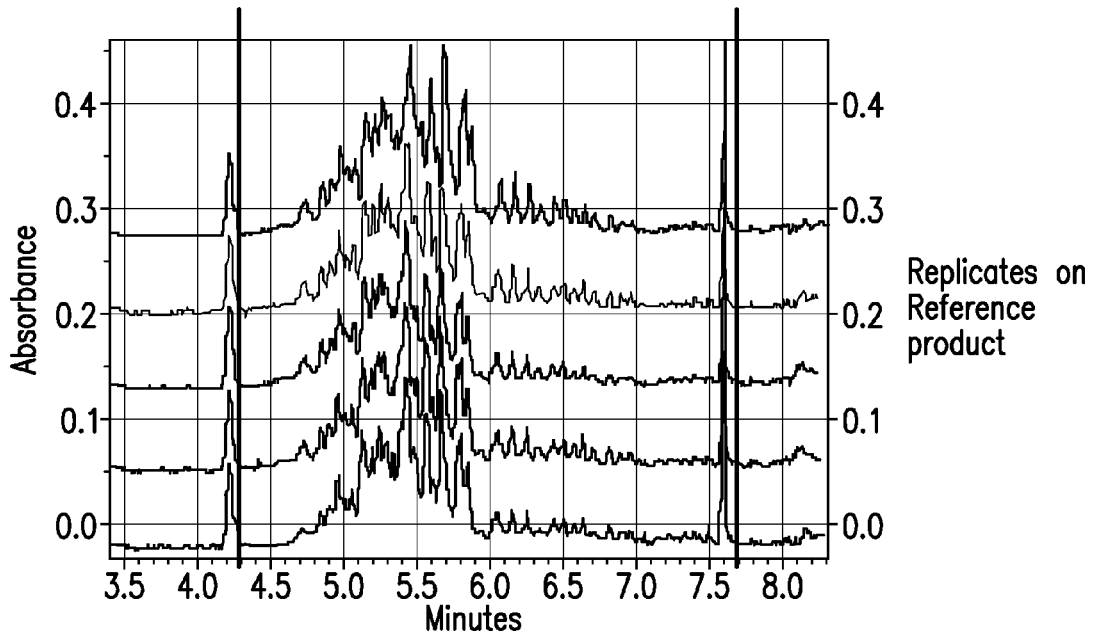
Figure 24:
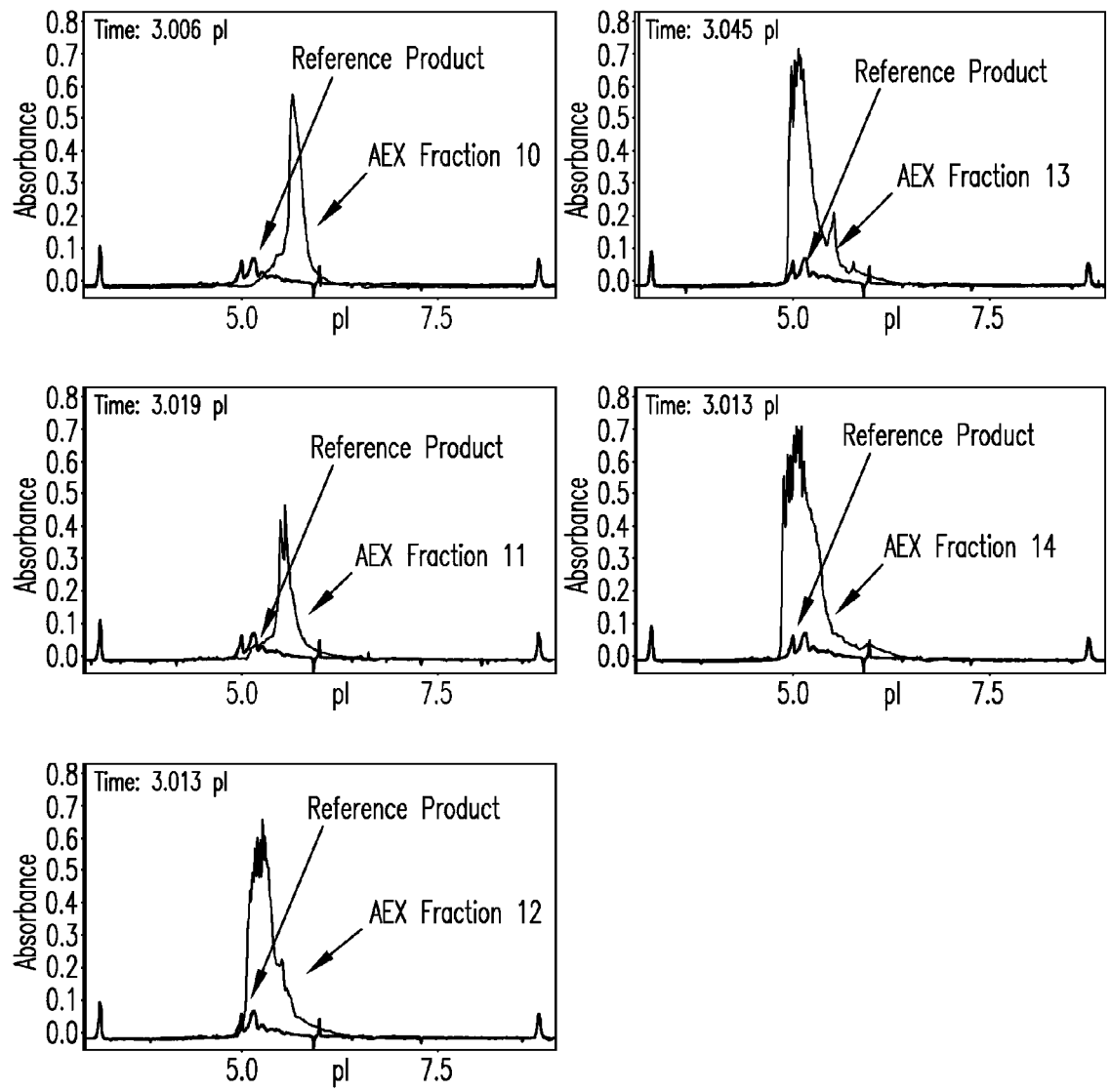
FIG. 24 cIEF profile for AEX eluate fractions from CHO cell line clone 18G10 as compared to reference compound.

In general, later eluting AEXP fractions were observed to be enriched for TSA. FIG. 22 illustrates that during AEX, a significantly better balance between yield and TSA was attained for clone 23D8. For both clones, later eluting AEXP fractions are more acidic (FIG. 23 and FIG. 24). For clone 23D8, fractions 11-14 have an acceptable degree of overlap with the reference product protein, as do fractions 11-13 from clone 18G10. It was observed that earlier eluting fractions were not comparable with the reference product.

For both clones, the AEX feed had HCP and DNA levels below the limit of detection. Table 25 summarizes the clearance of leached PrA ligand.

TABLE 25

| Clone | Sample | PrA ligand (ng/mL) |
|---|---|---|
| 23D8 | AEXP Fr4 | 0.8 |
| | AEXP Fr6 | 1.2 |
| | AEXP Fr7 | <0.7 |
| | AEXP Fr8 | <0.7 |
| | AEXP Fr9 | 418 |
| | AEXP Fr10 | 350 |
| | AEXP Fr11 | 200 |
| | AEXP Fr12 | 263 |
| | AEXP Fr13 | 141 |
| | AEXP Fr14 | 93 |
| | AEXP Fr15 | 66 |
| | AEXP Fr16 | 57 |
| 18G10 | AEXP Fr4 | <1.2 |
| | AEXP Fr5 | <1.2 |
| | AEXP Fr6 | <1.2 |
| | AEXP Fr7 | <1.3 |
| | AEXP Fr8 | <1.3 |
| | AEXP Fr9 | <1.3 |
| | AEXP Fr10 | <1.3 |
| | AEXP Fr11 | <1.2 |
| | AEXP Fr12 | <1.2 |
| | AEXP Fr13 | 447 |
| | AEXP Fr14 | 705 |

The normalized EC50 result of pooled AEXP fractions for clone 23D8 was 0.97, which was similar to that of 18G10, which was 0.95. Table 26 indicates that no trend was apparent across the fractions.

TABLE 26

| Clone | Sample | Normalized EC50 |
|---|---|---|
| 23D8 | AEXP Fr5 | 1.23 |
| | AEXP Fr6 | 1.11 |
| | AEXP Fr7 | 1.12 |
| | AEXP Fr8 | 1.06 |
| | AEXP Fr9 | 1.10 |
| | AEXP Fr10 | 0.98 |
| | AEXP Fr11 | 1.08 |
| | AEXP Fr12 | 0.94 |
| | AEXP Fr13 | 0.94 |
| | AEXP Fr14 | 0.90 |
| 18G10 | AEXP Fr4 | 1.01 |
| | AEXP Fr5 | 1.13 |
| | AEXP Fr6 | 1.05 |
| | AEXP Fr7 | 1.02 |
| | AEXP Fr8 | 1.03 |
| | AEXP Fr9 | 0.96 |
| | AEXP Fr10 | 0.97 |
| | AEXP Fr11 | 1.01 |
| | AEXP Fr12 | 0.93 |
| | AEXP Fr13 | 0.91 |
| | AEXP Fr14 | 0.93 |

For Clone 23D8, fractions 11-14, which eluted between 16-22 mS/cm, were pooled. The TSA content of those fractions was between 85-115% of the reference product. Peak2 content was >90% and aggregates were ≤4%. The pooled fractions had cIEF profiles with an acceptable degree of overlap with the reference product. HCP and DNA were below detection. EC50 was between 0.9-1.08 for all fractions.

For Clone 18G10, fractions 11-13, which eluted between 19-22 mS/cm, were pooled. The TSA content of those fractions was between 80-100% of the innovator. Peak2 content was ~90% and aggregates were <5%. The pooled fractions had cIEF profiles with acceptable levels of overlap with the reference product. HCP and DNA were below detection. EC50 was between 0.91-1.01 for all fractions.

E. Ultrafiltration

The pooled AEXP fractions were concentrated and diafiltered into the formulation buffer. Pooled AEXP fractions were concentrated to 50 g/L and diafiltered 5× into 25 mM NaPi, 25 mM Arg, 100 mM NaCl, 1% sucrose, pH 6.3, using a Millipore regenerated cellulose membrane w/30 kD pore size.

The yields across UF4 were 98% and 80% for clones 23D8 and 18G10, respectively, with mass balances of 101% and 84%. The UF4P contained 900 mg for clone 23D8 and 630 mg for clone 18G10.

The overall productivities, when pooling AEXP fractions with TSA values >80% of the reference product Peak2 content, were 97.2 and 32.5 mg/L for clones 23D8 and 18G10, respectively. In comparison, the productivity of *Pichia*-expressed material was 40 mg/L when fractions with a TSA value of >50% were pooled.

SUMMARY

Figure 2:
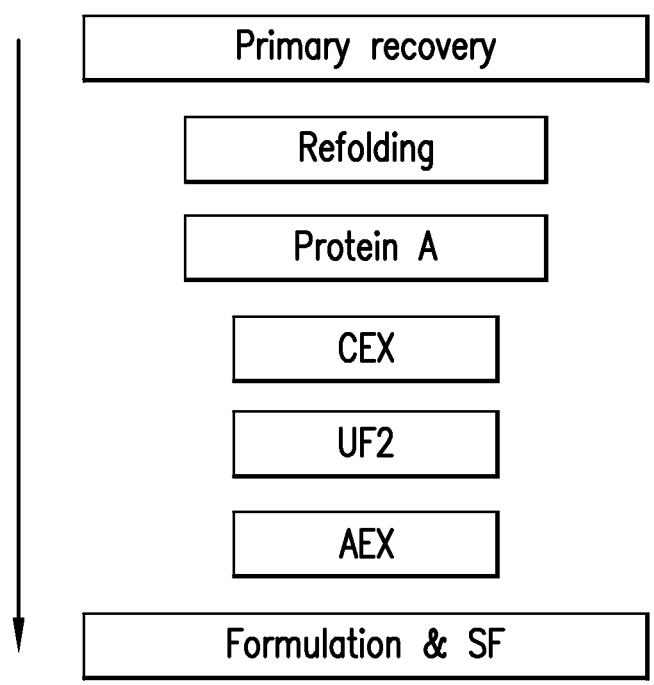
FIG. 2 Depicts a purification scheme for TNFR:Fc produced in CHO cells.
Figure 3:
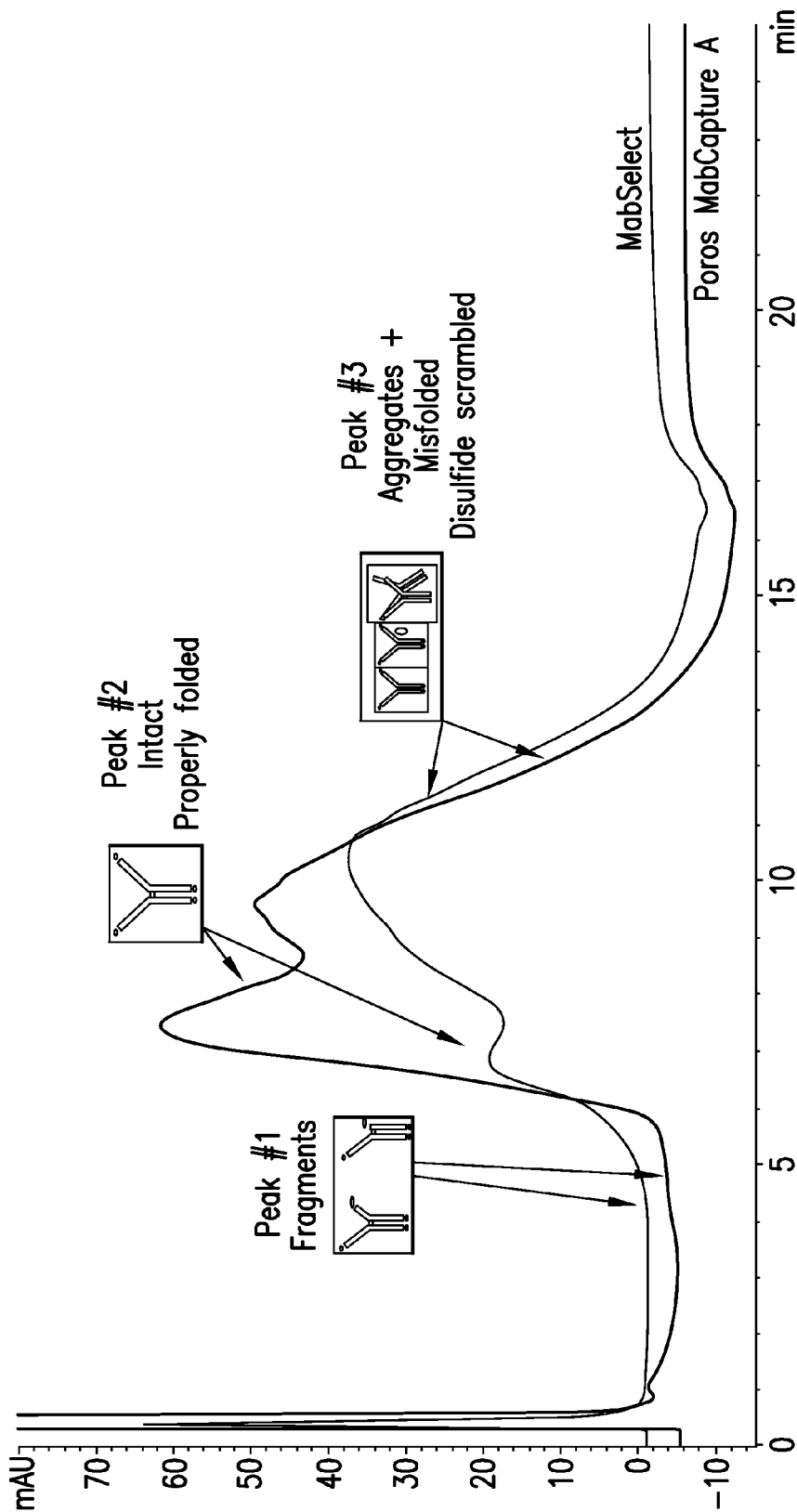
FIG. 3 Comparison of MabSelect and Poros MabCapture A QPAP streams on an analytical HIC chromatogram.

Cell culture feeds from Chinese hamster ovary (CHO) clones 23D8 and 18G10 were purified through a process similar to that developed for *Pichia*-expressed TNFR:Fc. The batches were taken through primary recovery, Protein A chromatography (PrA), cation exchange chromatography (CEX), ultrafiltration, anion exchange chromatography (AEX), and final formulation (FIG. 2). Fractions were collected during elution for each of the chromatography steps. Protein A product (PAP) and CEX product (CEXP) fractions were analyzed in process by HP-HIC and HP-SEC to decide which fractions to pool for the following step. Pooled fractions had a high content of correctly folded species (Peak2) that was monomeric. Rejected fractions were high in either fragments (Peak1), misfolded species (Peak3), or aggregates. AEX product (AEXP) fractions were further analyzed for total sialic acid (TSA) content, capillary isoelectric focusing (cIEF) profile, normalized EC50, and impurities before deciding which fractions to pool for the final formulation. The yields for both feeds are summarized in Table 27.

TABLE 27

|  | Clone | 23D8 | 18G10 |
|---|---|---|---|
| Ferm broth | Ferm broth titer (g/L) | 0.35 | 0.35 |
| Primary recovery | % Yield (approx) | 90% | 90% |
| PrA | % Yield | 70% | 56% |
|  | % MB | 82% | 95% |
|  | HP-HIC on Pooled QPAP (% Peak1, 2, 3) | 4, 94, 2% | 1, 96, 3% |
| CEX | % Yield | 98% | 89% |
|  | % MB | 99% | 99% |
|  | HP-HIC on Pooled CEXP (% Peak1, 2, 3) | 2, 96, 2% | 2, 96, 3% |
| UF2 | % Yield (approx) | 90% | 90% |
| AEX | % Yield | 50% | 23% |
|  | % MB | 98% | 99% |
|  | HP-HIC on Pooled AEXP (% Peak1, 2, 3) | ~2, 96, 2% | ~4, 90, 6% |
| Overall | TSA (% innovator) | 88% | 89% |
|  | % Yield (approx) | 28% | 9% |
|  | Productivity (mg/L ferm broth) | 97.2 | 32.5 |

Other embodiments are within the following claims. While several embodiments have been shown and described, various modifications may be made without departing from the spirit and scope of the present invention.

What is claimed is:

1. A method of purifying a p75 TNFR:Fc-fusion protein from one or more impurites in a sample, comprising the steps of:
   a) providing a sample comprising the Fc-fusion protein produced in a eukaryotic expression system;
   b) binding the Fc-fusion protein present in the sample to a Protein A affinity chromatography resin;
   c) eluting the Fc-fusion protein from the Protein A resin, by applying to the Protein A resin, an elution buffer gradient of from 50 mM Citrate pH 5.0 to 100 mM Citrate pH 4.0, wherein the eluted product provides a second sample;
   d) binding the second sample to a cation exchange (CEX) chromatography resin;
   e) eluting the second sample from the CEX resin by applying to the CEX resin, a linear elution buffer gradient of from 25 mM sodium phosphate, 25 mM arginine pH 4.0, 0.25 M NaCl to 25 mM sodium phosphate, 25 mM arginine pH 4.0, 0.65 M NaCl, wherein the eluted product provides a third sample;
   f) binding the third sample to an anion exchange (AEX) chromatography resin; and
   g) eluting the third sample from the AEX resin by applying, to the AEX resin, a linear elution buffer gradient of from 12.5 mM sodium phosphate, pH 8.0 to 12.5 mM sodium phosphate, 300 mM NaCl, pH 8.0, wherein the eluted product provides a purified p75 TNFR:Fc-fusion protein composition.

2. The method according to claim 1, wherein step b) further comprises:
   b') washing the bound Fc-fusion protein with a buffer having a pH ranging from 3 to 7 and conductivity range of 10 ms/cm to 50 ms/cm.

3. The method according to claim 1 wherein the Protein A chromatography resin comprises cross-linked poly(styrene-divinylbenzene).

4. The method according to claim 1 wherein the CEX chromatography step is carried out on a strong cation exchange resin and the AEX chromatography step is carried out on a strong anion exchange resin.

5. The method according to claim 4 wherein the CEX chromatography resin is surface coated with polyhydroxylated polymer functionalized with sulfopropyl and the AEX chromatography resin is surface coated with fully quaternized polyethyleneimine.

6. The method according to claim 1, wherein the sample comprising the Fc-fusion protein is mammalian cell culture broth or yeast fermentation broth.

7. The method according to claim 6, wherein the sample comprising the Fc-fusion protein is yeast fermentation broth and step a) further comprises:
   a') adjusting the pH of the sample comprising the Fc-fusion protein to a pH between 8 to 9 and contacting the sample with a refolding agent and a disaggregation agent.

8. The method according to claim 7, wherein the refolding agent is selected from arginine, glycerol, EDTA, TMAO, PEG-3500 or a redox reagent and the disaggregation agent is selected from urea or guanidine hydrochloride.

9. The method according to claim 7, wherein the pH of the sample comprising the Fc-fusion protein is adjusted to 8.6.

10. The method according to claim 1, wherein the purified Fc-fusion protein composition obtained in step g) provides a product with purity of >99%.

11. The method according to claim 1, wherein the purified Fc-fusion protein composition obtained in step g) is characterized by a TSA level of >18 mMol.

12. The method of claim 1 wherein the p75 TNFR:Fc fusion protein is etanercept.

13. The method of claim 1 wherein step e) comprises: eluting the second sample from the CEX resin by applying to the CEX resin, a linear elution buffer gradient of from 25 mM sodium phosphate, 25 mM arginine pH 4.0, 0.25 M NaCl to 25 mM sodium phosphate, 25 mM arginine pH 4.0, 0.65 M NaCl, and collecting product that elutes when the elution buffer ionic strength is between 37 ms/cm and 42 ms/cm; wherein the eluted product that is collected provides a third sample.

14. The method of claim 1 wherein step g) comprises: eluting the third sample from the AEX resin by applying, to the AEX resin, a linear elution buffer gradient of from 12.5 mM sodium phosphate, pH 8.0 to 12.5 mM sodium phosphate, 300 mM NaCl, pH 8.0, and collecting product that elutes when the elution buffer ionic strength is between 4 ms/cm and 24 ms/cm; wherein the eluted product provides a purified p75 TNFR:Fc-fusion protein composition.

15. The method of claim 1 comprising:
   a) providing a sample comprising the Fc-fusion protein produced in a Chinese hamster ovary cell expression system;
   b) binding the Fc-fusion protein present in the sample to a Protein A affinity chromatography resin;
   c) eluting the Fc-fusion protein from the Protein A resin, by applying to the Protein A resin, an elution buffer gradient of from 50 mM Citrate pH 5.0 to 100 mM Citrate pH 4.0, wherein the eluted product provides a second sample;
   d) binding the second sample to a cation exchange (CEX) chromatography resin;
   e) eluting the second sample from the CEX resin by applying to the CEX resin, a linear elution buffer gradient of from 25 mM sodium phosphate, 25 mM arginine pH 4.0, 0.25 M NaCl to 25 mM sodium phosphate, 25 mM arginine pH 4.0, 0.65 M NaCl, and collecting product that elutes when the elution buffer ionic strength is between 37 ms/cm and 42 ms/cm; wherein the eluted product that is collected provides a third sample;
   f) binding the third sample to an anion exchange (AEX) chromatography resin; and
   g) eluting the third sample from the AEX resin by applying, to the AEX resin, a linear elution buffer gradient of from 12.5 mM sodium phosphate, pH 8.0 to 12.5 mM sodium phosphate, 300 mM NaCl, pH 8.0, and collecting product that elutes when the elution buffer ionic strength is between 4 ms/cm and 24 ms/cm;
   wherein the eluted product provides a purified p75 TNFR: Fc-fusion protein composition.

16. The method of claim 15 wherein the TNFR:Fc-fusion protein is etanercept.

* * * * *